United States Patent
Han et al.

(10) Patent No.: US 9,242,940 B2
(45) Date of Patent: Jan. 26, 2016

(54) N-SUBSTITUTED BIS(FLUOROALKYL)-1,4-BENZODIAZEPINONE COMPOUNDS

(71) Applicant: BRISTOL-MYERS SQUIBB COMPANY, Princeton, NJ (US)

(72) Inventors: Wen-Ching Han, Newtown, PA (US); Patrice Gill, Levittown, PA (US); Ashvinikumar V. Gavai, Princeton Junction, NJ (US); Claude A. Quesnelle, Skillman, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 14/429,945

(22) PCT Filed: Sep. 20, 2013

(86) PCT No.: PCT/US2013/060836
§ 371 (c)(1),
(2) Date: Mar. 20, 2015

(87) PCT Pub. No.: WO2014/047393
PCT Pub. Date: Mar. 27, 2014

(65) Prior Publication Data
US 2015/0246892 A1    Sep. 3, 2015

Related U.S. Application Data

(60) Provisional application No. 61/703,922, filed on Sep. 21, 2012.

(51) Int. Cl.
| | |
|---|---|
| *C07D 401/04* | (2006.01) |
| *C07D 243/18* | (2006.01) |
| *C07D 491/04* | (2006.01) |
| *C07D 243/16* | (2006.01) |
| *C07D 243/26* | (2006.01) |
| *A61K 31/138* | (2006.01) |
| *A61K 31/337* | (2006.01) |
| *A61K 31/506* | (2006.01) |
| *A61K 31/5513* | (2006.01) |
| *A61K 31/555* | (2006.01) |
| *A61K 31/573* | (2006.01) |
| *A61K 45/06* | (2006.01) |
| *C07D 491/056* | (2006.01) |

(52) U.S. Cl.
CPC ............ *C07D 243/16* (2013.01); *A61K 31/138* (2013.01); *A61K 31/337* (2013.01); *A61K 31/506* (2013.01); *A61K 31/555* (2013.01); *A61K 31/5513* (2013.01); *A61K 31/573* (2013.01); *A61K 45/06* (2013.01); *C07D 243/18* (2013.01); *C07D 243/26* (2013.01); *C07D 401/04* (2013.01); *C07D 491/04* (2013.01); *C07D 491/056* (2013.01)

(58) Field of Classification Search
CPC ..... C07D 401/04; C07D 243/18; C07D 491/04
See application file for complete search history.

(56) References Cited

U.S. PATENT DOCUMENTS

| 4,981,847 A | 1/1991 | Sato et al. |
| 5,322,842 A | 6/1994 | Sato et al. |

(Continued)

FOREIGN PATENT DOCUMENTS

| EP | 0669334 | 8/1995 |
| WO | WO 97/36879 | 10/1997 |

(Continued)

OTHER PUBLICATIONS

U.S. Appl. No. 14/627,573, filed Feb. 20, 2015, Gavai et al.
Groth, C., et al., "Therapeutic approaches to modulating Notch signaling: Current challenges and future prospects," Seminars in Cell & Developmental Biology, (2012), doi:10.1016/j.semcdb2012.01.016; available online Mar. 7, 2012.
Seiffert, D., et al., "Presenilin-1 and -2 Are Molecular Targets for gamma-Secretase Inhibitors," The Journal of Biological Chemistry, vol. 275, No. 44, pp. 34086-34091 (2000).
Beher, D., et al., "Pharmacological Knock-down of the Presenilin 1 Heterodimer by a Novel gamma-Secretase Inhibitor," The Journal of Biological Chemistry, vol. 276, No. 48, pp. 45394-45402 (2001).
Iben, L.G., et al., "Signal Peptide Peptidase and gamma-Secretase Share Equivalent Inhibitor Binding Pharmacology," The Journal of Biological Chemistry, vol. 282, No. 51, pp. 36829-36836 (2007).
Meredith, Jere, "Characterization of APP Activity and Notch Toxicity with gamma-Secretase Inhibitors," 8th International AD/PD Meeting, Salzberg, Austria, Mar. 17, 2007.

(Continued)

*Primary Examiner* — Bruck Kifle
(74) *Attorney, Agent, or Firm* — Gary D. Greenblatt

(57) ABSTRACT

Disclosed are compounds of Formula (I): wherein: $R_1$ is —$CH_2CH_2CF_3$; $R_2$ is —$CH_2CH_2CF_3$, or —$CH_2CH_2CH_2CF_3$; $R_3$ is —$CH_2CF_3$, —$CH_2CN$, —$CH_2$(cyclopropyl), pyridinyl, chloropyridinyl, or tetrahydropyranyl; Ring A is phenyl or pyridinyl; $R_a$, $R_b$, y, and z are defined herein. Also disclosed are methods of using such compounds to inhibit the Notch receptor, and pharmaceutical compositions comprising such compounds. These compounds are useful in treating, preventing, or slowing the progression of diseases or disorders in a variety of therapeutic areas, such as cancer.

(I)

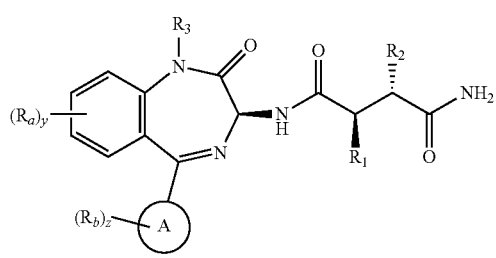

8 Claims, No Drawings

(56) References Cited

U.S. PATENT DOCUMENTS

| | | | |
|---|---|---|---|
| 5,324,726 | A | 6/1994 | Bock et al. |
| 5,852,010 | A | 12/1998 | Graham et al. |
| 5,998,407 | A | 12/1999 | Graham et al. |
| 6,331,408 | B1 | 12/2001 | Zaczek et al. |
| 6,495,540 | B2 | 12/2002 | Thompson |
| 6,503,901 | B1 | 1/2003 | Thompson et al. |
| 6,503,902 | B2 | 1/2003 | Olson et al. |
| 6,509,333 | B2 | 1/2003 | Olson |
| 6,525,044 | B2 | 2/2003 | Olson et al. |
| 6,544,978 | B2 | 4/2003 | Wu et al. |
| 6,632,812 | B2 | 10/2003 | Han et al. |
| 6,653,303 | B1 | 11/2003 | Wu et al. |
| 6,713,476 | B2 | 3/2004 | Yang et al. |
| 6,737,038 | B1 | 5/2004 | Zaczek et al. |
| 6,756,511 | B2 | 6/2004 | Pineiro et al. |
| 6,759,404 | B2 | 7/2004 | Olson et al. |
| 6,794,381 | B1 | 9/2004 | Olson et al. |
| 6,878,363 | B2 | 4/2005 | Zaczek et al. |
| 6,900,199 | B2 | 5/2005 | Han et al. |
| 6,958,329 | B2 | 10/2005 | Olson |
| 6,960,576 | B2 | 11/2005 | Olson et al. |
| 6,962,913 | B2 | 11/2005 | Olson et al. |
| 6,984,626 | B2 | 1/2006 | Nadin et al. |
| 7,001,901 | B2 | 2/2006 | Yang |
| 7,053,081 | B2 | 5/2006 | Olson et al. |
| 7,053,084 | B1 | 5/2006 | Olson |
| 7,101,870 | B2 | 9/2006 | Olson et al. |
| 7,105,509 | B2 | 9/2006 | Pineiro et al. |
| 7,112,583 | B2 | 9/2006 | Olson et al. |
| 7,125,866 | B1 | 10/2006 | Glick et al. |
| 7,153,491 | B2 | 12/2006 | Zaczek et al. |
| 7,160,875 | B2 | 1/2007 | Flohr et al. |
| 7,276,495 | B2 | 10/2007 | Han et al. |
| 7,276,496 | B2 | 10/2007 | Olson et al. |
| 7,304,049 | B2 | 12/2007 | Olson |
| 7,304,055 | B2 | 12/2007 | Olson et al. |
| 7,304,056 | B2 | 12/2007 | Olson et al. |
| 7,342,008 | B2 | 3/2008 | Olson et al. |
| 7,354,914 | B2 | 4/2008 | Olson |
| 7,375,099 | B2 | 5/2008 | Galley et al. |
| 7,390,802 | B2 | 6/2008 | Han et al. |
| 7,390,896 | B2 | 6/2008 | Olson et al. |
| 7,423,033 | B2 | 9/2008 | Olson et al. |
| 7,456,172 | B2 | 11/2008 | Olson |
| 7,456,278 | B2 | 11/2008 | Olson |
| 7,498,324 | B2 | 3/2009 | Han et al. |
| 7,528,249 | B2 | 5/2009 | Olson et al. |
| 7,544,679 | B2 | 6/2009 | Flohr et al. |
| 7,582,624 | B2 | 9/2009 | Carter et al. |
| 7,655,647 | B2 | 2/2010 | Han et al. |
| 7,718,795 | B2 | 5/2010 | Olson |
| 8,629,136 | B2 | 1/2014 | Gavai et al. |
| 8,822,454 | B2 | 9/2014 | Gavai et al. |
| 8,999,918 | B2 | 4/2015 | Gavai et al. |
| 2007/0185094 | A1 | 8/2007 | Lattmann et al. |
| 2009/0181944 | A1 | 7/2009 | Boylan et al. |
| 2014/0357805 | A1 | 12/2014 | Gavai et al. |

FOREIGN PATENT DOCUMENTS

| | | |
|---|---|---|
| WO | WO 01/74796 | 10/2001 |
| WO | WO 01/90084 | 11/2001 |
| WO | WO 2007/067048 | 6/2007 |
| WO | WO 2009/023453 | 2/2009 |
| WO | WO 2014/047369 | 3/2014 |
| WO | WO 2014/047370 | 3/2014 |
| WO | WO 2014/047374 | 3/2014 |
| WO | WO 2014/047390 | 3/2014 |
| WO | WO 2014/047391 | 3/2014 |
| WO | WO 2014/047392 | 3/2014 |
| WO | WO 2014/047397 | 3/2014 |

OTHER PUBLICATIONS

Prasad, C.V.C., et al., "Discovery of (S)-2-((S)-2(3,5-difluorophenyl)-2-hydroxyacetamido)-N-((S,Z)-3-methyl-4-oxo-4,5-dihydro-3H-benzo[d][1,2]diazepin-5-yl)propanamide (BMS-433796): A gamma-secretase inhibitor with with A beta lowering activity in a transgenic mouse model of Alzheimer's disease," Bioorganic & Medicinal Chemistry Letters 17 pp. 4006-4011 (2007).

Jun, H.T., et al., "Top Notch Targets: Notch Signaling in Cancer," Drug Development Research, 69, pp. 319-328 (2008).

Meredith, J.E., et al., Gamma-Secretase activity is not involved in presenilin-mediated regulation of beta-catenin, Biochemical and Biophysical Research Communications 299 pp. 744-750 (2002).

Shih, L., et al., Notch Signaling, gamma-Secretase Inhibitors, and Cancer Therapy, Cancer Res. 67, pp. 1879-1882 (2007).

Olson, Richard, "Optimizing gamma-secretase Inhibitors for safety and efficacy," 8th International AD/PD Meeting, Mar. 14-18, 2007, Salzberg, Austria.

PCT/US2013/060836 International Search Report mailed Nov. 5, 2013.

PCT/US2013/060836 Preliminary Report on Patentability issued Mar. 24, 2015.

N-SUBSTITUTED BIS(FLUOROALKYL)-1,4-BENZODIAZEPINONE COMPOUNDS

CROSS REFERENCE TO RELATED APPLICATIONS

This application is a national phase application under 35 U.S.C. §371 of International Patent Application No. PCT/US2013/060836 filed Sep. 20, 2013, which claims priority to U.S. Provisional Application 61/703,922, filed Sep. 21, 2012, which are expressly incorporated fully herein by reference.

DESCRIPTION

The present invention generally relates to benzodiazepinone compounds useful as Notch inhibitors. The invention further pertains to pharmaceutical compositions comprising at least one compound according to the invention that is useful for the treatment of conditions related to the Notch pathway, such as cancer and other proliferative diseases.

Notch signaling has been implicated in a variety of cellular processes, such as cell fate specification, differentiation, proliferation, apoptosis, and angiogenesis. (Bray, *Nature Reviews Molecular Cell Biology*, 7:678-689 (2006); Fortini, *Developmental Cell*, 16:633-647 (2009)). The Notch proteins are single-pass heterodimeric transmembrane molecules. The Notch family includes 4 receptors, NOTCH 1-4, which become activated upon binding to ligands from the DSL family (Delta-like 1, 3, 4 and Jagged 1 and 2).

The activation and maturation of NOTCH requires a series of processing steps, including a proteolytic cleavage step mediated by gamma secretase, a multiprotein complex containing Presenilin 1 or Presenilin 2, nicastrin, APH1, and PEN2. Once NOTCH is cleaved, NOTCH intracellular domain (NICD) is released from the membrane. The released NICD translocates to the nucleus, where it functions as a transcriptional activator in concert with CSL family members (RBPSUH, "suppressor of hairless", and LAG1). NOTCH target genes include HES family members, such as HES-1. HES-1 functions as transcriptional repressors of genes such as HERP1 (also known as HEY2), HERP2 (also known as HEY1), and HATH1 (also known as ATOH1).

The aberrant activation of the Notch pathway contributes to tumorigenesis. Activation of Notch signaling has been implicated in the pathogenesis of various solid tumors including ovarian, pancreatic, as well as breast cancer and hematologic tumors such as leukemias, lymphomas, and multiple myeloma. The role of Notch inhibition and its utility in the treatment of various solid and hematological tumors are described in Miele, L. et al., *Current Cancer Drug Targets*, 6:313-323 (2006); Bolos, V. et al., *Endocrine Reviews*, 28:339-363 (2007); Shih, I-M. et al., *Cancer Research*, 67:1879-1882 (2007); Yamaguchi, N. et al., *Cancer Research*, 68:1881-1888 (2008); Miele, L., *Expert Review Anticancer Therapy*, 8:1197-1201 (2008); Purow, B., *Current Pharmaceutical Biotechnology*, 10:154-160 (2009); Nefedova, Y. et al., *Drug Resistance Updates*, 11:210-218 (2008); Dufraine, J. et al., *Oncogene*, 27:5132-5137 (2008); and Jun, H. T. et al., *Drug Development Research*, 69, 319-328 (2008).

There remains a need for compounds that are useful as Notch inhibitors and that have sufficient metabolic stability to provide efficacious levels of drug exposure. Further, there remains a need for compounds useful as Notch inhibitors that can be orally or intravenously administered to a patient.

U.S. Pat. No. 7,053,084 B1 discloses succinoylamino benzodiazepine compounds useful for treating neurological disorders such as Alzheimer's Disease. The reference discloses that these succinoylamino benzodiazepine compounds inhibit gamma secretase activity and the processing of amyloid precursor protein linked to the formation of neurological deposits of amyloid protein.

Applicants have found potent compounds that have activity as Notch inhibitors and have sufficient metabolic stability to provide efficacious levels of drug exposure upon intravenous or oral administration. These compounds are provided to be useful as pharmaceuticals with desirable stability, bioavailability, therapeutic index, and toxicity values that are important to their drugability.

SUMMARY OF THE INVENTION

The present invention fills the foregoing need by providing bis(fluoroalkyl) 1,4-benzodiazepinone compounds that are useful as selective inhibitors of Notch signaling pathway.

The present invention also provides pharmaceutical compositions comprising a pharmaceutically acceptable carrier; and at least one compound of Formula (I).

The present invention also provides a method of treating a disease or disorder associated with the activity of the Notch receptor, the method comprising administering to a mammalian patient at least one compound of Formula (I).

The present invention also provides processes and intermediates for making the compounds of Formula (I).

The present invention also provides the compounds of Formula (I) for use in therapy.

The present invention also provides the use of the compounds of Formula (I) for the manufacture of a medicament for the treatment of cancer.

The compounds of Formula (I) and compositions comprising the compounds are Notch inhibitors that may be used in treating, preventing or curing various Notch receptor-related conditions. Pharmaceutical compositions comprising these compounds are useful in treating, preventing, or slowing the progression of diseases or disorders in a variety of therapeutic areas, such as cancer.

These and other features of the invention will be set forth in expanded form as the disclosure continues.

DETAILED DESCRIPTION

The first aspect of the present invention provides at least one compound of Formula (I):

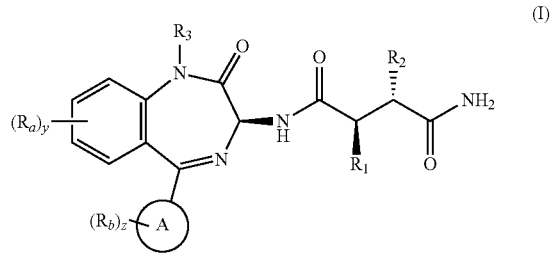

or a prodrug thereof, wherein:
$R_1$ is —$CH_2CF_2CH_3$ or —$CH_2CH_2CF_3$;
$R_2$ is —$CH_2CH_2CF_3$, —$CH_2CH_2CH_2CF_3$, or —$CH_2CF_2CH_3$;
$R_3$ is —$CH_2CF_3$, —$CH_2CN$, —$CH_2$(cyclopropyl), pyridinyl, chloropyridinyl, or tetrahydropyranyl;
Ring A is phenyl or pyridinyl;
each $R_a$ is independently F, Cl, Br, —CN, —OH, —$CH_3$, cyclopropyl, —$CF_3$, —$CH_2CF_3$, —$OCH_3$, —$OCF_3$, and/or —O(cyclopropyl);

or two adjacent $R_a$ along with the carbon atoms to which they are attached form a dioxole ring;
each $R_b$ is independently F, Cl, —CH₃, —CF₃, —CN, and/or —OCH₃;
y is zero, 1, or 2; and
z is zero, 1, or 2.

One embodiment provides at least one compound of Formula (I) wherein $R_1$ is —CH₂CF₂CH₃ and $R_2$, $R_3$, Ring A, $R_a$, $R_b$, y, and z are defined in the first aspect. Included in this embodiment are compounds of Formula (I) in which Ring A is phenyl.

One embodiment provides at least one compound of Formula (I) wherein $R_1$ is —CH₂CH₂CF₃ and $R_2$, $R_3$, Ring A, $R_a$, $R_b$, y, and z are defined in the first aspect. Included in this embodiment are compounds of Formula (I) in which Ring A is phenyl.

One embodiment provides at least one compound of Formula (I) wherein $R_2$ is —CH₂CH₂CF₃ and $R_1$, $R_3$, Ring A, $R_a$, $R_b$, y, and z are defined in the first aspect. Included in this embodiment are compounds of Formula (I) in which Ring A is phenyl. Also included in this embodiment are compound in which Ring A is phenyl and $R_1$ is —CH₂CH₂CF₃.

One embodiment provides at least one compound of Formula (I) wherein $R_2$ is —CH₂CH₂CH₂CF₃ and $R_1$, $R_3$, Ring A, $R_a$, $R_b$, y, and z are defined in the first aspect. Included in this embodiment are compounds of Formula (I) in which Ring A is phenyl. Also included in this embodiment are compound in which Ring A is phenyl and $R_1$ is —CH₂CH₂CF₃.

One embodiment provides at least one compound of Formula (I) wherein $R_2$ is —CH₂CF₂CH₃ and $R_1$, $R_3$, Ring A, $R_a$, $R_b$, y, and z are defined in the first aspect. Included in this embodiment are compounds of Formula (I) in which Ring A is phenyl. Also included in this embodiment are compound in which Ring A is phenyl and $R_1$ is —CH₂CH₂CF₃.

One embodiment provides at least one compound of Formula (I) wherein $R_3$ is —CH₂CF₃, —CH₂CN, —CH₂(cyclopropyl); and $R_1$, $R_2$, Ring A, $R_a$, $R_b$, y, and z are defined in the first aspect. Included in this embodiment are compounds of Formula (I) in which Ring A is phenyl. Also included in this embodiment are compound in which Ring A is phenyl and $R_1$ is —CH₂CH₂CF₃.

One embodiment provides at least one compound of Formula (I) wherein $R_3$ is pyridinyl, chloropyridinyl, or tetrahydropyranyl; and $R_1$, $R_2$, Ring A, $R_a$, $R_b$, y, and z are defined in the first aspect. Included in this embodiment are compounds of Formula (I) in which Ring A is phenyl. Also included in this embodiment are compound in which Ring A is phenyl and $R_1$ is —CH₂CH₂CF₃.

One embodiment provides at least one compound of Formula (I) wherein: Ring A is phenyl, having the structure of Formula (II):

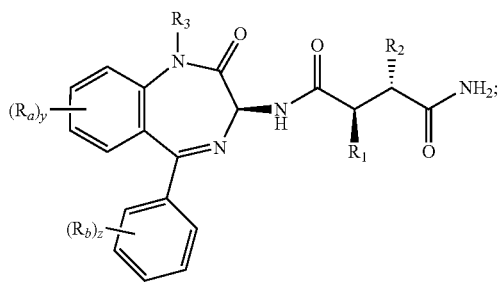

(II)

and wherein $R_1$, $R_2$, $R_3$, $R_a$, $R_b$, y, and z are defined in the first aspect.

One embodiment provides at least one compound of Formula (I) wherein: Ring A is pyridinyl; and $R_1$, $R_2$, $R_3$, $R_a$, $R_b$, y, and z are defined in the first aspect.

One embodiment provides at least one compound of Formula (I) wherein: Ring A is phenyl, $R_a$ is F, Cl, —CN, —CH₃, cyclopropyl, —CF₃, —OCH₃, —OCF₃, and/or —O(cyclopropyl); or two adjacent $R_a$ along with the carbon atoms to which they are attached form a dioxole ring; $R_b$ is independently F, Cl, —CH₃, —CF₃, —CN, and/or —OCH₃; y is zero or 1; z is zero or 1; and $R_1$, $R_2$, and $R_3$ are defined in the first aspect. Included in this embodiment are compounds in which $R_a$ is —OCH₃; $R_b$ is —OCH₃, y is zero or 1; and z is zero or 1.

One embodiment provides at least one compound of Formula (I) wherein: y is zero or 2; z is zero or 1; and $R_1$, $R_2$, $R_3$, Ring A, $R_a$, and $R_b$ are defined in the first aspect. Included in this embodiment are compounds in which Ring A is phenyl.

One embodiment provides at least one compound of Formula (I) wherein: $R_a$ is —OCH₃ or two adjacent $R_a$ along with the carbon atoms to which they are attached form a dioxole ring; $R_b$ is —OCH₃; y is zero, 1, or 2; z is zero or 1; and $R_1$, $R_2$, $R_3$, and Ring A are defined in the first aspect.

On embodiment provides at least one compound of Formula (I) having the structure

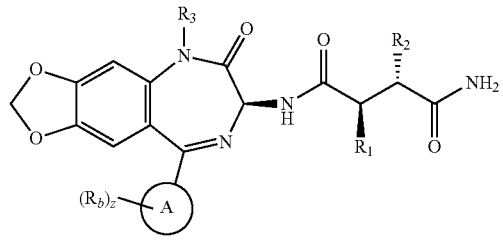

wherein $R_1$, $R_2$, $R_3$, Ring A, $R_b$, and z are defined in the first aspect. Included in the embodiment are compounds in which Ring A is phenyl. Also included in this embodiment are compounds in which Ring A is phenyl and z is zero or 1.

One embodiment provides a compound of Formula (I) selected from: (2R,3S)-N-((3S)-2-oxo-5-phenyl-1-(2-pyridinyl)-2,3-dihydro-1H-1,4-benzodiazepin-3-yl)-3-(4,4,4-trifluorobutyl)-2-(3,3,3-trifluoropropyl)succinamide (1); (2R,3S)-N-((3S)-1-(5-chloro-2-pyridinyl)-2-oxo-5-phenyl-2,3-dihydro-1H-1,4-benzodiazepin-3-yl)-2,3-bis(3,3,3-trifluoropropyl)succinamide (2); (2R,3S)-N-((7S)-6-oxo-9-phenyl-5-(2-pyridinyl)-6,7-dihydro-5H-[1,3]dioxolo[4,5-h][1,4]benzodiazepin-7-yl)-2,3-bis(3,3,3-trifluoropropyl)succinamide (3); (2R,3S)-N-((3S)-2-oxo-5-phenyl-1-(3-pyridinyl)-2,3-dihydro-1H-1,4-benzodiazepin-3-yl)-3-(4,4,4-trifluorobutyl)-2-(3,3,3-trifluoropropyl)succinamide (4); (2R,3S)-N-((3S)-2-oxo-5-phenyl-1-(3-pyridinyl)-2,3-dihydro-1H-1,4-benzodiazepin-3-yl)-2,3-bis(3,3,3-trifluoropropyl)succinamide (5); (2R,3S)-N-((3S)-1-(cyclopropylmethyl)-5-(4-methoxyphenyl)-2-oxo-2,3-dihydro-1H-1,4-benzodiazepin-3-yl)-2,3-bis(3,3,3-trifluoropropyl)succinamide (6); (2R,3S)-N-((3S)-7-methoxy-2-oxo-5-phenyl-1-(2,2,2-trifluoroethyl)-2,3-dihydro-1H-1,4-benzodiazepin-3-yl)-2,3-bis(3,3,3-trifluoropropyl)succinamide (7); (2R,3S)-N-((3S)-1-(cyclopropylmethyl)-2-oxo-5-phenyl-2,3-dihydro-1H-1,4-benzodiazepin-3-yl)-3-(2,2-difluoropropyl)-2-(3,3,3-trifluoropropyl)succinamide (8); and (2R,3S)-N-((3S)-1-(cyclopropylmethyl)-2-oxo-5- phenyl-2,3-dihydro-1H-1,4-benzodiazepin-3-yl)-2-(2,2-difluoropropyl)-3-(3,3,3-trifluoropropyl)succinamide (9).

One embodiment provides at least one compound of Formula (I) having a metabolic half life value of at least 45 minutes as measured in the human metabolic stability half-life assay described herein.

One embodiment provides at least one compound of Formula (I) having a metabolic half life value of at least 60 minutes as measured in the human metabolic stability half-life assay described herein.

The present invention may be embodied in other specific forms without departing from the spirit or essential attributes thereof. This invention encompasses all combinations of the aspects and/or embodiments of the invention noted herein. It is understood that any and all embodiments of the present invention may be taken in conjunction with any other embodiment or embodiments to describe addition more embodiments. It is also to be understood that each individual element of the embodiments is meant to be combined with any and all other elements from any embodiment to describe an additional embodiment.

DEFINITIONS

The features and advantages of the invention may be more readily understood by those of ordinary skill in the art upon reading the following detailed description. It is to be appreciated that certain features of the invention that are, for clarity reasons, described above and below in the context of separate embodiments, may also be combined to form a single embodiment. Conversely, various features of the invention that are, for brevity reasons, described in the context of a single embodiment, may also be combined so as to form sub-combinations thereof. Embodiments identified herein as exemplary or preferred are intended to be illustrative and not limiting.

Unless specifically stated otherwise herein, references made in the singular may also include the plural. For example, "a" and "an" may refer to either one, or one or more.

Unless otherwise indicated, any heteroatom with unsatisfied valences is assumed to have hydrogen atoms sufficient to satisfy the valences.

The definitions set forth herein take precedence over definitions set forth in any patent, patent application, and/or patent application publication incorporated herein by reference.

Listed below are definitions of various terms used to describe the present invention. These definitions apply to the terms as they are used throughout the specification (unless they are otherwise limited in specific instances) either individually or as part of a larger group.

Throughout the specification, groups and substituents thereof may be chosen by one skilled in the field to provide stable moieties and compounds.

The terms "halo" and "halogen", as used herein, refer to F, Cl, Br, or I.

The term "alkyl" as used herein, refers to both branched and straight chain saturated aliphatic hydrocarbon groups containing, for example, from 1 to 12 carbon atoms, from 1 to 6 carbon atoms, and from 1 to 4 carbon atoms. Examples of alkyl groups include, but are not limited to, methyl (Me), ethyl (Et), propyl (e.g., n-propyl and i-propyl), butyl (e.g., n-butyl, i-butyl, sec-butyl, and t-butyl), and pentyl (e.g., n-pentyl, isopentyl, neopentyl), n-hexyl, 2-methylpentyl, 2-ethylbutyl, 3-methylpentyl, and 4-methylpentyl. When numbers appear in a subscript after the symbol "C", the subscript defines with more specificity the number of carbon atoms that a particular group may contain. For example, "$C_{1-6}$ alkyl" denotes straight and branched chain alkyl groups with one to six carbon atoms.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The compounds of Formula (I) can be provided as amorphous solids or crystalline solids. Lyophilization can be employed to provide the compounds of Formula (I) as a solid.

It should further be understood that solvates (e.g., hydrates) of the Compounds of Formula (I) are also within the scope of the present invention. The term "solvate" means a physical association of a compound of Formula (I) with one or more solvent molecules, whether organic or inorganic. This physical association includes hydrogen bonding. In certain instances the solvate will be capable of isolation, for example when one or more solvent molecules are incorporated in the crystal lattice of the crystalline solid. "Solvate" encompasses both solution-phase and isolable solvates. Exemplary solvates include hydrates, ethanolates, methanolates, isopropanolates, acetonitrile solvates, and ethyl acetate solvates. Methods of solvation are known in the art.

Any compound that can be converted in vivo to provide the bioactive agent (i.e., the compound of Formula (I)) is a prodrug within the scope and spirit of the invention.

Various forms of prodrugs are well known in the art and are described in:

a) Wermuth, C. G. et al., *The Practice of Medicinal Chemistry*, Chapter 31, Academic Press (1996);

b) Bundgaard, H. ed., *Design of Prodrugs*, Elsevier (1985);

c) Bundgaard, H., Chapter 5, "Design and Application of Prodrugs", Krogsgaard-Larsen, P. et al., eds., *A Textbook of Drug Design and Development*, pp. 113-191, Harwood Academic Publishers (1991); and d) Testa, B. et al., *Hydrolysis in Drug and Prodrug Metabolism*, Wiley-VCH (2003).

In addition, compounds of Formula (I), subsequent to their preparation, can be isolated and purified to obtain a composition containing an amount by weight equal to or greater than 99% of a compound of Formula (I) ("substantially pure"), which is then used or formulated as described herein. Such "substantially pure" compounds of Formula (I) are also contemplated herein as part of the present invention.

"Stable compound" and "stable structure" are meant to indicate a compound that is sufficiently robust to survive isolation to a useful degree of purity from a reaction mixture, and formulation into an efficacious therapeutic agent. The present invention is intended to embody stable compounds.

"Therapeutically effective amount" is intended to include an amount of a compound of the present invention alone or an amount of the combination of compounds claimed or an amount of a compound of the present invention in combination with other active ingredients effective to act as an inhibitor to a NOTCH receptor, or effective to treat or prevent proliferative diseases such as cancer.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting its development; and/or (c) relieving the disease-state, i.e., causing regression of the disease state.

The compounds of the present invention are intended to include all isotopes of atoms occurring in the present compounds. Isotopes include those atoms having the same atomic number but different mass numbers. By way of general example and without limitation, isotopes of hydrogen include deuterium (D) and tritium (T). Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed.

Compounds in accordance with Formula (I) can be administered by any means suitable for the condition to be treated, which can depend on the need for site-specific treatment or quantity of Formula (I) compound to be delivered.

Also embraced within this invention is a class of pharmaceutical compositions comprising at least one compound of Formula (I) thereof; and one or more non-toxic, pharmaceutically-acceptable carriers and/or diluents and/or adjuvants (collectively referred to herein as "carrier" materials) and, if desired, other active ingredients. The compounds of Formula (I) may be administered by any suitable route, preferably in the form of a pharmaceutical composition adapted to such a route, and in a dose effective for the treatment intended. The compounds and compositions of the present invention may, for example, be administered orally, mucosally, or parentally including intravascularly, intravenously, intraperitoneally, subcutaneously, intramuscularly, and intrasternally in dosage unit formulations containing conventional pharmaceutically acceptable carriers, adjuvants, and vehicles. For example, the pharmaceutical carrier may contain a mixture of mannitol or lactose and microcrystalline cellulose. The mixture may contain additional components such as a lubricating agent, e.g., magnesium stearate and a disintegrating agent such as crospovidone. The carrier mixture may be filled into a gelatin capsule or compressed as a tablet. The pharmaceutical composition may be administered as an oral dosage form or an infusion, for example.

For oral administration, the pharmaceutical composition may be in the form of, for example, a tablet, capsule, liquid capsule, suspension, or liquid. The pharmaceutical composition is preferably made in the form of a dosage unit containing a particular amount of the active ingredient. For example, the pharmaceutical composition may be provided as a tablet or capsule comprising an amount of active ingredient in the range of from about 1 to 2000 mg, preferably from about 1 to 500 mg, and more preferably from about 5 to 150 mg. A suitable daily dose for a human or other mammal may vary widely depending on the condition of the patient and other factors, but, can be determined using routine methods.

Any pharmaceutical composition contemplated herein can, for example, be delivered orally via any acceptable and suitable oral preparations. Exemplary oral preparations, include, but are not limited to, for example, tablets, troches, lozenges, aqueous and oily suspensions, liquid capsules, dispersible powders or granules, emulsions, hard and soft capsules, syrups, and elixirs. Pharmaceutical compositions intended for oral administration can be prepared according to any methods known in the art for manufacturing pharmaceutical compositions intended for oral administration. In order to provide pharmaceutically palatable preparations, a pharmaceutical composition in accordance with the invention can contain at least one agent selected from sweetening agents, flavoring agents, coloring agents, demulcents, antioxidants, and preserving agents.

A tablet can, for example, be prepared by admixing at least one compound of Formula (I) with at least one non-toxic pharmaceutically acceptable excipient suitable for the manufacture of tablets. Exemplary excipients include, but are not limited to, for example, inert diluents, such as, for example, calcium carbonate, sodium carbonate, lactose, calcium phosphate, and sodium phosphate; granulating and disintegrating agents, such as, for example, microcrystalline cellulose, sodium croscarmellose, corn starch, and alginic acid; binding agents, such as, for example, starch, gelatin, polyvinyl-pyrrolidone, and acacia; and lubricating agents, such as, for example, magnesium stearate, stearic acid, and talc. Additionally, a tablet can either be uncoated, or coated by known techniques to either mask the bad taste of an unpleasant tasting drug, or delay disintegration and absorption of the active ingredient in the gastrointestinal tract thereby sustaining the effects of the active ingredient for a longer period. Exemplary water soluble taste masking materials, include, but are not limited to, hydroxypropyl-methylcellulose and hydroxypropyl-cellulose. Exemplary time delay materials, include, but are not limited to, ethyl cellulose and cellulose acetate butyrate.

Hard gelatin capsules can, for example, be prepared by mixing at least one compound of Formula (I) with at least one inert solid diluent, such as, for example, calcium carbonate; calcium phosphate; and kaolin.

Soft gelatin capsules can, for example, be prepared by mixing at least one compound of Formula (I) with at least one water soluble carrier, such as, for example, polyethylene glycol; and at least one oil medium, such as, for example, peanut oil, liquid paraffin, and olive oil.

An aqueous suspension can be prepared, for example, by admixing at least one compound of Formula (I) with at least one excipient suitable for the manufacture of an aqueous suspension. Exemplary excipients suitable for the manufacture of an aqueous suspension, include, but are not limited to, for example, suspending agents, such as, for example, sodium carboxymethylcellulose, methylcellulose, hydroxypropylmethyl-cellulose, sodium alginate, alginic acid, polyvinyl-pyrrolidone, gum tragacanth, and gum acacia; dispersing or wetting agents, such as, for example, a naturally-occurring phosphatide, e.g., lecithin; condensation products of alkylene oxide with fatty acids, such as, for example, polyoxyethylene stearate; condensation products of ethylene oxide with long chain aliphatic alcohols, such as, for example heptadecaethylene-oxycetanol; condensation products of ethylene oxide with partial esters derived from fatty acids and hexitol, such as, for example, polyoxyethylene sorbitol monooleate; and condensation products of ethylene oxide with partial esters derived from fatty acids and hexitol anhydrides, such as, for example, polyethylene sorbitan monooleate. An aqueous suspension can also contain at least one preservative, such as, for example, ethyl and n-propyl p-hydroxybenzoate; at least one coloring agent; at least one flavoring agent; and/or at least one sweetening agent, including but not limited to, for example, sucrose, saccharin, and aspartame.

Oily suspensions can, for example, be prepared by suspending at least one compound of Formula (I) in either a vegetable oil, such as, for example, arachis oil; olive oil; sesame oil; and coconut oil; or in mineral oil, such as, for example, liquid paraffin. An oily suspension can also contain at least one thickening agent, such as, for example, beeswax; hard paraffin; and cetyl alcohol. In order to provide a palatable oily suspension, at least one of the sweetening agents already described hereinabove, and/or at least one flavoring agent can be added to the oily suspension. An oily suspension can further contain at least one preservative, including, but not limited to, for example, an anti-oxidant, such as, for example, butylated hydroxyanisol, and alpha-tocopherol.

Dispersible powders and granules can, for example, be prepared by admixing at least one compound of Formula (I) with at least one dispersing and/or wetting agent; at least one suspending agent; and/or at least one preservative. Suitable dispersing agents, wetting agents, and suspending agents are as already described above. Exemplary preservatives include, but are not limited to, for example, anti-oxidants, e.g., ascorbic acid. In addition, dispersible powders and granules can also contain at least one excipient, including, but not limited to, for example, sweetening agents; flavoring agents; and coloring agents.

An emulsion of at least one compound of Formula (I) can, for example, be prepared as an oil-in-water emulsion. The oily phase of the emulsions comprising compounds of Formula (I) may be constituted from known ingredients in a known manner. The oil phase can be provided by, but is not limited to, for example, a vegetable oil, such as, for example, olive oil and arachis oil; a mineral oil, such as, for example, liquid paraffin; and mixtures thereof. While the phase may comprise merely an emulsifier, it may comprise a mixture of at least one emulsifier with a fat or an oil or with both a fat and an oil. Suitable emulsifying agents include, but are not limited to, for example, naturally-occurring phosphatides, e.g., soy bean lecithin; esters or partial esters derived from fatty acids and hexitol anhydrides, such as, for example, sorbitan monooleate; and condensation products of partial esters with ethylene oxide, such as, for example, polyoxyethylene sorbitan monooleate. Preferably, a hydrophilic emulsifier is included together with a lipophilic emulsifier which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base which forms the oily dispersed phase of the cream formulations. An emulsion can also contain a sweetening agent, a flavoring agent, a preservative, and/or an antioxidant. Emulsifiers and emulsion stabilizers suitable for use in the formulation of the present invention include Tween 60, Span 80, cetostearyl alcohol, myristyl alcohol, glyceryl monostearate, sodium lauryl sulfate, glyceryl distearate alone or with a wax, or other materials well known in the art.

The compounds of Formula (I) can, for example, also be delivered intravenously, subcutaneously, and/or intramuscularly via any pharmaceutically acceptable and suitable injectable form. Exemplary injectable forms include, but are not limited to, for example, sterile aqueous solutions comprising acceptable vehicles and solvents, such as, for example, water, Ringer's solution, and isotonic sodium chloride solution; sterile oil-in-water microemulsions; and aqueous or oleaginous suspensions.

Formulations for parenteral administration may be in the form of aqueous or non-aqueous isotonic sterile injection solutions or suspensions. These solutions and suspensions may be prepared from sterile powders or granules using one or more of the carriers or diluents mentioned for use in the formulations for oral administration or by using other suitable dispersing or wetting agents and suspending agents. The compounds may be dissolved in water, polyethylene glycol, propylene glycol, ethanol, corn oil, cottonseed oil, peanut oil, sesame oil, benzyl alcohol, sodium chloride, tragacanth gum, and/or various buffers. Other adjuvants and modes of administration are well and widely known in the pharmaceutical art. The active ingredient may also be administered by injection as a composition with suitable carriers including saline, dextrose, or water, or with cyclodextrin (i.e., CAPTISOL®), cosolvent solubilization (i.e., propylene glycol) or micellar solubilization (i.e., Tween 80).

The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

A sterile injectable oil-in-water microemulsion can, for example, be prepared by 1) dissolving at least one compound of Formula (I) in an oily phase, such as, for example, a mixture of soybean oil and lecithin; 2) combining the Formula (I) containing oil phase with a water and glycerol mixture; and 3) processing the combination to form a microemulsion.

A sterile aqueous or oleaginous suspension can be prepared in accordance with methods already known in the art. For example, a sterile aqueous solution or suspension can be prepared with a non-toxic parenterally-acceptable diluent or solvent, such as, for example, 1,3-butane diol; and a sterile oleaginous suspension can be prepared with a sterile non-toxic acceptable solvent or suspending medium, such as, for example, sterile fixed oils, e.g., synthetic mono- or diglycerides; and fatty acids, such as, for example, oleic acid.

Pharmaceutically acceptable carriers, adjuvants, and vehicles that may be used in the pharmaceutical compositions of this invention include, but are not limited to, ion exchangers, alumina, aluminum stearate, lecithin, self-emulsifying drug delivery systems (SEDDS) such as d-alpha-tocopherol polyethyleneglycol 1000 succinate, surfactants used in pharmaceutical dosage forms such as Tweens, polyethoxylated castor oil such as CREMOPHOR® surfactant (BASF), or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as alpha-, beta-, and gamma-cyclodextrin, or chemically modified derivatives such as hydroxyalkylcyclodextrins, including 2- and 3-hydroxypropyl-cyclodextrins, or other solubilized derivatives may also be advantageously used to enhance delivery of compounds of the formulae described herein.

The pharmaceutically active compounds of this invention can be processed in accordance with conventional methods of pharmacy to produce medicinal agents for administration to patients, including humans and other mammals. The pharmaceutical compositions may be subjected to conventional pharmaceutical operations such as sterilization and/or may contain conventional adjuvants, such as preservatives, stabilizers, wetting agents, emulsifiers, buffers etc. Tablets and pills can additionally be prepared with enteric coatings. Such compositions may also comprise adjuvants, such as wetting, sweetening, flavoring, and perfuming agents.

The amounts of compounds that are administered and the dosage regimen for treating a disease condition with the compounds and/or compositions of this invention depends on a variety of factors, including the age, weight, sex, the medical condition of the subject, the type of disease, the severity of the disease, the route and frequency of administration, and the particular compound employed. Thus, the dosage regimen may vary widely, but can be determined routinely using standard methods. A daily dose of about 0.001 to 100 mg/kg body weight, preferably between about 0.005 and about 50 mg/kg body weight and most preferably between about 0.01 to 10 mg/kg body weight, may be appropriate. The daily dose can be administered in one to four doses per day.

For therapeutic purposes, the active compounds of this invention are ordinarily combined with one or more adjuvants appropriate to the indicated route of administration. If administered orally, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose.

Pharmaceutical compositions of this invention comprise the compound of Formula (I) and optionally an additional agent selected from any pharmaceutically acceptable carrier, adjuvant, and vehicle. Alternate compositions of this invention comprise a compound of the Formula (I) described herein and a pharmaceutically acceptable carrier, adjuvant, or vehicle.

UTILITY

The compounds of Formula (I) are useful for the treatment of cancer, for example, cancers dependent upon Notch activation. Notch activation has been implicated in the pathogenesis of various solid tumors including ovarian, pancreatic, as well as breast cancer and hematologic tumors such as leukemias, lymphomas, and multiple myeloma.

In one embodiment, a method is provided for treating cancer comprising administering to a mammal in need thereof a compound of Formula (I). The method of this embodiment can be used to treat a variety of cancers, including, but not limited to, bladder cancer, breast cancer, colorectal cancer, gastric cancer, head and neck cancer, kidney cancer, liver cancer, lung cancer including non-small cell lung cancer (NSCLC), ovarian cancer, pancreatic cancer, gall bladder cancer, prostate cancer, thyroid cancer, osteosarcoma, rhabdomyosarcoma, malignant fibrous histiocytoma (MFH), fibrosarcoma, glioblastomas/astrocytomas, neuroblastoma, melanoma, T-cell acute lymphoblastic leukemia (T-ALL), and mesothelioma. For example, the method of this embodiment is used to treat breast cancer, colon cancer, or pancreatic cancer. Preferably, the mammal is a human. For example, a therapeutically effective amount for treating cancer may be administered in the method of the present embodiment. Routes of administration in the present embodiment include parenteral administration and oral administration.

In one embodiment, a method is provided for treating cancer comprising administering to a mammal in need thereof at least one compound of Formula (I), wherein said cancer is colorectal cancer. Preferably, the mammal is a human. For example, a therapeutically effective amount for treating cancer may be administered in the method of the present embodiment. Routes of administration in the present embodiment include parenteral administration and oral administration.

In one embodiment, a method is provided for treating cancer comprising administering to a mammal in need thereof at least one compound of Formula (I), wherein said cancer is triple negative breast cancer. Preferably, the mammal is a human. For example, a therapeutically effective amount for treating cancer may be administered in the method of the present embodiment. Routes of administration in the present embodiment include parenteral administration and oral administration.

In one embodiment, a method is provided for treating cancer comprising administering to a mammal in need thereof at least one compound of Formula (I), wherein said cancer is non-small cell lung cancer. Preferably, the mammal is a human. For example, a therapeutically effective amount for treating cancer may be administered in the method of the present embodiment. Routes of administration in the present embodiment include parenteral administration and oral administration.

In one embodiment, a method is provided for treating cancer comprising administering to a mammal in need thereof at least one compound of Formula (I), wherein said cancer is pancreatic cancer. Preferably, the mammal is a human. For example, a therapeutically effective amount for treating cancer may be administered in the method of the present embodiment. Routes of administration in the present embodiment include parenteral administration and oral administration.

In one embodiment, a method is provided for treating cancer comprising administering to a mammal in need thereof at least one compound of Formula (I), wherein said cancer is ovarian cancer. Preferably, the mammal is a human. For example, a therapeutically effective amount for treating cancer may be administered in the method of the present embodiment. Routes of administration in the present embodiment include parenteral administration and oral administration.

In one embodiment, a method is provided for treating cancer comprising administering to a mammal in need thereof at least one compound of Formula (I), wherein said cancer is melanoma. Preferably, the mammal is a human. For example, a therapeutically effective amount for treating cancer may be administered in the method of the present embodiment. Routes of administration in the present embodiment include parenteral administration and oral administration.

In one embodiment, the use of at least one compound of Formula (I) in the manufacture of a medicament for the treatment of cancer is provided. Preferably, in the present embodiment, cancers subject to treatment include one or more of bladder cancer, breast cancer, colorectal cancer, gastric cancer, head and neck cancer, kidney cancer, liver cancer, lung cancer including non-small cell lung cancer (NSCLC), ovarian cancer, pancreatic cancer, gall bladder cancer, prostate cancer, thyroid cancer, osteosarcoma, rhabdomyosarcoma, malignant fibrous histiocytoma (MFH), fibrosarcoma, glioblastomas/astrocytomas, neuroblastoma, melanoma, T-cell acute lymphoblastic leukemia (T-ALL), and mesothelioma. Suitable medicaments of the present embodiment include medicaments for parenteral administration, such as, for example, solutions and suspensions and medicaments for oral administration, such as, for example, tablets, capsules, solutions, and suspensions.

One embodiment at least one compound of Formula (I) for use in therapy in treating cancer. In the present embodiment, cancers subject to treatment include one or more of bladder cancer, breast cancer, colorectal cancer, gastric cancer, head and neck cancer, kidney cancer, liver cancer, lung cancer including non-small cell lung cancer (NSCLC), ovarian cancer, pancreatic cancer, gall bladder cancer, prostate cancer, thyroid cancer, osteosarcoma, rhabdomyosarcoma, malignant fibrous histiocytoma (MFH), fibrosarcoma, glioblastomas/astrocytomas, neuroblastoma, melanoma, T-cell acute lymphoblastic leukemia (T-ALL), and mesothelioma.

In one embodiment, a method is provided for treating cancer in a mammal wherein the cancer is dependent upon Notch activation, comprising administering to the patient at least one compound of Formula (I). The method of this embodiment can be used to treat a variety of cancers, including, but not limited to, bladder cancer, breast cancer, colorectal cancer, gastric cancer, head and neck cancer, kidney cancer, liver cancer, lung cancer including non-small cell lung cancer (NSCLC), ovarian cancer, pancreatic cancer, gall bladder cancer, prostate cancer, thyroid cancer, osteosarcoma, rhabdomyosarcoma, malignant fibrous histiocytoma (MFH), fibrosarcoma, glioblastomas/astrocytomas, neuroblastoma, melanoma, T-cell acute lymphoblastic leukemia (T-ALL), and mesothelioma. Preferably, the method of this embodiment is used to treat breast cancer, colon cancer, or pancreatic cancer. Preferably, the mammal is a human. For example, a therapeutically effective amount for treating cancer may be administered in the method of the present embodiment. Suitable routes of administration include parenteral administration and oral administration.

In treating cancer, a combination of chemotherapeutic agents and/or other treatments (e.g., radiation therapy) is often advantageous. The second (or third) agent may have the same or different mechanism of action than the primary therapeutic agent. For example, drug combinations may be employed wherein the two or more drugs being administered act in different manners or in different phases of the cell cycle, and/or where the two or more drugs have nonoverlapping toxicities or side effects, and/or where the drugs being combined each has a demonstrated efficacy in treating the particular disease state manifested by the patient.

In one embodiment, a method is provided for treating cancer comprising administering to a mammal in need thereof at least one compound of Formula (I); and administering one or more additional anticancer agents.

The phrase "additional anticancer agent" refers to a drug selected from any one or more of the following: alkylating agents (including nitrogen mustards, alkyl sulfonates, nitrosoureas, ethylenimine derivatives, and triazenes); antiangiogenics (including matrix metalloproteinase inhibitors); antimetabolites (including adenosine deaminase inhibitors, folic acid antagonists, purine analogues, and pyrimidine analogues); antibiotics or antibodies (including monoclonal antibodies, CTLA-4 antibodies, anthracyclines); aromatase inhibitors; cell-cycle response modifiers; enzymes; farnesyl-protein transferase inhibitors; hormonal and antihormonal agents and steroids (including synthetic analogs, glucocorticoids, estrogens/anti-estrogens [e.g., SERMs], androgens/anti-androgens, progestins, progesterone receptor agonists, and luteinizing hormone-releasing [LHRH] agonists and antagonists); insulin-like growth factor (IGF)/insulin-like growth factor receptor (IGFR) system modulators (including IGFR1 inhibitors); integrin-signaling inhibitors; kinase inhibitors (including multi-kinase inhibitors and/or inhibitors of Src kinase or Src/abl, cyclin dependent kinase [CDK] inhibitors, panHer, Her-1 and Her-2 antibodies, VEGF inhibitors, including anti-VEGF antibodies, EGFR inhibitors, mitogen-activated protein [MAP] inhibitors, MET inhibitors, MEK inhibitors, Aurora kinase inhibitors, PDGF inhibitors, and other tyrosine kinase inhibitors or serine/threonine kinase inhibitors; microtubule-disruptor agents, such as ecteinascidins or their analogs and derivatives; microtubule-stabilizing agents such as taxanes, and the naturally-occurring epothilones and their synthetic and semi-synthetic analogs; microtubule-binding, destabilizing agents (including vinca alkaloids); topoisomerase inhibitors; prenyl-protein transferase inhibitors; platinum coordination complexes; signal transduction inhibitors; and other agents used as anti-cancer and cytotoxic agents such as biological response modifiers, growth factors, and immune modulators.

Accordingly, the compounds of the present invention may be administered in combination with other anti-cancer treatments useful in the treatment of cancer or other proliferative diseases. The invention herein further comprises use of at least one compound of Formula (I) in preparing medicaments for the treatment of cancer, and/or it comprises the packaging of a compound of Formula (I) herein together with instructions that the compound be used in combination with other anti-cancer or cytotoxic agents and treatments for the treatment of cancer. The present invention further comprises combinations of at least one compound of Formula (I); and one or more additional agents in kit form, e.g., where they are packaged together or placed in separate packages to be sold together as a kit, or where they are packaged to be formulated together.

In one embodiment, a method is provided for treating cancer comprising administering to a mammal in need thereof at least one compound of Formula (I); administering dasatinib; and optionally, one or more additional anticancer agents.

In one embodiment, a method is provided for treating cancer comprising administering to a mammal in need thereof at least one compound of Formula (I); administering paclitaxel; and optionally, one or more additional anticancer agents.

In one embodiment, a method is provided for treating cancer comprising administering to a mammal in need thereof at least one compound of Formula (I); administering tamoxifen; and optionally, one or more additional anticancer agents.

In one embodiment, a method is provided for treating cancer comprising administering to a mammal in need thereof at least one compound of Formula (I); administering a glucocorticoid; and optionally, one or more additional anticancer agents. An example of a suitable glucocorticoid is dexamethasone.

In one embodiment, a method is provided for treating cancer comprising administering to a mammal in need thereof at least one compound of Formula (I); administering carboplatin; and optionally, one or more additional anticancer agents.

The compounds of the present invention can be formulated or co-administered with other therapeutic agents that are selected for their particular usefulness in addressing side effects associated with the aforementioned conditions. For example, compounds of the invention may be formulated with agents to prevent nausea, hypersensitivity and gastric irritation, such as antiemetics, and $H_1$ and $H_2$ antihistaminics.

In one embodiment, pharmaceutical compositions are provided comprising at least one compound of Formula (I); one or more additional agents selected from a kinase inhibitory agent (small molecule, polypeptide, and antibody), an immunosuppressant, an anticancer agent, an anti-viral agent, anti-inflammatory agent, antifungal agent, antibiotic, or an anti-vascular hyperproliferation compound; and any pharmaceutically acceptable carrier, adjuvant or vehicle.

The above other therapeutic agents, when employed in combination with the compounds of the present invention, may be used, for example, in those amounts indicated in the *Physicians' Desk Reference* (PDR) or as otherwise determined by one of ordinary skill in the art. In the methods of the present invention, such other therapeutic agent(s) may be administered prior to, simultaneously with, or following the administration of the inventive compounds.

The specific dose level and frequency of dosage for any particular subject however, may be varied and generally depends on a variety of factors, including, but not limited to, for example, the bioavailability of the specific compound of Formula (I) in the administered form, metabolic stability and length of action of the specific compound of Formula (I), species, body weight, general health, sex, diet of subject, mode and time of administration, rate of excretion, drug combination, and severity of the particular condition. For example, a daily dose of about 0.001 to 100 mg/kg body weight, preferably between about 0.005 and about 50 mg/kg body weight and most preferably between about 0.01 to 10 mg/kg body weight, may be appropriate. The daily dose can be administered in one to four doses per day.

The administration can be continuous, i.e., every day, or intermittently. The terms "intermittent" or "intermittently" as used herein mean stopping and starting at either regular or irregular intervals. For example, intermittent administration includes administration one to six days per week; administration in cycles (e.g., daily administration for two to eight consecutive weeks followed by a rest period with no administration for up to one week); or administration on alternate days.

In one embodiment, the at least one compound of Formula (I) are administered continuously to a patient in need thereof, one or more times daily. For example, a therapeutically effective amount of the compound of Formula (I) is administered to a patient in need thereof, one or more times daily for continuous days.

In one embodiment, the at least one compound of Formula (I) is administered intermittently to a patient in need thereof, one or more times daily. For example, a therapeutically effective amount of the compound of Formula (I) is administered to a patient in need thereof, one or more times daily according to an intermittent schedule.

In one embodiment, the at least one compound of Formula (I) administered to a patient in need thereof, one or more times daily for continuous days followed by one or more days without administration. Preferably, a therapeutically effective amount of the compound of Formula (I) is administered. Examples of continuous dosing with a drug holiday are cycles of: 7 days on treatment followed by 7 days off treatment; 14 days on treatment followed by 7 days off treatment; and 7 days on treatment followed by 14 days off treatment. A cycle of on treatment/off treatment can be repeated multiple times as required to treat a patient.

In one embodiment, the at least one compound of Formula (I) is administered to a patient in need thereof, according to an intermittent dosing schedule. Intermittent dosing schedules are repeating schedules including days in which the patient is administered the compound of Formula (I) and days in which the patient is not administered the compound of Formula (I). Examples of intermittent dosing schedules are: dosing four days each week for three continuous weeks followed by a week without dosing, and repeating on a four week interval; dosing five days each week for two continuous weeks followed by a week without dosing, and repeating on a three week interval; and dosing four days each week for one week followed by two weeks without dosing, and repeating on a three week interval. Preferably, a therapeutically effective amount of the compound of Formula (I) is administered.

In one embodiment, at least one compound of Formula (I) is administered on one day, followed by 6 days of rest, and repeated on a weekly schedule.

In one embodiment, at least one compound of Formula (I) is administered on one day, followed by 6 days of rest, and repeated on a weekly schedule for 1 to 4 weeks, and then followed by one week or rest. For example, the compound of Formula (I) is administered on one day, followed by 6 days of rest for three weeks, and then followed by one week of rest. This four week cycle can be repeated one or more times.

In one embodiment, at least one compound of Formula (I) is administered on two consecutive days, followed by 5 days of rest, and repeated on a weekly schedule.

In one embodiment, at least one compound of Formula (I) is administered on three consecutive days followed by four days of rest, and repeated on a weekly schedule.

In one embodiment, at least one compound of Formula (I) is administered on one day, followed by 10 to 13 days of rest.

In one embodiment, at least one compound of Formula (I) is administered once each day (QD). This embodiment includes once daily oral administration.

In one embodiment, at least one compound of Formula (I) is administered twice each day (BID). This embodiment includes twice daily oral administration.

In one embodiment, at least one compound of Formula (I) is administered on alternate days: one day on followed by one day of rest. This two day cycle can be repeated one or more times.

METHODS OF PREPARATION

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Preferred methods include, but are not limited to, those described below. All references cited herein are hereby incorporated in their entirety by reference.

The compounds of this invention may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including choice of solvent, reaction atmosphere, reaction temperature, duration of the experiment and work up procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents that are compatible with the reaction conditions will be readily apparent to one skilled in the art and alternate methods must then be used. This will sometimes require a judgment to modify the order of the synthetic steps or to select one particular process scheme over another in order to obtain a desired compound of the invention. It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene et al. (*Protective Groups in Organic Synthesis*, Third Edition, Wiley and Sons (1999)).

Compounds of Formula (I) may be prepared by reference to the methods illustrated in the following Schemes. As shown therein the end product is a compound having the same structural formula as Formula (I). It will be understood that any compound of Formula (I) may be produced by the schemes by the suitable selection of reagents with appropriate substitution. Solvents, temperatures, pressures, and other reaction conditions may readily be selected by one of ordinary skill in the art. Starting materials are commercially available or readily prepared by one of ordinary skill in the art. Constituents of compounds are as defined herein or elsewhere in the specification.

The synthesis of the compounds of Formula (I) can be made using the methods summarized in Schemes 1 to 4.

Step 2: The deprotection of (iii) may be accomplished in several ways known to one skilled in the art. For example, with PG=CBz, Compound (iii) may be treated with a reagent such as HBr in a solvent such as AcOH. Compound (iv) may be used as a racemate. Alternatively, compound (iv) may be subjected to enantiomeric resolution using standard methods (e.g., chiral preparative chromatography).

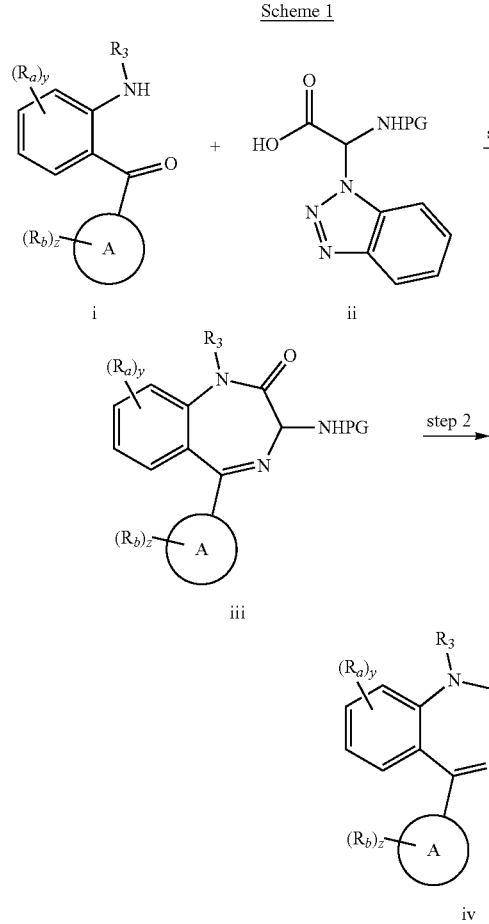

The preparation of benzodiazepinone (iv) may be accomplished in multitude of methods known to one skilled in the art. For example, as shown in Scheme 1, an appropriately substituted 2-aminobenzophenone (i) (for example, from Walsh, D. A., *Synthesis*, 677 (1980); and references cited therein, or other methods known to one skilled in the art) may be coupled to the protected glycine derivative (ii) (PG=protecting group, for example PG=CBz, see Katritzky, A. R. et al., *J. Org. Chem.*, 55:2206-2214 (1990)), treated with a reagent such as ammonia and subjected to cyclization to afford the benzodiazepinone (iii), according to the procedure outlined in the literature (for example Sherrill, R. G. et al., *J. Org. Chem.*, 60:730 (1995); or other routes known to one skilled in the art). The resulting racemic mixture may be separated (using procedures known to one skilled in the art) to afford the individual enantiomers, or used as a racemate. Also, if $R_3$ is H, (iii) may be, for example, treated with an aryl or alkyl halide in the presence of a base such as $K_2CO_3$ or $Cs_2CO_3$ in a solvent such as DMF to provide other $R_3$ substitutions.

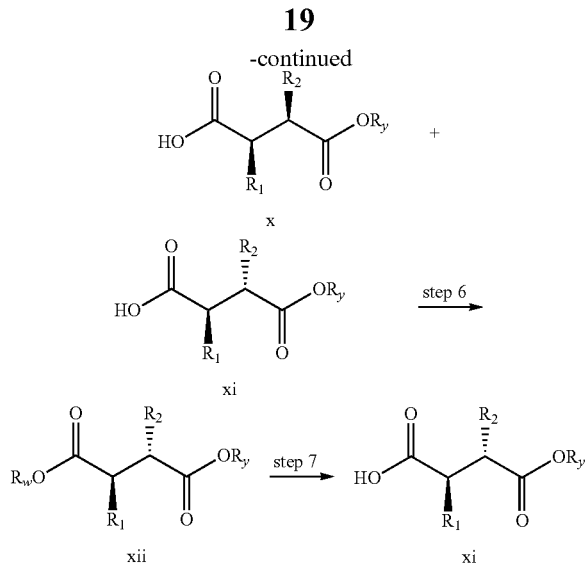

Compound (xii) in may be prepared by a synthetic sequence outlined in Scheme 2.

Step 1: Acid (v) can be converted to compound (vii) in multiple ways known to one skilled in the art. For example, treatment of acid (v) with a reagent such as oxalyl chloride in a solvent such as DCM gives the acid chloride (vi). Compound (vi) can be treated with an oxazolidinone (a) under standard conditions to give compound (vii) (Evans, D. A. et al., *J. Am. Chem. Soc.*, 112:4011 (1990)).

Step 2: The second step of Scheme 2 is accomplished by treating compound (vii) with a base such as sodium bis(trimethylsilyl)-amide or lithium diisopropyl amide in a solvent such as THF at low temperature such as −78° C. under an inert atmosphere. The resulting enolate of (vii) is treated with a reagent such as tert-butyl bromoacetate to provide compound (viii, $R_y$=t-Butyl).

Step 3: Conversion of compound (viii) to (ix) may be accomplished by treating compound (viii) with hydrogen peroxide and lithium hydroxide at an appropriate temperature using a mixture of solvents such as THF/water.

Step 4: Compound (ix) can be converted to a mixture of compound (x) and compound (xi) by generating the enolate of (ix) with a base such as LDA in a solvent such as THF at low temperature such as −78° C. under an inert atmosphere and further treatment with a reagent ($R_2$-LG) bearing an appropriate leaving group (e.g., LG=triflate). The resulting mixture of diastereomers (x/xi) may then be utilized in subsequent synthetic steps.

Step 5: Alternately, the mixture (x/xi) may be subjected to epimerization conditions, for example by treatment with LDA and diethylaluminum chloride followed by quenching with methanol or acetic acid to enrich the desired diastereomer. The resulting diastereomerically enriched mixture of compound (x/xi) may then be utilized in subsequent synthetic steps or the mixture of diastereoisomers may be separated if desired, employing suitable conditions such as preparative HPLC, preparative chiral HPLC or silica gel chromatography, and the resulting pure desired diastereoisomer (xi) used in the subsequent steps.

Step 6: Alternatively, the mixture of diastereomeric acids (x) and (xi) may be protected by treatment with, for example, benzyl bromide in the presence of a base such as $K_2CO_3$ in a solvent such as DMF. The resulting mixture of diastereoisomers may be separated if desired, employing suitable conditions such as preparative HPLC, preparative chiral HPLC or silica gel chromatography, and the resulting pure desired diastereoisomer compound (xii) used in the subsequent step.

Step 7: The last step of Scheme 2 is a deprotection step and may be accomplished in several ways known to one skilled in the art. For example, for $R_w$=benzyl in compound (xii), treatment under hydrogenation conditions using a catalyst such as palladium on carbon in a solvent such as MeOH under a hydrogen atmosphere may provide compound (xi) that may subsequently be utilized.

Alternatively, compound (xi) may be prepared according to the sequence of steps found in Scheme 3.

Scheme 3

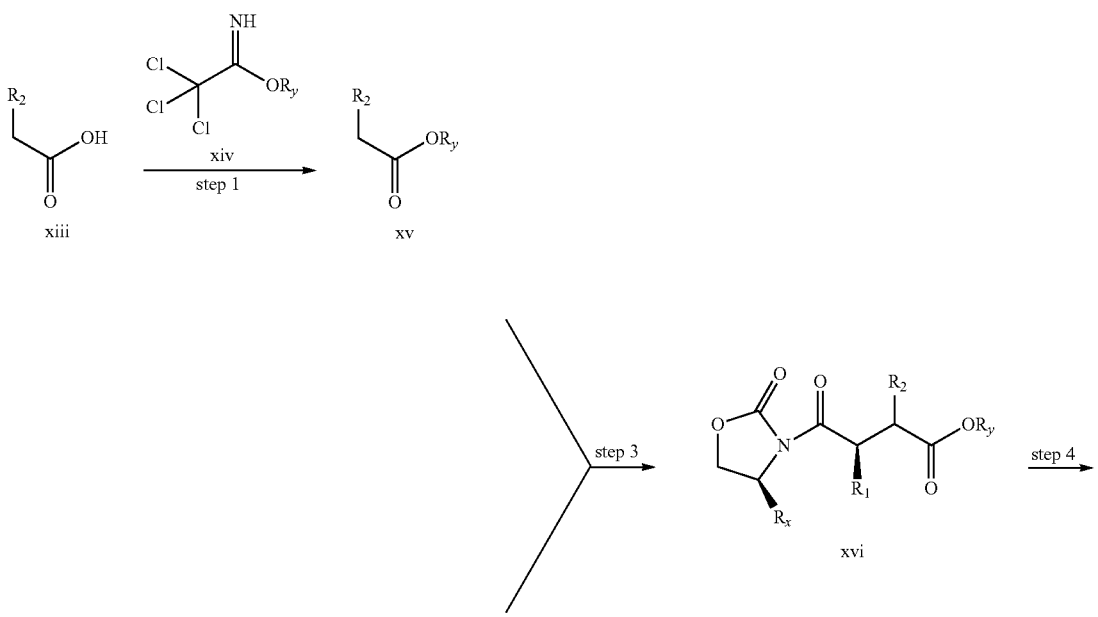

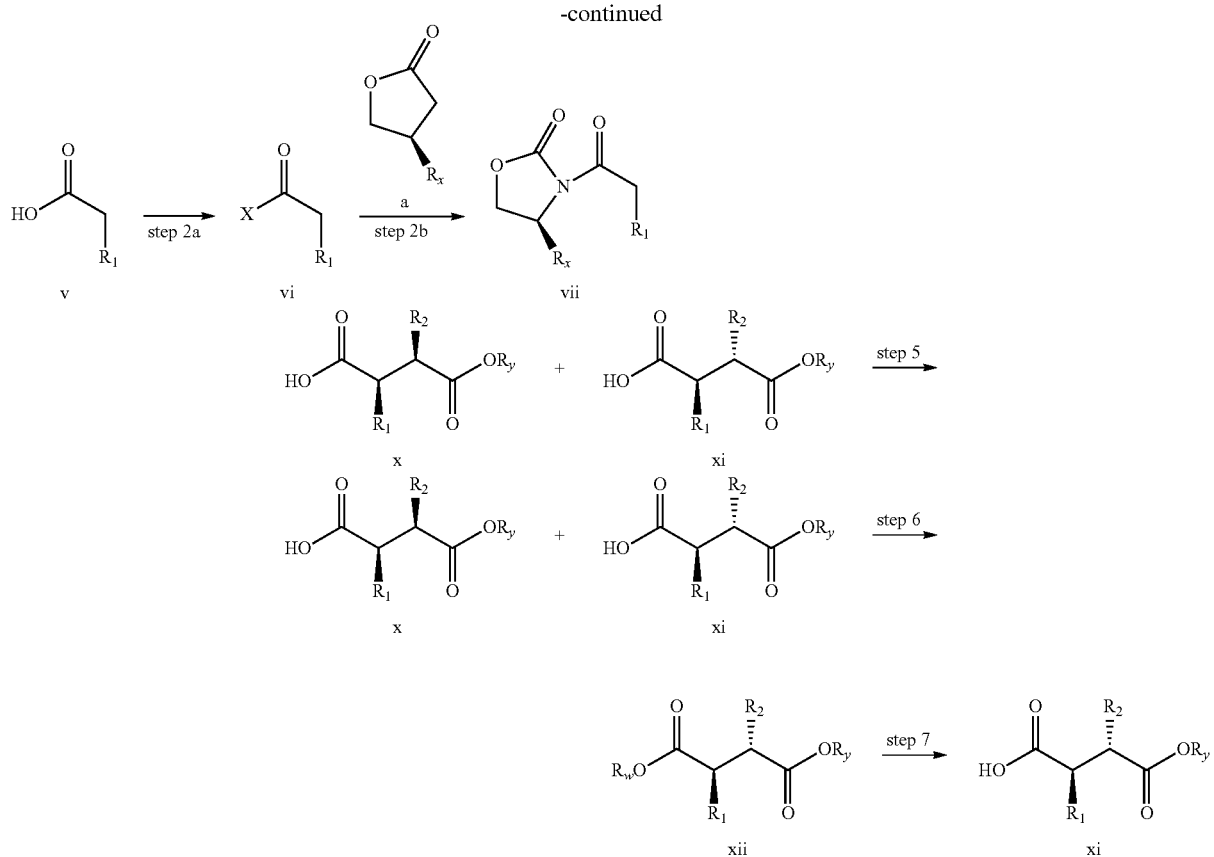

Step 1: The first step of Scheme 3 is accomplished by converting compound (xiii) to an ester (xv), employing one of the multiple ways known to one skilled in the art, such as treatment with a substituted acetimidate such as compound (xiv) in the presence of a reagent such as boron trifluoride etherate at an appropriate temperature in a solvent such as THF.

Step 2: Acid (v) can be converted to compound (vi) in multiple ways known to one skilled in the art. For example, treatment of acid (v) with a reagent such as oxalyl chloride in a solvent such as DCM gives the acid chloride (vi). Compound (vi) can be treated with an oxazolidinone (a) under standard conditions to give compound (vii) (Evans, D. A. et al., *J. Am. Chem. Soc.*, 112:4011 (1990)).

Step 3: Compound (vii) can be converted to a mixture of diastereomers (xvi) in multiple ways (Baran, P. et al., *J. Am. Chem. Soc.*, 130(34):11546 (2008)). For example, compound (xv) is treated with a base such as LDA in a solvent such as toluene, at low temperature such as −78° C. under an inert atmosphere such as $N_2$. The resulting mixture is added to a solution of compound (vii) treated with lithium chloride and a base such as LDA in a solvent such as toluene under an inert atmosphere such as $N_2$. To the resulting mixture of the enolates of compounds (xv) and (vii) is added bis(2-ethylhexanoyloxy)copper at a low temperature such as −78° C. under an inert atmosphere such as $N_2$ and warmed to room temperature to provide compound (xvi).

Step 4: Conversion of compound (xvi) to a mixture of compound (x) and compound (xi) may be accomplished by treating it with hydrogen peroxide and lithium hydroxide at an appropriate temperature using a mixture of solvents such as THF/water. The resulting mixture of diastereomers may then be utilized in subsequent synthetic steps. If necessary, the resulting mixture of diastereomers may be separated at this point via silica gel chromatography or preparative HPLC.

Step 5: Alternately, the mixture (x/xi) may be subjected to epimerization conditions, for example by treatment with LDA and diethylaluminum chloride followed by quenching with methanol or acetic acid to enrich the desired diastereomer. The resulting diastereomerically enriched mixture of compound may then be utilized in subsequent synthetic steps or the mixture of diastereoisomers may be separated if desired, employing suitable conditions such as preparative HPLC, preparative chiral HPLC or silica gel chromatography, and the resulting pure desired diastereoisomer (xi) used in the subsequent steps.

Step 6: Alternatively, the mixture of diastereomeric acids (x) and (xi) may be protected by treatment with, for example, benzyl bromide in the presence of a base such as $K_2CO_3$ in a solvent such as DMF. The resulting mixture of diastereoisomers may be separated if desired, employing suitable conditions such as preparative HPLC, preparative chiral HPLC or silica gel chromatography, and the resulting pure desired diastereoisomer compound (xii) used in the subsequent steps.

Step 7: The last step of Scheme 3 is a deprotection step and may be accomplished in several ways known to one skilled in the art. For example, for $R_w$=benzyl in compound (xii), treatment under hydrogenation conditions using a catalyst such as palladium on carbon in a solvent such as MeOH under a hydrogen atmosphere may provide compound (xi) that may subsequently be utilized, for example, in step 1 of Scheme 4.

Scheme 4

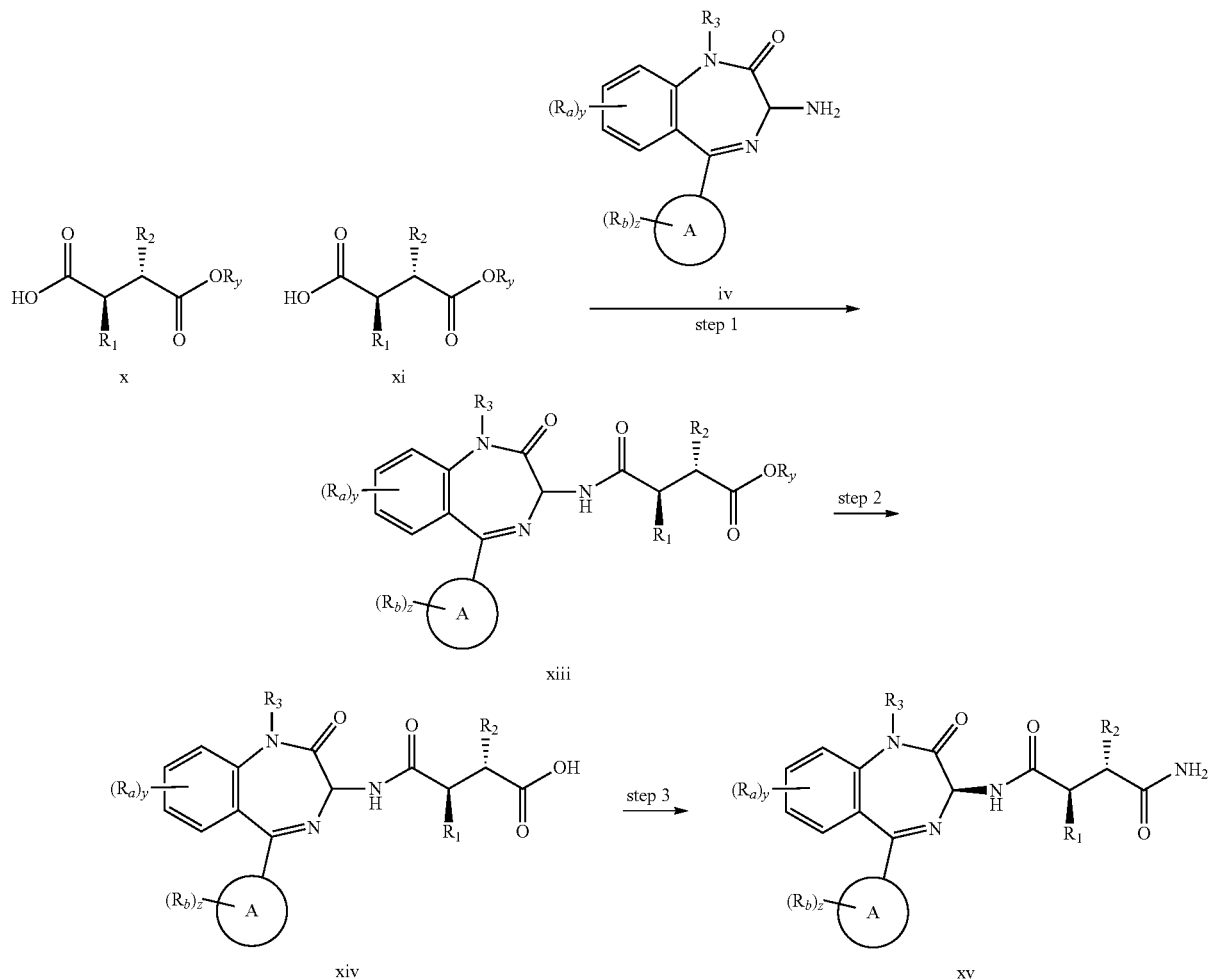

Step 1: Compounds of structure (iv) may be coupled to either pure diastereomer compound (xi) or a diastereomeric mixture of compounds (x/xi) in the presence of a coupling reagent such as TBTU and a base such as TEA, in a solvent such as DMF to provide compound (xiii) as either a diastereomerically pure compound or as a mixture of diastereoisomers, as appropriate, depending on the enantiomeric and/or diastereomeric purity of the coupling partners. This mixture may be used as such in the subsequent step, or if desired, may be purified using an appropriate separation technique, such as chiral preparative chromatography to provide the diastereomerically pure compounds.

Step 2: Treatment of compound (xiii) with an acid such as TFA at an appropriate temperature such as 0° C., in a solvent such as DCM provides compound (xiv) as either a diastereomerically pure compound or as a mixture of diastereoisomers. This mixture may be used as such in the subsequent step, or if desired, may be purified using an appropriate separation technique, such as chiral preparative chromatography to provide the diastereomerically pure compounds.

Step 3: Conversion of compound (xiv) to compound (xv) may be accomplished via coupling of compound (xiv) with an appropriate amine source such as ammonium chloride or ammonia, a carbodiimide such as EDC, HOBT and a base such as TEA in a solvent such as DMF. If necessary the diastereomeric mixture can be separated using an appropriate separation technique, such as chiral preparative chromatography. Also, if $R_3$ is H, (xv) may be, for example, treated with an aryl or alkyl halide in the presence of a base such as $K_2CO_3$ or $Cs_2CO_3$ in a solvent such as DMF to provide other $R_3$ substitutions.

EXAMPLES

The invention is further defined in the following Examples. It should be understood that the Examples are given by way of illustration only. From the above discussion and the Examples, one skilled in the art can ascertain the essential characteristics of the invention, and without departing from the spirit and scope thereof, can make various changes and modifications to adapt the invention to various uses and conditions. As a result, the invention is not limited by the illustrative examples set forth hereinbelow, but rather is defined by the claims appended hereto.

Abbreviations

ACN acetonitrile
AcOH acetic acid
Bn benzyl

Boc tert-butoxycarbonyl
CBz benzyloxycarbonyl
DAST (diethylamino)sulfur trifluoride
DCC 1,3-dicyclohexylcarbodiimide
DCM dichloromethane
DEA diethylamine
DIPEA diisopropylethylamine
DME dimethyl ether
DMF dimethylformamide
DMSO dimethyl sulfoxide
EDC 1-(3-dimethylaminopropyl)-3-ethylcarbodiimide hydrochloride
Et$_2$AlCl diethyl aluminum chloride
Et$_3$N triethyl amine
Et$_2$O diethyl ether
EtOH ethanol
EtOAc ethyl acetate
equiv. equivalence
g gram
h or hr hour(s)
HOAc acetic acid
HOBT hydroxybenzotriazole
HPLC high pressure liquid chromatography
LCMS Liquid Chromatography-Mass Spectroscopy
LDA lithium diisopropylamide
MeCN acetonitrile
MeOH methanol
min minute(s)
mL milliliter
mmol millimolar
MTBE methyl tert-butyl ether
NaHMDS sodium bis(trimethylsilyl)amide
n-BuLi n-butyl lithium
NH$_4$OAc ammonium acetate
NMM N-methylmorpholine
pyBOP bromotripyrrolidinophosphonium hexafluorophosphate
RT retention time
t-Bu tertiary butyl
tBuOH tertiary butyl alcohol
TBTU O-(1H-benzotriazol-1-yl)-N,N,N',N'-tetramethyluronium tetrafluoroborate
TEA triethylamine
TFA trifluoroacetic acid
Tf$_2$O trifluoromethylsulfonic anhydride
THF tetrahydrofuran Intermediate S-1: (2R,3S)-3-(tert-Butoxycarbonyl)-6,6,6-trifluoro-2-(3,3,3-trifluoropropyl)hexanoic acid

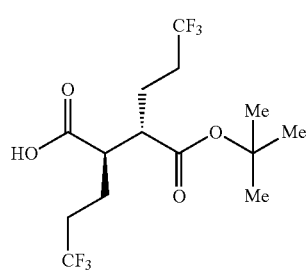

(S-1)

Intermediate S-1A: 3,3,3-Trifluoropropyl trifluoromethanesulfonate

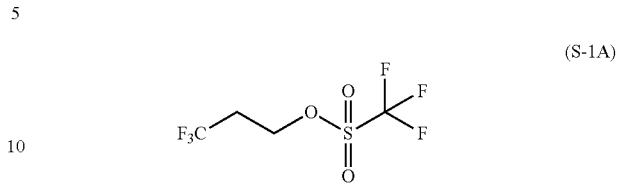

(S-1A)

To a cold (−25° C.), stirred solution of 2,6-lutidine (18.38 mL, 158 mmol) in DCM (120 mL) was added Tf$_2$O (24.88 mL, 147 mmol) over 3 min, and the mixture was stirred for 5 min. To the reaction mixture was added 3,3,3-trifluoropropan-1-ol (12 g, 105 mmol) over an interval of 3 min. After 2 hr, the reaction mixture was warmed to room temperature and stirred for 1 hr. The reaction mixture was concentrated to half its volume, then purified by loading directly on a silica gel column (330 g ISCO) and the product was eluted with DCM to afford Intermediate S-1A (13.74 g, 53%) as a colorless oil. $^1$H NMR (400 MHz, CDCl$_3$) δ ppm 4.71 (2 H, t, J=6.15 Hz), 2.49-2.86 (2 H, m).

Intermediate S-1B: (4S)-4-Benzyl-3-(5,5,5-trifluoropentanoyl)-1,3-oxazolidin-2-one

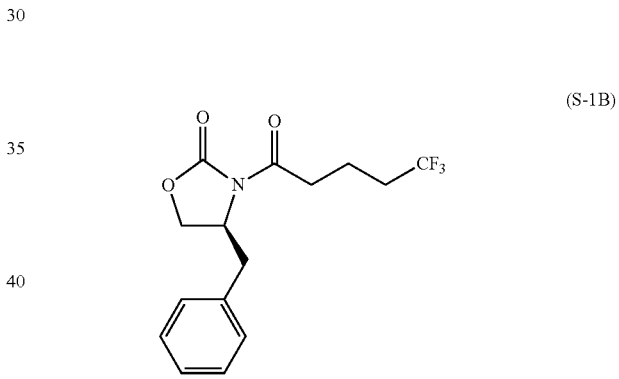

(S-1B)

To a stirring solution of 5,5,5-trifluoropentanoic acid (14.76 g, 95 mmol) and DMF (0.146 mL) in DCM (50 mL) was slowly added oxalyl chloride (8.27 mL, 95 mmol). After 2 h, the mixture was concentrated to dryness. A separate flask was changed with (S)-4-benzyloxazolidin-2-one (16.75 g, 95 mmol) in THF (100 mL) and then cooled to −78° C. To the solution was slowly added n-BuLi (2.5M, 37.8 mL, 95 mmol) over 10 min, stirred for 10 min, and then a solution of the above acid chloride in THF (50 mL) was slowly added over 5 min. The mixture was stirred for 30 min, and then warmed to room temperature. The mixture was quenched with saturated aqueous NH$_4$Cl, 10% aqueous LiCl was then added, and the mixture was extracted with Et$_2$O. The organic layer was washed with saturated aqueous NaHCO$_3$ then with brine, dried (MgSO$_4$), filtered and concentrated to dryness. The residue was purified by SiO$_2$ chromatography (ISCO, 330 g column, eluting with a gradient from 100% hexane to 100% EtOAc) to afford the product Intermediate S-1B; (25.25 g, 85%): $^1$H NMR (400 MHz, CDCl$_3$) δ ppm 7.32-7.39 (2 H, m), 7.30 (1 H, d, J=7.05 Hz), 7.18-7.25 (2 H, m), 4.64-4.74 (1 H, m), 4.17-4.27 (2 H, m), 3.31 (1 H, dd, J=13.35, 3.27 Hz), 3.00-3.11 (2 H, m), 2.79 (1 H, dd, J=13.35, 9.57 Hz), 2.16-2.28 (2 H, m), 1.93-2.04 (2 H, m).

Intermediate S-1C: tert-Butyl (3R)-3-(((4S)-4-benzyl-2-oxo-1,3-oxazolidin-3-yl)carbonyl)-6,6,6-trifluorohexanoate

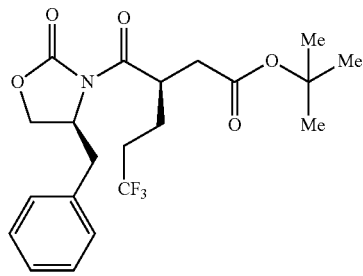

(S-1C)

To a cold (−78° C.), stirred solution of Intermediate S-1B (3.03 g, 9.61 mmol) in THF (20 mL) was added NaHMDS (1.0M in THF) (10.6 mL, 10.60 mmol) under a nitrogen atmosphere. After 2 hours, tert-butyl 2-bromoacetate (5.62 g, 28.8 mmol) was added neat via syringe at −78° C. and stirring was maintained at the same temperature. After 6 hours, the reaction mixture was warmed to room temperature. The reaction mixture was partitioned between saturated NH$_4$Cl and EtOAc. The organic phase was separated, and the aqueous phase was extracted with EtOAc (3×). The combined organics were washed with brine, dried (Na$_2$SO$_4$), filtered and concentrated under reduced pressure. The residue was purified by flash chromatography (Teledyne ISCO CombiFlash Rf, 5% to 100% solvent A/B=hexanes/EtOAc, REDISEP® SiO$_2$ 120 g). Concentration of the appropriate fractions provided Intermediate S-1C (2.79 g, 67.6%) as a colorless viscous oil: $^1$H NMR (400 MHz, CDCl$_3$) δ ppm 7.34 (2 H, d, J=7.30 Hz), 7.24-7.32 (3 H, m), 4.62-4.75 (1 H, m, J=10.17, 6.89, 3.43, 3.43 Hz), 4.15-4.25 (3 H, m), 3.35 (1 H, dd, J=13.60, 3.27 Hz), 2.84 (1 H, dd, J=16.62, 9.57 Hz), 2.75 (1 H, dd, J=13.35, 10.07 Hz), 2.47 (1 H, dd, J=16.62, 4.78 Hz), 2.11-2.23 (2 H, m), 1.90-2.02 (1 H, m), 1.72-1.84 (1 H, m), 1.44 (9 H, s).

Intermediate S-1D: (2R)-2-(2-tert-Butoxy-2-oxoethyl)-5,5,5-trifluoropentanoic acid

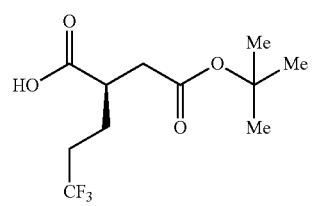

(S-1D)

To a cool (0° C.), stirred solution of Intermediate S-1C (2.17 g, 5.05 mmol) in THF (50 mL) and water (15 mL) was added a solution of LiOH (0.242 g, 10.11 mmol) and H$_2$O$_2$ (2.065 mL, 20.21 mmol) in H$_2$O (2 mL). After 10 min, the reaction mixture was removed from the ice bath, stirred for 1 h, and then recooled to 0° C. Saturated aqueous NaHCO$_3$ (25 mL) and saturated aqueous Na$_2$SO$_3$ (25 mL) were added to the reaction mixture. The reaction mixture was stirred for 10 min, and then partially concentrated. The resulting mixture was extracted with DCM (2×), cooled with ice and made acidic with conc. HCl to pH 3. The mixture was saturated with solid NaCl, extracted with EtOAc (3×), and then dried over MgSO$_4$, filtered and concentrated to a colorless oil to afford Intermediate S-1D, 1.2514 g, 92%): $^1$H NMR (400 MHz, CDCl$_3$) δ ppm 2.83-2.95 (1 H, m), 2.62-2.74 (1 H, m), 2.45 (1 H, dd, J=16.62, 5.79 Hz), 2.15-2.27 (2 H, m), 1.88-2.00 (1 H, m), 1.75-1.88 (1 H, m), 1.45 (9 H, s).

Intermediate S-1: (2R,3S)-3-(tert-Butoxycarbonyl)-6,6,6-trifluoro-2-(3,3,3-trifluoropropyl)hexanoic acid, and Intermediate S-1E: (2R,3R)-3-(tert-Butoxycarbonyl)-6,6,6-trifluoro-2-(3,3,3-trifluoropropyl)hexanoic acid

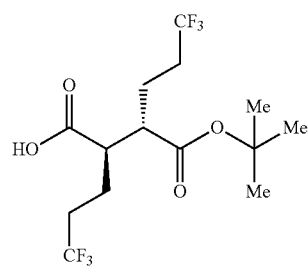

(S-1)

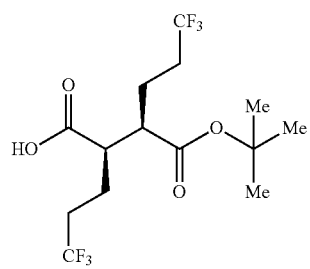

(S-1E)

To a cold (−78° C.), stirred solution of Intermediate S-1D (5 g, 18.50 mmol) in THF (60 mL) was slowly added LDA (22.2 mL, 44.4 mmol, 2.0M) over 7 min. After stirring for 2 hr, Intermediate S-1A (6.38 g, 25.9 mmol) was added to the reaction mixture over 3 min. After 60 min, the reaction mixture was warmed to −25° C. (ice/MeOH/dry ice) and stirred for an additional 60 min at which time saturated aqueous NH$_4$Cl was added. The separated aqueous phase was acidified with 1N HCl aqueous to pH 3, then extracted with Et$_2$O, washed the combined organic layers with brine (×2), dried over MgSO$_4$, filtered and concentrated to provide a 1:4 (S-1: S-1E) mixture (as determined by $^1$H NMR) of Intermediate S-1 and Intermediate S-1E (6.00 g, 89%) as a pale yellow solid. $^1$H NMR (500 MHz, CDCl$_3$) δ ppm 2.81 (1 H, ddd, J=10.17, 6.32, 3.85 Hz), 2.63-2.76 (1 H, m), 2.02-2.33 (4 H, m), 1.86-1.99 (2 H, m), 1.68-1.85 (2 H, m), 1.47 (9 H, s).

Intermediate S-1: (2R,3S)-3-(tert-Butoxycarbonyl)-6,6,6-trifluoro-2-(3,3,3-trifluoropropyl)hexanoic acid, and Intermediate S-1E: (2R,3R)-3-(tert-Butoxycarbonyl)-6,6,6-trifluoro-2-(3,3,3-trifluoropropyl)hexanoic acid

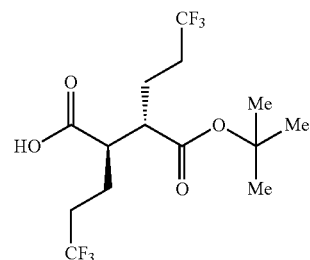

(S-1)

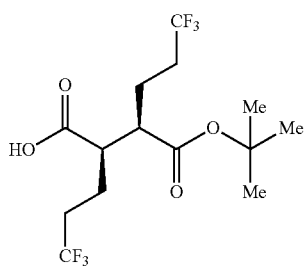

(S-1E)

To a cold (−78° C.), stirred solution of a mixture of Intermediate S-1 and Intermediate S-1E (5.97 g, 16.30 mmol) in THF (91 mL) was added LDA (19 mL, 38.0 mmol, 2.0M in THF/hexane/ethyl benzene) dropwise via syringe over 10 min (internal temperature never exceeded −65° C., J-KEM® probe in reaction solution). The reaction mixture was stirred for 15 min, warmed to room temperature (24° C. water bath), stirred for 15 min, and cooled to −78° C. for 15 min. To the reaction mixture was added Et$_2$AlCl (41 mL, 41.0 mmol, 1M in hexane) via syringe (internal temperature never exceeded −55° C.). The reaction mixture was stirred for 10 min, warmed to room temperature (24° C. bath) for 15 min then cooled to −78° C. for 15 min. Meanwhile, a 1000 mL round bottom flask was charged with MeOH (145 mL) and pre-cooled to −78° C. With vigorous stirring the reaction mixture was transferred via cannula over 5 min to the MeOH. The flask was removed from the bath, ice was added followed by slow addition of 1N HCl (147 mL, 147 mmol). Gas evolution was observed as the HCl was added. The reaction mixture was allowed to warm to room temperature during which the gas evolution subsided. The reaction mixture was diluted with EtOAc (750 mL), saturated with NaCl, the organic phase was separated, washed with a solution of potassium fluoride (8.52 g, 147 mmol) and 1N HCl (41 mL, 41.0 mmol) in water (291 mL), brine (100 mL), dried (Na$_2$SO$_4$) filtered and concentrated then dried under vacuum. $^1$H NMR showed product was 9:1 mixture of Intermediate S-1 and Intermediate S-1E. Obtained the enriched mixture of Intermediate S-1 and Intermediate S-1E (6.12 g, >99% yield) as a dark amber solid: $^1$H NMR (400 MHz, CDCl$_3$) δ ppm 2.64-2.76 (2 H, m), 2.04-2.35 (4 H, m), 1.88-2.00 (2 H, m), 1.71-1.83 (2 H, m), 1.48 (9 H, s).

Alternate Procedure to Make Intermediate S-1

Intermediate S-1F: (2R,3S)-1-Benzyl 4-tert-butyl 2,3-bis(3,3,3-trifluoropropyl)succinate

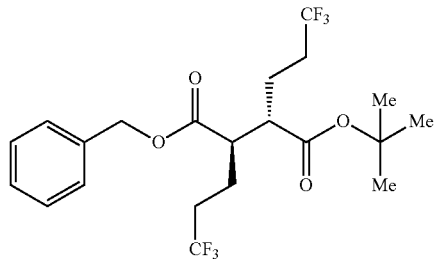

(S-1F)

To a stirred solution of a 9:1 enriched mixture of Intermediate S-1 and Intermediate S-1E (5.98 g, 16.33 mmol) in DMF (63 ml) was added potassium carbonate (4.06 g, 29.4 mmol) and benzyl bromide (2.9 ml, 24.38 mmol). The reaction mixture was stirred overnight. The reaction mixture was diluted with EtOAc (1000 mL), washed with 10% LiCl (3×200 mL), brine (200 mL) then dried (Na$_2$SO$_4$), filtered and concentrated then dried under vacuum. The residue was purified by SiO$_2$ chromatography using a toluene:hexane gradient. Obtained diastereomerically pure Intermediate S-1F (4.81 g, 65%) as a colorless solid: $^1$H NMR (400 MHz, chloroform-d) δ 7.32-7.43 (m, 5H), 5.19 (d, J=12.10 Hz, 1H), 5.15 (d, J=12.10 Hz, 1H), 2.71 (dt, J=3.52, 9.20 Hz, 1H), 2.61 (dt, J=3.63, 9.63 Hz, 1H), 1.96-2.21 (m, 4H), 1.69-1.96 (m, 3H), 1.56-1.67 (m, 1H), 1.45 (s, 9H).

Intermediate S-1: (2R,3S)-3-(tert-Butoxycarbonyl)-6,6,6-trifluoro-2-(3,3,3-trifluoropropyl)hexanoic acid

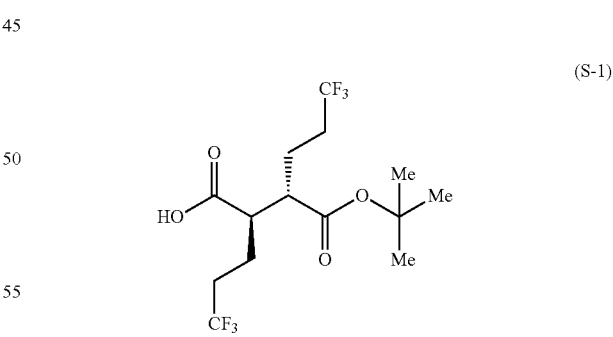

(S-1)

To a solution of Intermediate S-1F (4.81 g, 10.54 mmol) in MeOH (100 mL) was added 10% palladium on carbon (wet, Degussa type, 568.0 mg, 0.534 mmol) in a H$_2$-pressure flask. The vessel was purged with N$_2$ (4×) then with H$_2$ (2×), then pressurized to 50 psi and shaken overnight. The reaction mixture was depressurized and purged, the mixture was filtered through CELITE®, washed with MeOH then concentrated and dried under vacuum. Obtained Intermediate S-1 (3.81 g, 99% yield)) as a colorless solid: $^1$H NMR (400 MHz, chloroform-d) δ 2.62-2.79 (m, 2H), 2.02-2.40 (m, 4H), 1.87-2.00 (m, 2H), 1.67-1.84 (m, 2H), 1.48 (s, 9H).

Alternate Procedure to Make Intermediate S-1

Intermediate S-1: (2R,3S)-3-(tert-Butoxycarbonyl)-6,6,6-trifluoro-2-(3,3,3-trifluoropropyl)hexanoic acid

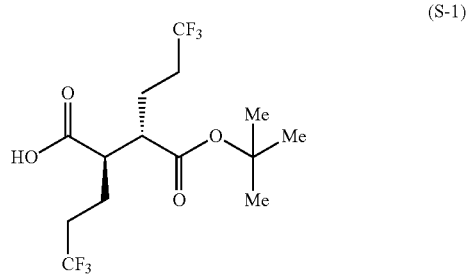 [SMILES: CC(C)(C)OC(=O)[C@@H](CCC(F)(F)F)[C@@H](CCC(F)(F)F)C(=O)O]

(S-1)

Intermediate S-1 as a mixture with Intermediate S-1E was prepared in a procedure identical as above from Intermediate S-1D to afford a 1:2.2 mixture of Intermediate S-1 and Intermediate S-1E (8.60 g, 23.48 mmol), which was enriched using LDA (2.0 M solution in THF, ethyl benzene and heptane, 28.2 mL, 56.4 mmol) and diethyl aluminum chloride (1.0 M solution in hexane, 59 mL, 59.0 mmol) in THF (91 mL). After workup as described above, the resulting residue was found to be a 13.2:1 (by ¹H NMR) mixture of Intermediate S-1 and Intermediate S-1E, which was treated as follows: The crude material was dissolved in MTBE (43 mL). Hexanes (26 mL) were slowly charged to the reaction mixture while maintaining a temperature below 30° C. The reaction mixture was stirred for 10 min. Next, tert-butylamine (2.7 mL, 1.1 eq) was charged slowly over a period of 20 minutes while maintaining a temperature below 30° C. This addition was observed to be exothermic. The reaction mixture was stirred for 2 hrs below 30° C. and filtered. The solid material was washed with 5:3 MTBE:hexane (80 mL), the filtrate was concentrated and set aside. The filtered solid was dissolved in dichloromethane (300 mL), washed with 1N HCl (100 mL), the organic layer was washed with brine (100 mL×2), then was concentrated under reduced pressure below 45° C. Obtained Intermediate S-1 (5.46 g, 64%).

A Second Alternate Procedure for Preparing Intermediate S-1

Intermediate S-1G: tert-Butyl 5,5,5-trifluoropentanoate

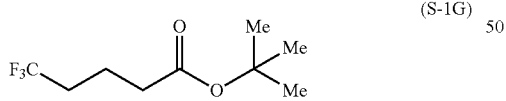

(S-1G)

To a stirred solution of 5,5,5-trifluoropentanoic acid (5 g, 32.0 mmol) in THF (30 mL) and hexane (30 mL) at 0° C., was added tert-butyl 2,2,2-trichloroacetimidate (11.46 mL, 64.1 mmol). The mixture was stirred for 15 min at 0° C. Boron trifluoride etherate (0.406 mL, 3.20 mmol) was added and the reaction mixture was allowed to warm to room temperature overnight. To the clear reaction mixture was added solid NaHCO₃ (5 g) and stirred for 30 min. The mixture was filtered through MgSO₄ and washed with hexanes (200 mL). The solution was allowed to rest for 45 min, and the resulting solid material was removed by filtering on the same MgSO₄ filter again, washed with hexanes (100 mL) and concentrated under reduced pressure without heat. The volume was reduced to about 30 mL, filtered through a clean fritted funnel, washed with hexane (5 mL), and then concentrated under reduced pressure without heat. The resulting neat oil was filtered through a 0.45 μm nylon membrane filter disk to provide Intermediate S-1G (6.6 g, 31.4 mmol 98% yield) as a colorless oil: ¹H NMR (400 MHz, CDCl₃) δ ppm 1.38 (s, 9 H) 1.74-1.83 (m, 2 H) 2.00-2.13 (m, 2 H) 2.24 (t, J=7.28 Hz, 2 H).

Intermediate S-1H: (4S)-4-(Propan-2-yl)-3-(5,5,5-trifluoropentanoyl)-1,3-oxazolidin-2-one

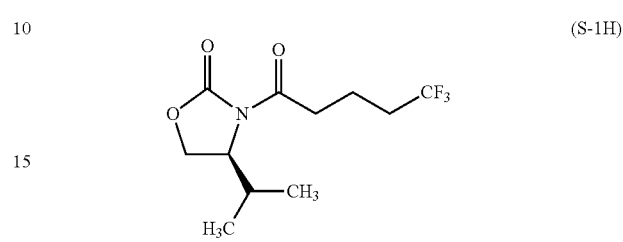

(S-1H)

To a stirred solution of 5,5,5-trifluoropentanoic acid (5.04 g, 32.3 mmol) in DCM (50 mL) and DMF (3 drops) was added oxalyl chloride (3.4 mL, 38.8 mmol) dropwise over 5 min and the solution was stirred until all bubbling subsided. The reaction mixture was concentrated under reduced pressure to give pale yellow oil. To a separate flask charged with a solution of (4S)-4-(propan-2-yl)-1,3-oxazolidin-2-one (4.18 g, 32.4 mmol) in THF (100 mL) at −78° C. was added n-BuLi (2.5M in hexane) (13.0 mL, 32.5 mmol) dropwise via syringe over 5 min. After stirring for 10 min, the above acid chloride dissolved in THF (20 mL) was added via cannula over 15 min. The reaction mixture was warmed to 0° C., and was allowed to warm to room temperature as the bath warmed and stirred overnight. To the reaction mixture was added saturated NH₄Cl, and then extracted with EtOAc (2×). The combined organics were washed with brine, dried (Na₂SO₄), filtered and concentrated under reduced pressure. The crude material was purified by flash chromatography (Teledyne ISCO CombiFlash Rf, 5% to 60% solvent A/B=hexanes/EtOAc, REDISEP® SiO₂ 120 g). Concentration of appropriate fractions provided Intermediate S-1H (7.39 g, 86%) as a colorless oil: ¹H NMR (400 MHz, CDCl₃) δ ppm 4.44 (1 H, dt, J=8.31, 3.53 Hz), 4.30 (1 H, t, J=8.69 Hz), 4.23 (1 H, dd, J=9.06, 3.02 Hz), 2.98-3.08 (2 H, m), 2.32-2.44 (1 H, m, J=13.91, 7.02, 7.02, 4.03 Hz), 2.13-2.25 (2 H, m), 1.88-2.00 (2 H, m), 0.93 (3 H, d, J=7.05 Hz), 0.88 (3 H, d, J=6.80 Hz).

Intermediate S-1I: (2S,3R)-tert-Butyl 6,6,6-trifluoro-3-((S)-4-isopropyl-2-oxooxazolidine-3-carbonyl)-2-(3,3,3-trifluoropropyl)hexanoate, and Intermediate S-1J: (2R,3R)-tert-Butyl 6,6,6-trifluoro-3-((S)-4-isopropyl-2-oxooxazolidine-3-carbonyl)-2-(3,3,3-trifluoropropyl)hexanoate

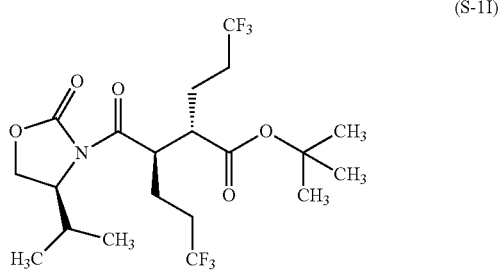

(S-1I)

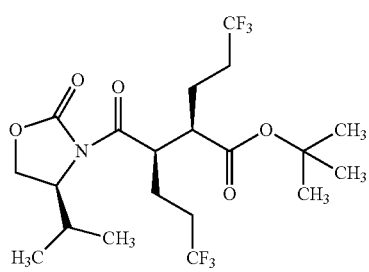

(S-1J)

To a cold (−78° C.), stirred solution of diisopropylamine (5.3 mL, 37.2 mmol) in THF (59 mL) under nitrogen atmosphere was added n-BuLi (2.5M in hexane) (14.7 mL, 36.8 mmol). The reaction mixture was warmed to 0° C. to give a 0.5M solution of LDA. A separate vessel was charged with Intermediate S-1H (2.45 g, 9.17 mmol), the material was azeotroped twice with benzene (the Roto Vap air inlet was fitted with nitrogen inlet to completely exclude humidity) then toluene (15.3 mL) was added. This solution was added to a flask containing dry lithium chloride (1.96 g, 46.2 mmol). To the resultant mixture, cooled to −78° C., was added LDA solution (21.0 mL, 10.5 mmol) and stirred at −78° C. for 10 min, warmed to 0° C. for 10 min then recooled to −78° C. To a separate reaction vessel containing Intermediate S-1G (3.41 g, 16.07 mmol), also azeotroped twice with benzene, was added toluene (15.3 mL), cooled to −78° C. and LDA (37.0 mL, 18.5 mmol) was added, the resulting solution was stirred at −78° C. for 25 min. At this time the enolate derived from the ester was transferred via cannula into the solution of the oxazolidinone enolate, stirred at −78° C. for an additional 5 min at which time the septum was removed and solid powdered bis(2-ethylhexanoyloxy)copper (9.02 g, 25.8 mmol) was rapidly added to the reaction vessel and the septum replaced. The vessel was immediately removed from the cold bath and immersed into a warm water bath (40° C.) with rapid swirling with a concomitant color change from the initial turquoise to brown. The reaction mixture was stirred for 20 min, was poured into 5% aqueous $NH_4OH$ (360 mL) and extracted with EtOAc (2×). The combined organics were washed with brine, dried ($Na_2SO_4$), filtered and concentrated under reduced pressure. The residue was purified by flash chromatography (Teledyne ISCO CombiFlash Rf, 0% to 60% solvent A/B=hexanes/EtOAc, REDISEP® $SiO_2$ 120 g). Concentration of appropriate fractions provided a mixture of Intermediates S-1I and S-1J (2.87 g, 66%) as pale yellow viscous oil. $^1$H NMR showed the product was a 1.6:1 mixture of diastereomers S-1I:S-1J as determined by the integration of the multiplets at 2.74 and 2.84 ppm: $^1$H NMR (400 MHz, $CDCl_3$) δ ppm 4.43-4.54 (2 H, m), 4.23-4.35 (5 H, m), 4.01 (1 H, ddd, J=9.54, 6.27, 3.51 Hz), 2.84 (1 H, ddd, J=9.41, 7.28, 3.64 Hz), 2.74 (1 H, ddd, J=10.29, 6.27, 4.02 Hz), 2.37-2.48 (2 H, m, J=10.38, 6.98, 6.98, 3.51, 3.51 Hz), 2.20-2.37 (3 H, m), 1.92-2.20 (8 H, m), 1.64-1.91 (5 H, m), 1.47 (18 H, s), 0.88-0.98 (12 H, m).

Intermediate S-1: (2R,3S)-3-(tert-Butoxycarbonyl)-6,6,6-trifluoro-2-(3,3,3-trifluoropropyl)hexanoic acid, and Intermediate S-1E: (2R,3R)-3-(tert-Butoxycarbonyl)-6,6,6-trifluoro-2-(3,3,3-trifluoropropyl)hexanoic acid

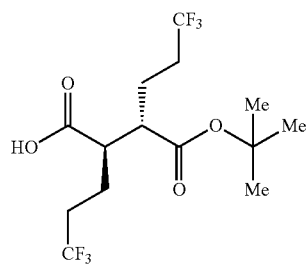

(S-1)

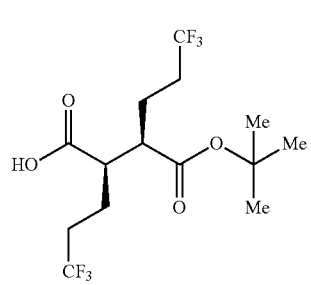

(S-1E)

To a cool (0° C.), stirred solution of Intermediate S-1I and Intermediate S-1J (4.54 g, 9.51 mmol) in THF (140 mL) and water (42 mL) was sequentially added hydrogen peroxide (30% in water) (10.3 g, 91 mmol) and LiOH (685.3 mg, 28.6 mmol) and the mixture was stirred for 1 hr. At this time the reaction vessel was removed from the cold bath and then stirred for 1.5 hr. The reaction was judged complete by HPLC. To the reaction mixture was added saturated $NaHCO_3$ (45 mL) and saturated $Na_2SO_3$ (15 mL), and then partially concentrated under reduced pressure. The resulting crude solution was extracted with DCM (3×). The aqueous phase was acidified to pH~1-2 with 1N HCl, extracted with DCM (3×) and EtOAc (1×). The combined organics were washed with brine, dried ($Na_2SO_4$), filtered and concentrated under reduced pressure to provide a mixture of Intermediates S-1 and S-1E (3.00 g, 86%) as a colorless oil: $^1$H NMR (400 MHz, $CDCl_3$) δ ppm 2.76-2.84 (1 H, m, diastereomer 2), 2.64-2.76 (3 H, m), 2.04-2.35 (8 H, m), 1.88-2.00 (4 H, m), 1.71-1.83 (4 H, m), 1.48 (9 H, s, diastereomer 1), 1.46 (9 H, s, diastereomer 2); $^1$H NMR showed a 1.7:1 mixture of S-1E:S-1F by integration of the peaks for the t-butyl groups.

Intermediate S-1: (2R,3S)-3-(tert-Butoxycarbonyl)-6,6,6-trifluoro-2-(3,3,3-trifluoropropyl)hexanoic acid, and Intermediate S-1F: (2R,3R)-3-(tert-Butoxycarbonyl)-6,6,6-trifluoro-2-(3,3,3-trifluoropropyl)hexanoic acid

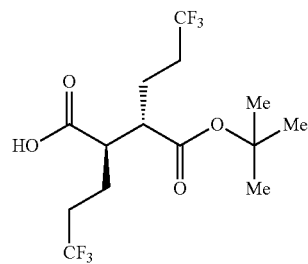

(S-1)

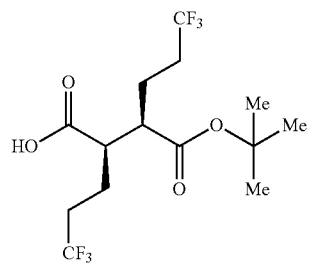

(S-1E)

To a cold (−78° C.), stirred solution of diisopropylamine (1.7 mL, 11.93 mmol) in THF (19 mL) under nitrogen atmosphere was added n-BuLi (2.5M in hexanes) (4.8 mL, 12.00 mmol). The mixture was stirred for 5 min and then warmed to 0° C. In a separate vessel, to a cold (−78° C.) stirred solution of the mixture of Intermediate S-1 and S-1E (1.99 g, 5.43 mmol) in THF (18 mL) was added the LDA solution prepared above via cannula slowly over 25 min. The mixture was stirred for 15 min, then warmed to room temperature (placed in a 24° C. water bath) for 15 min, and then again cooled to −78° C. for 15 min. To the reaction mixture was added Et$_2$AlCl (1M in hexane) (11.4 mL, 11.40 mmol) via syringe, stirred for 10 min, warmed to room temperature for 15 min and then cooled back to −78° C. for 15 min. Methanol (25 mL) was rapidly added, swirled vigorously while warming to room temperature, then concentrated to ~¼ original volume. The mixture was dissolved in EtOAc and washed with 1N HCl (50 mL) and ice (75 g). The aqueous phase was separated, extracted with EtOAc (2×). The combined organics were washed with a mixture of KF (2.85 g in 75 mL water) and 1N HCl (13 mL) [resulting solution pH 3-4], then with brine, dried (Na$_2$SO$_4$), filtered and concentrated under reduced pressure to give a 9:1 (S-1:S-1E) enriched diastereomeric mixture (as determined by $^1$H NMR) of Intermediate S-1 and Intermediate S-1E (2.13 g, >99%) as a pale yellow viscous oil: $^1$H NMR (400 MHz, CDCl$_3$) δ ppm 2.64-2.76 (2 H, m), 2.04-2.35 (4 H, m), 1.88-2.00 (2 H, m), 1.71-1.83 (2 H, m), 1.48 (9 H, s).

Intermediate S-2: (2R,3S)-3-(tert-Butoxycarbonyl)-6,6,6-trifluoro-2-(3-fluoropropyl)hexanoic acid

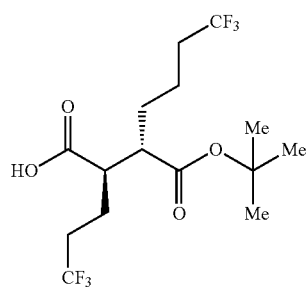

(S-2)

Intermediate S-2: (2R,3S)-3-(tert-Butoxycarbonyl)-7,7,7-trifluoro-2-(3,3,3-trifluoropropyl)heptanoic acid, and Intermediate S-2A: (2R,3R)-3-(tert-Butoxycarbonyl)-7,7,7-trifluoro-2-(3,3,3-trifluoropropyl)heptanoic acid

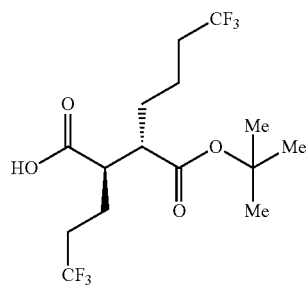

(S-2)

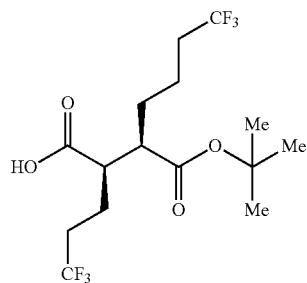

(S-2A)

To a cold (−78° C.), stirred solution of Intermediate S-1D (1.72 g, 6.36 mmol) in THF (30 mL) was slowly added LDA (7.32 mL, 14.6 mmol) over 7 min. After stirring for 1 h, 4,4,4-trifluorobutyltrifluoromethanesulfonate (2.11 g, 8.11 mmol) was added to the reaction mixture over 2 min. After 15 min, the reaction mixture was warmed to −25° C. (ice/MeOH/dry ice) for 1 h, and then cooled to −78° C. After 80 min, the reaction was quenched with a saturated aqueous NH$_4$Cl solution (10 mL). The reaction mixture was again diluted with brine and the solution was adjusted to pH 3 with 1N HCl. The aqueous layer was extracted with ether. The combined organics were washed with brine, dried over anhydrous magnesium sulfate, and concentrated under reduced pressure to provide a mixture of Intermediate S-2 and S-2A (2.29 g, 95%) as a colorless oil. $^1$H NMR (400 MHz, chloroform-d) δ 2.83-2.75 (m, 1H), 2.64 (ddd, J=9.9, 6.7, 3.6 Hz, 1H), 2.32-2.03 (m, 5H), 1.98-1.70 (m, 3H), 1.69-1.52 (m, 3H), 1.50-1.42 (m, 9H) $^1$H NMR showed a 1:4.5 mixture (S-2:S-2A) of diastereomers by integration of the peaks for the t-Bu groups.

Intermediate S-2: (2R,3S)-3-(tert-Butoxycarbonyl)-7,7,7-trifluoro-2-(3,3,3-trifluoropropyl)heptanoic acid, and Intermediate S-2A: (2R,3R)-3-(tert-butoxycarbonyl)-7,7,7-trifluoro-2-(3,3,3-trifluoropropyl)heptanoic acid

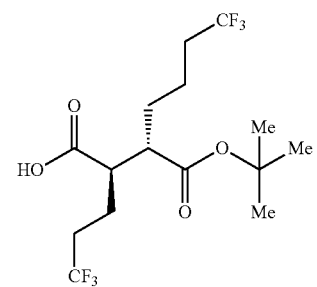

(S-2)

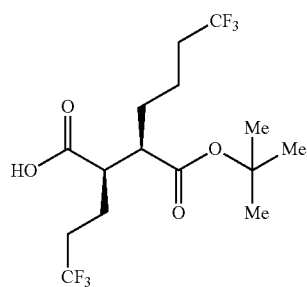

(S-2A)

A mixture of Intermediate S-2 and Intermediate S-2A (2.29 g, 6.02 mmol) was taken in THF (38 mL) to give a colorless solution which was cooled to −78° C. Then, LDA (7.23 mL, 14.5 mmol) (2.0M in heptane/THF/ethylbenzene) was slowly added to the reaction mixture over 3 min. After stirring for 15 min the reaction mixture was placed in a room temperature water bath. After 15 min the reaction mixture was placed back in a −78° C. bath and then diethylaluminum chloride (14.5 mL, 14.5 mmol) (1M in hexane) was added slowly over 5 min. The reaction mixture was stirred at −78° C. After 15 min the reaction mixture was placed in a room temperature water bath for 10 min and then cooled back to −78° C. bath. After 15 min the reaction was quenched with MeOH (30.0 mL, 741 mmol), removed from the −78° C. bath and concentrated. To the reaction mixture was added ice and HCl (60.8 mL, 60.8 mmol) then extracted with EtOAc (2×200 mL). The organic layer was washed with potassium fluoride (3.50 g, 60.3 mmol) in 55 mL H$_2$O and 17.0 mL of 1N HCl. The organics were dried over anhydrous magnesium sulfate and concentrated under reduced pressure to provide an enriched mixture of Intermediate S-2 and Intermediate S-2A (2.25 g, 98% yield) as light yellow oil. $^1$H NMR (400 MHz, chloroform-d) δ 2.83-2.75 (m, 1H), 2.64 (ddd, J=9.9, 6.7, 3.6 Hz, 1H), 2.32-2.03 (m, 5H), 1.98-1.70 (m, 3H), 1.69-1.52 (m, 3H), 1.50-1.42 (m, 9H). $^1$H NMR showed a 9:1 ratio in favor of the desired diastereomer Intermediate S-2.

Intermediate S-2B: (2R,3S)-1-Benzyl 4-tert-butyl 2,3-bis(4,4,4-trifluorobutyl)succinate

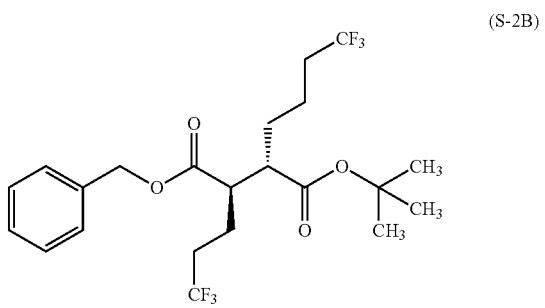 [SMILES: CC(C)(C)OC(=O)[C@@H](CCCC(F)(F)F)[C@@H](CCC(F)(F)F)C(=O)OCc1ccccc1]

To a stirred 9:1 mixture of Intermediate S-2 and Intermediate S-2A (2.24 g, 5.89 mmol) and potassium carbonate (1.60 g, 11.58 mmol) in DMF (30 mL) was added benzyl bromide (1.20 mL, 10.1 mmol)). The reaction mixture was stirred at room temperature for 19 h. The reaction mixture was diluted with ethyl acetate (400 mL) and washed with 10% LiCl solution (3×100 mL), brine (50 mL), and then dried over anhydrous magnesium sulfate, filtered and concentrated to dryness under vacuum. The residue was purified by flash chromatography (Teledyne ISCO CombiFlash 0% to 100% solvent A/B=hexane/EtOAc, REDISEP® SiO$_2$ 220 g, detecting at 254 nm, and monitoring at 220 nm). Concentration of the appropriate fractions provided Intermediate S-2B (1.59 g, 57.5%). HPLC: RT=3.863 min (CHROMOLITH® Speed-ROD column 4.6×50 mm, 10-90% aqueous methanol over 4 minutes containing 0.1% TFA, 4 mL/min, monitoring at 220 nm). $^1$H NMR (400 MHz, chloroform-d) δ 7.40-7.34 (m, 5H), 5.17 (d, J=1.8 Hz, 2H), 2.73-2.64 (m, 1H), 2.55 (td, J=10.0, 3.9 Hz, 1H), 2.16-1.82 (m, 5H), 1.79-1.57 (m, 3H), 1.53-1.49 (m, 1H), 1.45 (s, 9H), 1.37-1.24 (m, 1H).

Intermediate S-2: (2R,3S)-3-(tert-Butoxycarbonyl)-6,6,6-trifluoro-2-(4,4,4-trifluorobutyl)hexanoic acid

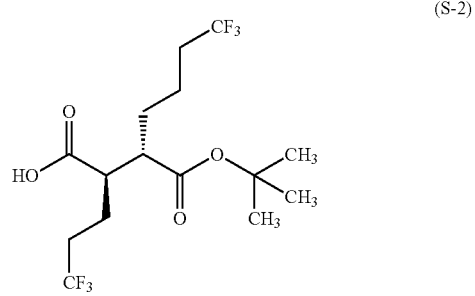 [SMILES: CC(C)(C)OC(=O)[C@@H](CCCC(F)(F)F)[C@@H](CCC(F)(F)F)C(=O)O]

To a stirred solution of Intermediate S-2B (1.59 g, 3.37 mmol) in MeOH (10 mL) and EtOAc (10 mL) under nitrogen was added 10% Pd/C (510 mg). The atmosphere was replaced with hydrogen and the reaction mixture was stirred at room temperature for 2.5 h. The palladium catalyst was filtered off through a 4 μM polycarbonate film and rinsed with MeOH. The filtrate was concentrated under reduced pressure to give Intermediate S-2 (1.28 g, 99%). $^1$H NMR (400 MHz, chloroform-d) δ 2.76-2.67 (m, 1H), 2.65-2.56 (m, 1H), 2.33-2.21 (m, 1H), 2.17-2.08 (m, 3H), 1.93 (dtd, J=14.5, 9.9, 5.2 Hz, 1H), 1.84-1.74 (m, 2H), 1.70-1.52 (m, 3H), 1.48 (s, 9H).

Intermediate S-3: (2R,3S)-3-(tert-Butoxycarbonyl)-6,6,6-trifluoro-2-(3-fluoropropyl)hexanoic acid

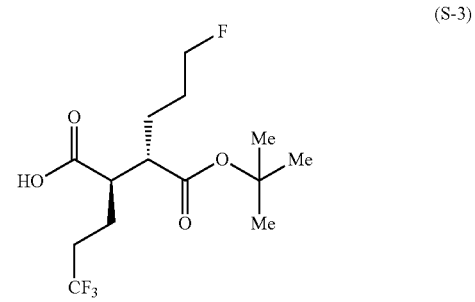 [SMILES: CC(C)(C)OC(=O)[C@@H](CCCF)[C@@H](CCC(F)(F)F)C(=O)O]

Intermediate S-3A: 3-Fluoropropyltrifluoromethanesulfonate

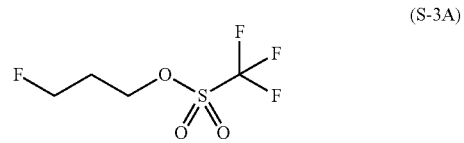 [SMILES: O=S(=O)(OCCCF)C(F)(F)F]

To a cold (−25° C.), stirred solution of 2,6-lutidine (4.60 mL, 39.5 mmol) in DCM (30 mL) was added triflic anhydride (6.00 mL, 35.5 mmol) over 3 min. Then 3-fluoropropane-1-ol (1.61 g, 20.6 mmol) was added. The reaction mixture was warmed to room temperature for 2.5 h. The reaction mixture was then concentrated to half its volume and purified by flash chromatography (Teledyne ISCO CombiFlash, isocratic DCM, REDISEP® SiO$_2$ 120 g, detecting at 254 nM, and monitoring at 220 nM). Concentration of the appropriate fractions provided Intermediate S-3A (2.92 g, 67.4%). $^1$H NMR (400 MHz, chloroform-d) δ ppm 4.69 (2 H, t, J=6.16 Hz), 4.65 (1 H, t, J=5.50 Hz), 4.54 (1 H, t, J=5.61 Hz), 2.25 (1 H, dt, J=11.39, 5.86 Hz), 2.19 (1 H, dt, J=11.44, 5.94 Hz)

Intermediate S-3: (2R,3S)-3-(tert-Butoxycarbonyl)-6-fluoro-2-(3,3,3-trifluoropropyl) hexanoic acid, and Intermediate S-3B: (2R,3R)-3-(tert-Butoxycarbonyl)-6-fluoro-2-(3,3,3-trifluoropropyl)hexanoic acid

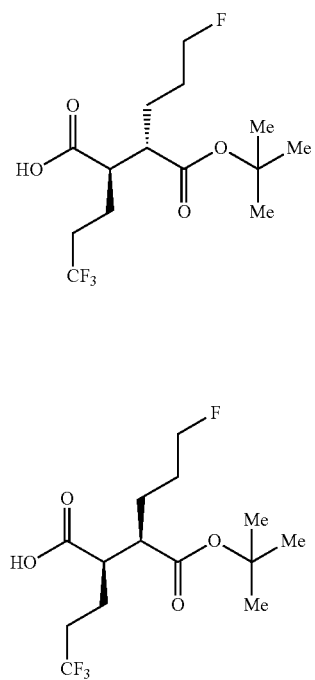

To a cold (−78° C.), stirred solution of Intermediate S-1D (1.01 g, 3.73 mmol) in THF (15 mL) was slowly added LDA (4.56 mL, 8.21 mmol) over 5 min. After stirring for 1.5 h, Intermediate S-3A (1.02 g, 4.85 mmol) was added to the reaction mixture over 3 min. After 17 min, the reaction mixture was warmed to −25° C. bath (ice/MeOH/dry ice) for 1.5 h. The reaction was quenched with water (15 mL) and was then extracted with CH$_2$Cl$_2$ (3×20 mL). The organic layer was again extracted with 1N NaOH (3×20 mL) and the aqueous layers were combined. The aqueous layer was cooled in ice/water bath and then acidified with 6N HCl to pH 1. Next, the aqueous layer was saturated with solid NaCl and extracted with EtOAc (2×85 mL). The combined organics were washed with brine, dried over anhydrous magnesium sulfate, and concentrated under reduced pressure to provide a mixture of Intermediate S-3 and Intermediate S-3B (0.96 g, 78%) as an oil. $^1$H NMR (400 MHz, chloroform-d) δ ppm 4.48-4.56 (1 H, m), 4.36-4.44 (1 H, m), 2.75-2.83 (1 H, m), 2.61-2.72 (1 H, m), 2.08-2.34 (2 H, m), 1.83-1.98 (3 H, m), 1.66-1.82 (4 H, m), 1.44-1.51 (9 H, m). $^1$H NMR showed a 1:6.4 mixture diastereomers (Intermediate S-3:Intermediate S-3B) by integration of the peaks for the t-Bu groups.

Intermediate S-3: (2R,3S)-3-(tert-Butoxycarbonyl)-6,6,6-trifluoro-2-(3-fluoropropyl)hexanoic acid, and Intermediate S-3B: (2R,3R)-3-(tert-Butoxycarbonyl)-6-fluoro-2-(3,3,3-trifluoropropyl)hexanoic acid

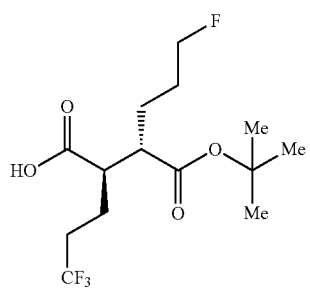

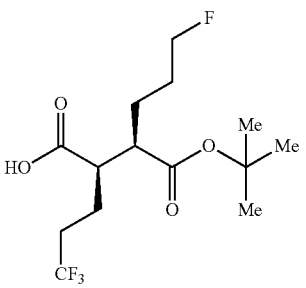

A mixture of Intermediate S-3 and Intermediate S-3B (0.30 g, 0.91 mmol) was taken in THF (5 mL) to give a colorless solution which was cooled to −78° C. Then, LDA (1.11 mL, 2.00 mmol) (1.8M in heptane/THF/ethylbenzene) was slowly added to the reaction mixture over 3 min. After stirring for 15 min the reaction mixture was placed in a room temperature water bath. After 15 min the reaction mixture was placed back in −78° C. bath and then diethylaluminum chloride (1.91 mL, 1.91 mmol) (1M in hexane) was added slowly over 5 min. The reaction mixture was stirred at −78° C. After 15 min the reaction mixture was placed in a room temperature water bath for 10 min and then cooled back to −78° C. bath. After 15 min the reaction was quenched with MeOH (5.51 mL, 136 mmol), removed from the −78° C. bath and concentrated. To the reaction mixture was added ice and HCl (8.17 mL, 8.17 mmol) then extracted with EtOAc (2×). The organic layer was washed with potassium fluoride (0.48 g, 8.26 mmol) in 16 mL H$_2$O and 10.0 mL of 1N HCl. The organics were dried over anhydrous magnesium sulfate and concentrated under reduced pressure to provide a mixture of Intermediate S-3 and Intermediate S-3B (0.20 g, 65% yield) as a light yellow oil. $^1$H NMR (400 MHz, chloroform-d) δ ppm 4.47-4.56 (1 H, m), 4.33-4.43 (1 H, m), 2.59-2.76 (2 H, m), 2.21-2.35 (1 H, m), 2.06-2.19 (1 H, m), 1.88-2.00 (1 H, m), 1.59-1.85 (6 H, m), 1.47 (9 H, s). ¹H NMR showed a 9:1 ratio in favor of the desired diastereomer Intermediate S-3.

Intermediate S-4: (2R,3S)-3-(tert-Butoxycarbonyl)-5,5-difluoro-2-(3,3,3-trifluoropropyl)hexanoic acid

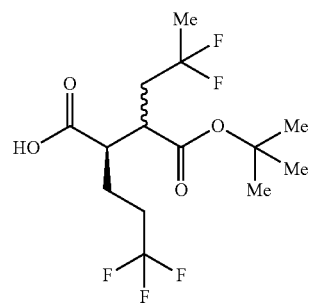

(S-4)

Intermediate S-4A: Benzyl 4,4-difluoropentanoate

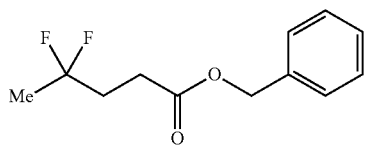

(S-4A)

DAST (19.22 mL, 145 mmol) was added dropwise to a cold (0° C.) solution of benzyl 4-oxopentanoate (20 g, 97 mmol) in DCM (120 mL). The mixture was allowed to warm to room temperature and then heated at 40° C. for 72 hours. The mixture was poured slowly into ice and saturated aqueous sodium bicarbonate mixture. The mixture was stirred for 30 minutes until no more gas was generated from solution. The organic layer was separated and the aqueous solution was extracted with DCM (2×240 mL). The combined organic extracts were dried (MgSO₄), and the solvent was carefully removed under reduced pressure. The crude material was purified by ISCO (120 g column) eluted with 100% hexane to 40% EtOAc in hexane to afford the product Intermediate S-4A (7.87 g, 34.5 mmol, 35.6% yield) as yellow oil. ¹H NMR (400 MHz, chloroform-d) δ ppm 7.29-7.51 (5 H, m), 5.17 (2 H, s), 2.53-2.67 (2 H, m), 2.14-2.36 (2 H, m), 1.63 (3 H, t, J=18.38 Hz).

Intermediate S-4B: 4-Difluoropentanoic acid

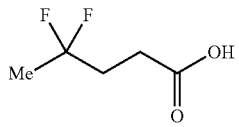

(S-4B)

To a solution of Intermediate S-4A (5000 mg, 21.91 mmol) in THF (45 mL) and MeOH (15 mL) was added LiOH (32.9 mL, 32.9 mmol) and then the mixture was stirred at room temperature for 1 hour. The reaction mixture was concentrated to remove the organics, diluted with water (10 mL), and extracted with DCM (20 ml). The aqueous layer was acidified to pH 2 with 1N HCl, and then extracted 3×20 mL DCM. The combined organic phases were dried over Na₂SO₄ and then concentrated under reduced pressure to obtain Intermediate S-4B (2062 mg, 14.93 mmol, 68.2% yield) as a yellow oil. ¹H NMR (400 MHz, chloroform-d) δ ppm 11.20-11.61 (1 H, m), 2.58 (2 H, t, J=7.81 Hz), 2.10-2.32 (2 H, m, J=16.18, 16.18, 8.03, 7.81 Hz), 1.63 (3 H, t, J=18.38 Hz).

Intermediate S-4C: 4-Difluoropentanoic acid

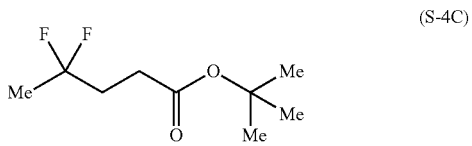 [SMILES: CC(F)(F)CCC(=O)OC(C)(C)C]

(S-4C)

To a cool (0° C.) (pre-cooled for at least 15 min), stirred solution of Intermediate S-4B (700 mg, 5.07 mmol) in n-hexane (6 mL) and THF (6 mL) under N₂ was added tert-butyl 2,2,2-trichloroacetimidate (1.814 mL, 10.14 mmol) portion-wise over 5 min and stirred for 15 min. Boron trifluoride diethyl etherate (0.065 mL, 0.512 mmol) was added and the reaction mixture was allowed to warm to room temperature as the bath warmed overnight. To the clear reaction mixture was added NaHCO₃ (3 g) and the suspension was stirred for 60 min. The suspension was filtered through MgSO₄, and washed with 300 mL hexane. The filtrate was allowed to sit for 30 min, and the resulting solid was filtered through the same MgSO₄ filter, and washed with hexane (100 mL). The filtrate was concentrated and the crude material was purified by ISCO (40 g column) eluting with 100% hexane to 50% EtOAc in hexane to afford the product Intermediate S-4C (519 mg, 2.67 mmol, 52.7% yield) as a light yellow oil. ¹H NMR (400 MHz, chloroform-d) δ ppm 2.34 (2 H, d, J=8.14 Hz), 2.01-2.16 (2 H, m), 1.53 (3 H, t, J=18.38 Hz), 1.38 (9 H, s).

Intermediate S-4D: (3R)-tert-Butyl 2-(2,2-difluoropropyl)-6,6,6-trifluoro-3-((S)-4-isopropyl-2-oxoox-azolidine-3-carbonyl)hexanoate

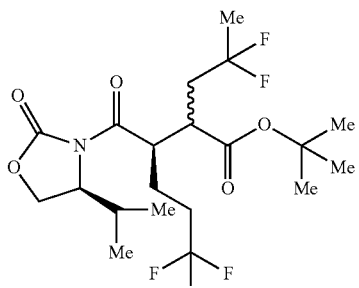

(S-4D)

Intermediate S-4D (279 mg, 0.607 mmol, 45.3% yield) was prepared from Intermediate S-4C (455 mg, 2.343 mmol) and Intermediate S-1G (358 mg, 1.339 mmol), by the methods described for Intermediate S-1H to afford a 1.2:1 mixture of diastereomers. ¹H NMR (400 MHz, chloroform-d) δ ppm 4.43-4.53 (2 H, m), 4.22-4.36 (4 H, m), 4.03-4.11 (1 H, m), 3.02-3.10 (1 H, m), 2.93-3.02 (1 H, m), 2.48-2.65 (1 H, m), 2.35-2.49 (2 H, m), 2.23-2.35 (1 H, m), 1.91-2.23 (3 H, m), 1.74-1.89 (2 H, m), 1.53-1.70 (3 H, m), 1.42-1.51 (9 H, m).

Intermediate S-4: (2R,3S)-3-(tert-Butoxycarbonyl)-5,5-difluoro-2-(3,3,3-trifluoropropyl)hexanoic acid

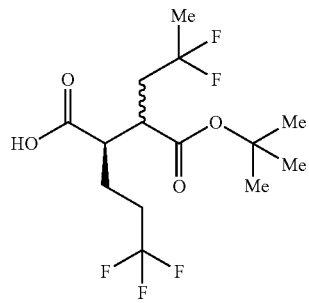

(S-4)

To a cool (0° C.), stirred solution of Intermediate S-4D (279 mg, 0.607 mmol) in THF (9 mL) and water (3 mL) was added H$_2$O$_2$ (0.375 mL, 6.12 mmol) followed by LiOH (44.1 mg, 1.840 mmol). The reaction mixture was gradually warmed to room temperature and stirred for 3 h. A solution of saturated aqueous Na$_2$SO$_3$ (5 mL) and 10 mL saturated NaHCO$_3$ was added. The mixture was stirred for 5 min, and then the reaction mixture was partially concentrated. The mixture was extracted with DCM (15 mL) and the aqueous phase was acidified to pH ~2, saturated with NaCl, and extracted with DCM (2×30 mL). The combined extracts were dried over MgSO$_4$, filtered and concentrated to give Intermediate S-4 as a 1.2:1 mixture diastereomers (169 mg, 0.485 mmol, 80% yield) as a light yellow oil. $^1$H NMR (400 MHz, chloroform-d) δ ppm 2.89-3.04 (1 H, m), 2.68-2.86 (1 H, m), 2.38-2.60 (2 H, m), 2.19-2.38 (1 H, m), 2.07-2.20 (1 H, m), 1.87-2.03 (2 H, m), 1.73-1.88 (1 H, m), 1.63 (3 H, t, J=18.49 Hz), 1.37-1.53 (9 H, m).

Intermediate S-5: (2R)-3-(tert-Butoxycarbonyl)-2-(2,2-difluoropropyl)-6,6,6-trifluorohexanoic acid

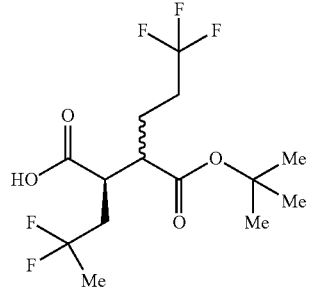

(S-5)

Intermediate S-5A: (S)-4-Benzyl-3-(4,4-difluoropentanoyl)oxazolidin-2-one

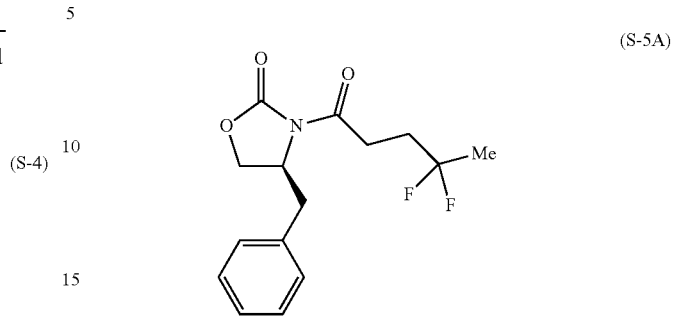

(S-5A)

In a 100 mL round-bottomed flask was added 4,4-difluoropentanoic acid (1.7 g, 12.31 mmol) and DMF (0.019 mL, 0.246 mmol) in DCM (9 mL) to give a colorless solution. Oxalyl chloride (1.077 mL, 12.31 mmol) was added slowly and the resulting mixture was stirred at room temperature for 3 hours. The resulting mixture was concentrated to dryness. A separate 100 mL round-bottomed flask was charged with (S)-4-benzyloxazolidin-2-one (2.181 g, 12.31 mmol) in THF (23 mL) and then cooled to −78° C. Next, n-BuLi (4.92 mL, 12.31 mmol) was added slowly over 5 min. A solution of the above acid chloride in THF (10 mL) was slowly added to the reaction at −78° C. The reaction mixture was stirred at −78° C. for about 1 h and then allowed to warm to room temperature and stirred under nitrogen overnight. The reaction mixture was quenched with about 60 mL of saturated aqueous NH$_4$Cl solution. The resulting mixture was diluted with 200 mL of EtOAc and about 60 mL of water. The layers were separated and the aqueous layer was extracted with 250 mL of EtOAc. The combined EtOAc extracts were dried (MgSO$_4$), filtered and concentrated in vacuo to give a dark yellowish oil. The crude material was purified by silica gel chromatography (80 g ISCO column. A: hexane, B: DCM, 20% to 100% elution) to give Intermediate S-5A (1.65 g, 5.55 mmol, 45.1% yield). $^1$H NMR (400 MHz, chloroform-d) δ ppm 7.23-7.39 (3 H, m), 7.17-7.24 (2 H, m), 4.67 (1 H, ddd, J=9.85, 3.69, 3.41 Hz), 4.13-4.26 (2 H, m), 3.29 (1 H, dd, J=13.42, 3.30 Hz), 3.16 (2 H, ddd, J=13.98, 8.47, 6.82 Hz), 2.77 (1 H, dd, J=13.31, 9.57 Hz), 2.19-2.41 (2 H, m), 1.53-1.75 (3 H, m).

Intermediate S-5B: (S)-tert-Butyl 3-((S)-4-benzyl-2-oxooxazolidine-3-carbonyl)-5,5-difluorohexanoate

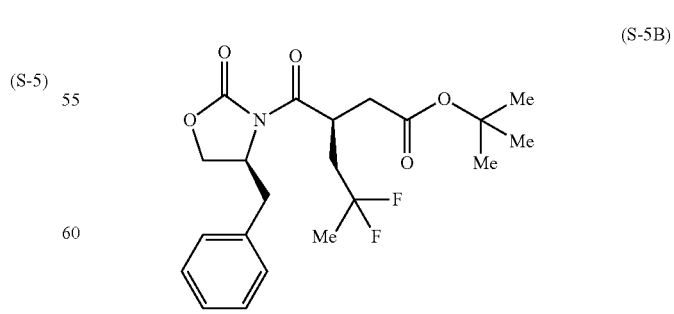

(S-5B)

In a 200 mL round-bottomed flask was added Intermediate S-5A (1.67 g, 5.62 mmol) in THF (20 mL) to give a colorless solution. The solution was cooled to −78° C., and then NaH- MDS (6.74 mL, 6.74 mmol) 1M in THF was slowly added to the reaction mixture at −78° C. over 8 min. The mixture was stirred at −78° C. for 20 mins, and then tert-butyl 2-bromoacetate (1.648 mL, 11.23 mmol) was added slowly over 5 min. The mixture was stirred at −78° C. while the bath slowly warm to room temperature and then stirring was continued overnight. The reaction was quenched with aqueous saturated NH₄Cl and extracted with EtOAc. The combined organic layers were dried over MgSO₄, filtered and concentrated. The crude product was purified on by silica gel chromatography (330 g column, ISCO) eluting with a gradient from 5% EtOAc/hexane to 50% EtOAc/hexane. Fractions were combined and concentrated in vacuo to give Intermediate S-5B (1.73 g, 4.20 mmol, 74.9% yield). $^1$H NMR (400 MHz, chloroform-d) δ ppm 7.30-7.39 (2 H, m), 7.26 (3 H, d, J=1.98 Hz), 4.60-4.73 (1 H, m), 4.42-4.55 (1 H, m), 4.16 (2 H, s), 3.26-3.39 (1 H, m), 2.68-2.86 (2 H, m), 2.51-2.62 (1 H, m), 2.32-2.51 (1 H, m), 2.04 (1 H, s), 1.66 (3 H, t, J=18.60 Hz), 1.44 (9 H, s).

Intermediate S-5C: (S)-2-(2-tert-Butoxy-2-oxoethyl)-4,4-difluoropentanoic acid

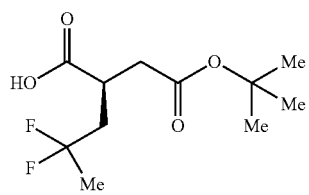

(S-5C)

A solution of Intermediate S-5C (1.5 g, 3.65 mmol) in THF (15 mL) was cooled to 0° C. A separate solution of LiOH (0.262 g, 10.94 mmol) and H₂O₂ (2.011 mL, 32.8 mmol) in water (5 mL) was prepared. The LiOH/H₂O₂ solution was added to the THF mixture, and stirred in an ice/water bath for 30 mins. The reaction mixture was removed from the ice bath and warmed to room temperature. The reaction mixture was stirred from an additional 2 hr and then cooled in an ice/water bath. To the mixture was added saturated aqueous NaHCO₃ (30 mL) and saturated aqueous Na₂SO₃ (30 mL), and the reaction mixture was stirred in an ice bath for 1 hour. The THF was removed under reduced pressure, and the aqueous layer was extracted with DCM. The aqueous layer was acidified to pH 2 with conc. HCl, and then extracted with EtOAc. The combined organic layers were washed with brine and then dried over MgSO₄. The suspension was then filtered and concentrated to a thick colorless oil, and dried under vacuum to obtain the product Intermediate S-5C (837 mg, 3.32 mmol, 91% yield). $^1$H NMR (400 MHz, chloroform-d) δ ppm 3.01-3.14 (1 H, m), 2.55-2.74 (2 H, m), 2.33-2.51 (1 H, m), 2.05 (1 H, s), 1.64 (3 H, t, J=18.49 Hz), 1.44 (9 H, s).

Intermediate S-5D: 3,3,3-Trifluoropropyl trifluoromethanesulfonate

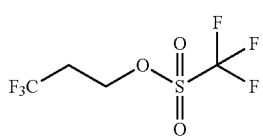

(S-5D)

To a cold (−25° C.), stirred solution of 2,6-lutidine (18.38 mL, 158 mmol) in DCM (120 mL) was added Tf₂O (24.88 mL, 147 mmol) over 3 min, and the mixture was stirred for 5 min. To the reaction mixture was added 3,3,3-trifluoropropan-1-ol (12 g, 105 mmol) over an interval of 3 min. After 2 hr, the reaction mixture was warmed to room temperature and stirred for 1 hr. The reaction mixture was concentrated to half its volume, then purified by loading directly on a silica gel column (330 g ISCO) and the product was eluted with DCM to afford Intermediate S-5D (13.74 g, 53%) as a colorless oil. $^1$H NMR (400 MHz, CDCl₃) δ ppm 4.71 (2 H, t, J=6.15 Hz), 2.49-2.86 (2 H, m).

Intermediate S-5: ((2R,3S)-3-(tert-Butoxycarbonyl)-2-(2,2-difluoropropyl)-6,6,6-trifluorohexanoic acid

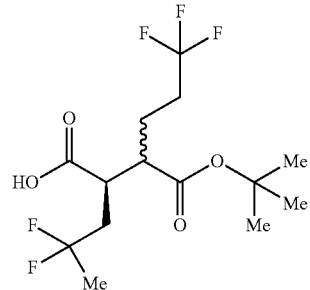

(S-5)

To a 50 mL round-bottomed flask was added Intermediate S-5C (500 mg, 1.982 mmol) in THF (10 mL) to give a colorless solution and which was then cooled to −78° C. LDA (2.423 mL, 4.36 mmol) was added slowly to the reaction over 5 min. The reaction mixture was then stirred at −78° C. for 3 h. Intermediate S-5D (634 mg, 2.58 mmol) was added to the reaction dropwise over 3 min, and stirring was continued at −78° C. for 30 min. The reaction mixture was then warmed to −15° C. (ice/methanol bath) and maintained at −15° C. for 1 hour. The reaction mixture was then quenched with 20 mL of water. Next, the majority of the THF was removed under reduced pressure and then, 1N NaOH (1 mL) was added and the aqueous phase was extracted with DCM. The DCM layer was extracted with 1N NaOH (2×20 mL). The pooled aqueous phases were cooled to 0° C. and acidified with 6M HCl and then extracted with ethyl acetate. The combined organic layers were washed with brine, dried over MgSO₄, and then filtered and concentrated. The crude product was purified by column chromatography (ISCO) 80 g column and eluted with 10% EtOAc in hexane to 100% EtOAc in 23 min to obtain the Intermediate S-5 as a 1.2:1 mixture of diastereomers (213 mg, 0.612 mmol, 30.9% yield).

Example 1

(2R,3S)-N-((3S)-2-Oxo-5-phenyl-1-(2-pyridinyl)-2,3-dihydro-1H-1,4-benzodiazepin-3-yl)-3-(4,4,4-trifluorobutyl)-2-(3,3,3-trifluoropropyl)succinamide

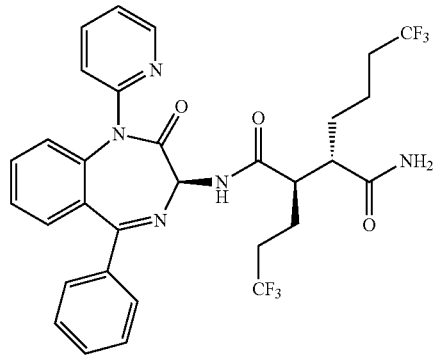

(1)

Intermediate 1A: Benzyl 2-oxo-5-phenyl-1-(pyridin-2-yl)-2,3-dihydro-1H-benzo[e][1,4]diazepin-3-ylcarbamate

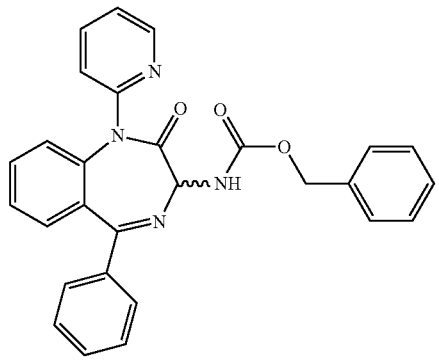

(1A)

To a stirred mixture of benzyl 2-oxo-5-phenyl-2,3-dihydro-1H-benzo[e][1,4]diazepin-3-ylcarbamate (1.20 g, 3.11 mmol, prepared according to *J. Med. Chem.*, 49:2311-2319 (2006), compound #4a), 2-iodopyridine (1.00 g, 4.88 mmol), cuprous iodide (0.15 g, 0.788 mmol) and $Cs_2CO_3$ (3.05 g, 9.36 mmol) in dioxane (25 mL) was added (+/−)-trans-1,2-diaminocyclohexane (0.19 mL, 1.58 mmol) under nitrogen. The reaction mixture was then heated to 120° C. and gently refluxed for 10 min. It was then cooled to room temperature under nitrogen. This mixture was diluted with 100 mL of EtOAc, 40 mL of pH 4 phosphate buffer and 40 mL of saturated $NaHCO_3$ solution. The insoluble material was removed by filtration through a 2 inch pad of CELITE®, and rinsed with EtOAc (2×30 mL). The aqueous phase was separated and extracted with 160 mL of EtOAc. The combined EtOAc extracts were washed with saturated $NaHCO_3$ solution (1×30 mL) and brine (1×20 mL), then dried ($MgSO_4$), filtered and concentrated in vacuo. The residue was purified by silica gel chromatography (hexane/EtOAc) to afford Intermediate 1A (0.88 g, 61%): $^1H$ NMR (400 MHz, DMSO-$d_6$) δ 8.61 (1 H, d, J=8.14 Hz), 8.47 (1 H, dd, J=4.73, 1.21 Hz), 7.94-8.03 (1 H, m), 7.64 (2 H, d, J=7.92 Hz), 7.47-7.60 (4 H, m), 7.27-7.44 (9 H, m), 6.97 (1 H, d, J=8.14 Hz), 5.39 (1 H, d, J=8.36 Hz), 5.10 (2 H, s); HPLC: RT=2.930 min (CHROMOLITH® ODS 4.6×50 mm (4 min grad) eluting with 10-90% aqueous MeOH over 4 minutes containing 0.% TFA, 4 mL/min, monitoring at 220 nm); MS(ES): m/z=463.3 [M+H]$^+$.

Intermediate 1B: (S)-3-Amino-5-phenyl-1-(pyridin-2-yl)-1H-benzo[e][1,4]diazepin-2(3H)-one

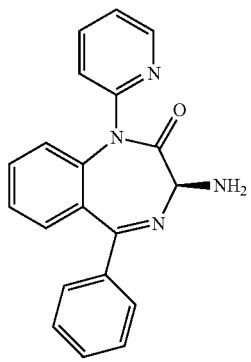

(1B)

Intermediate 1A (5.24 g, 11.33 mmol) and 33% HBr/HOAc (50 mL, 11.33 mmol) were combined and stirred at room temperature for 2 h. The reaction mixture was diluted with 300 mL of ether. The resulting precipitate was collected by filtration, rinsed with ether (2×50 mL), then dried under vacuum. The solid was dissolved in 100 mL of water and made basic by the addition of solid $NaHCO_3$. The mixture was extracted with EtOAc (2×200 mL), and the combined organic extracts were washed with water (1×40 mL) and brine (1×50 mL), then dried ($MgSO_4$), filtered and concentrated in vacuo to give the crude racemic amine. This solid was purified by preparative SFC chromatography (Berger SFC MGII, AD-H 250×30 mm ID, 5 μm, 78/22 $CO_2$/MeOH with 0.1% DEA, 85 mL/min). After the fractions containing product were concentrated and dried overnight under vacuum, Intermediate 1B (1.576 g, 42.4%) was obtained as a colorless solid: $^1H$ NMR (400 MHz, DMSO-$d_6$) δ 8.47 (1 H, dd, J=4.73, 1.65 Hz), 7.98 (1 H, td, J=7.70, 1.98 Hz), 7.62 (3 H, dd, J=14.75, 7.48 Hz), 7.45-7.57 (5 H, m), 7.26-7.43 (3 H, m), 6.92 (1 H, d, J=8.14 Hz), 4.57 (1 H, br. s.), 2.67 (1 H, br. s.); Chiral HPLC: RT=5.160 min (Berger SFC, AD-H 250×4.6 mm ID, 5 μm, 75/25 $CO_2$/MeOH with 0.1% DEA, 2.0 mL/min); HPLC: RT=1.290 min (CHROMOLITH® ODS 4.6×50 mm (4 min grad) eluting with 10-90% aqueous MeOH over 4 minutes containing 0.% TFA, 4 mL/min, monitoring at 220 nm); MS(ES): m/z=329.0 [M+H]$^+$.

Intermediate 1C: (2S,3R)-tert-Butyl 6,6,6-trifluoro-3-(((S)-2-oxo-5-phenyl-1-(pyridin-2-yl)-2,3-dihydro-1H-benzo[e][1,4]diazepin-3-yl)carbamoyl)-2-(4,4,4-trifluorobutyl)hexanoate

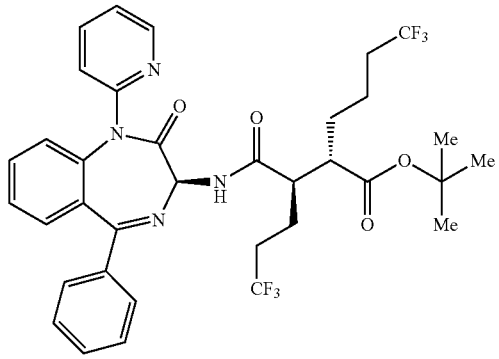

(1C)

A solution of Intermediate 1B (60 mg, 0.183 mmol), Intermediate S-2 (90 mg, 0.238 mmol), and $Et_3N$ (0.033 mL, 0.238 mmol) in DMF (1 mL) was treated with o-benzotriazol-1-yl-N,N,N',N'-tetramethyluronium tetrafluoroborate (64.5 mg, 0.201 mmol). The mixture was stirred at room temperature for 3 h and then water and some sat aq $NaHCO_3$ were added. The resulting mixture was extracted with EtOAc (2×) and the combined organic layers were concentrated to dryness. The crude product was purified by silica gel column chromatography (40 g ISCO column) eluting with a gradient from 100% DCM to 40% EtOAc/DCM to afford Intermediate 1C (63 mg, 50%). HPLC: RT=3.531 min (CHROMOLITH® ODS 4.6×50 mm (3 min grad) eluting with 10-90% aqueous MeOH over 4 minutes containing 0.% TFA, 4 mL/min, monitoring at 220 nm); MS(ES): m/z=691 [M+H]$^+$.

Intermediate 1D: (2S,3R)-6,6,6-Trifluoro-3-(((S)-2-oxo-5-phenyl-1-(pyridin-2-yl)-2,3-dihydro-1H-benzo[e][1,4]diazepin-3-yl)carbamoyl)-2-(4,4,4-trifluorobutyl)hexanoic acid

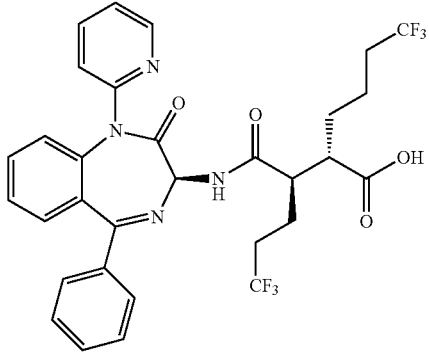

(1D)

A solution of Intermediate 1C (62 mg, 0.090 mmol) in DCM (1 mL) was treated with TFA (1 mL). The reaction mixture was stirred at room temperature for 1.5 h and then concentrated to dryness to afford Intermediate 1D (67 mg, 100%). HPLC: RT=3.011 min (CHROMOLITH® ODS 4.6×50 mm (3 min grad) eluting with 10-90% aqueous MeOH over 4 minutes containing 0.% TFA, 4 mL/min, monitoring at 220 nm); MS(ES): m/z=634 [M+H]$^+$.

Example 1

A solution of Intermediate 1D (67 mg, 0.090 mmol), HOBT (20.62 mg, 0.135 mmol), EDC (25.8 mg, 0.135 mmol) and ammonium chloride (28.8 mg, 0.539 mmol) in DMF (1 mL) was treated with (0.141 mL, 0.808 mmol) and the mixture was stirred at room temperature overnight. Water was added to the reaction mixture and an off-white precipitate formed. The solid was collected by filtration and rinsed with water and dried under vacuum. The crude material was purified by preparative HPLC (Column: CHIRALPAK® AD 4.6×250 mm, 13% (1:1, MeOH/EtOH)/heptane, Flow=1 mL/min) to afford Example 1 (39 mg, 68%). HPLC: RT=10.001 min (H$_2$O/CH$_3$CN with TFA, SunFire C18 3.5 µm, 4.6×150 mm, gradient=15 min, wavelength=220 and 254 nm); MS(ES):m/z=634[M+H]$^+$; $^1$H NMR (500 MHz, DMSO-d$_6$) δ 9.55 (1 H, d, J=6.94 Hz), 8.44-8.52 (1 H, m), 8.00 (1 H, td, J=7.77, 1.94 Hz), 7.65-7.72 (2 H, m), 7.48-7.64 (6 H, m), 7.32-7.45 (3 H, m), 6.95-7.10 (2 H, m), 5.55 (1 H, d, J=7.21 Hz), 2.78 (1 H, td, J=9.92, 4.86 Hz), 2.44 (1 H, td, J=10.61, 2.91 Hz), 2.07-2.34 (3 H, m), 1.29-1.71 (7 H, m).

Example 2
(2R,3S)-N-((3S)-1-(5-Chloro-2-pyridinyl)-2-oxo-5-phenyl-2,3-dihydro-1H-1,4-benzodiazepin-3-yl)-2,3-bis(3,3,3-trifluoropropyl)succinamide

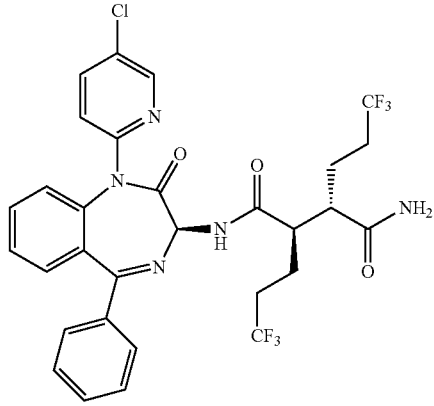

(2)

Intermediate 2A: 3-Amino-1-(5-chloropyridin-2-yl)-5-phenyl-1H-benzo[e][1,4]diazepin-2(3H)-one

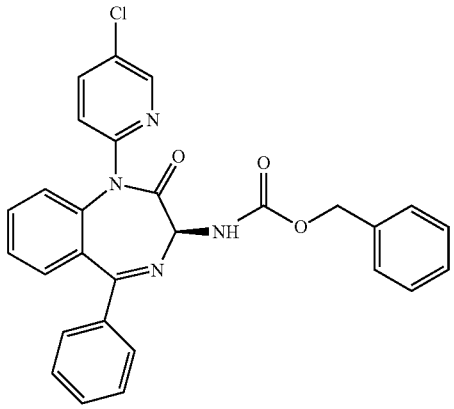

(2A)

Intermediate 2A was prepared as described in Intermediate 1A using 5-chloro-2-iodopyridine. The racemate was purified by preparative SFC chromatography (Berger SFC MGII, CHIRALCEL® OJ-H 250×30 mm ID, 5 µm, 80/20 CO$_2$/MeOH, 85 mL/min) to give Intermediate 3A. RT=3.44 min (H$_2$O/CH$_3$OH with TFA, CHROMOLITH® ODS S5 4.6×50 mm, gradient=3 min, wavelength=220 and 254 nm); MS(ES):m/z=497 [M+H$^+$].

Intermediate 2B: 3-Amino-1-(5-chloropyridin-2-yl)-5-phenyl-1H-benzo[e][1,4]diazepin-2(3H)-one

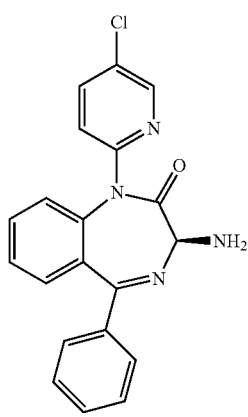

(2B)

Intermediate 2B was prepared from Intermediate 2A (0.78 g, 1.56 mmol) and 33% HBr in acetic acid (15 mL) according to the procedure described for Intermediate 1B to afford Intermediate 2B (0.56 g, 99%). RT=2.43 min (H$_2$O/CH$_3$OH with TFA, CHROMOLITH® ODS S5 4.6×50 mm, gradient=3 min, wavelength=220 and 254 nm); MS(ES):m/z=363 [M+H$^+$].

Example 2

Example 2 was prepared from Intermediate 2B and Intermediate S-1 according to the general procedure shown for Example 1. HPLC: RT=10.96 min (H₂O/CH₃CN with TFA, SunFire C18 3.5 μm, 4.6×150 mm, gradient=15 min, wavelength=220 and 254 nm); MS(ES):m/z=654.4 [M+H⁺]; ¹H NMR (500 MHz, DMSO-d₆) δ 9.61 (d, J=7.5 Hz, 1H), 8.54 (d, J=2.5 Hz, 1H), 8.14 (dd, J=8.6, 2.8 Hz, 1H), 7.70 (d, J=8.6 Hz, 1H), 7.66-7.63 (m, 3H), 7.62-7.56 (m, 2H), 7.53-7.47 (m, 2H), 7.45-7.35 (m, 2H), 7.13 (br. s., 1H), 7.04 (d, J=8.0 Hz, 1H), 5.60 (d, J=7.2 Hz, 1H), 2.85 (td, J=10.3, 4.0 Hz, 1H), 2.54 (br. s., 1H), 2.46-2.38 (m, 1H), 2.29-2.21 (m, 1H), 2.17 (dd, J=19.7, 8.6 Hz, 3H), 1.80-1.70 (m, 1H), 1.68-1.56 (m, 2H).

Example 3

(2R,3S)-N-((7S)-6-Oxo-9-phenyl-5-(2-pyridinyl)-6,7-dihydro-5H-[1,3]dioxolo[4,5-h][1,4]benzodiazepin-7-yl)-2,3-bis(3,3,3-trifluoropropyl)succinamide

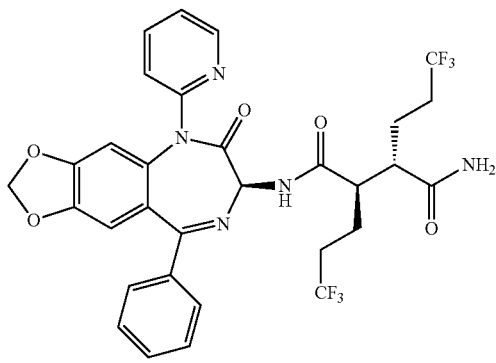

(3)

Intermediate 3A:
6,7-Diphenyl-5H-[1,3]dioxolo[4,5-f]indole

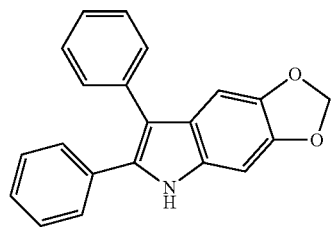

(3A)

A flask equipped with a Dean-Stark apparatus was charged with 3,4-(methylenedioxy)aniline (5.0 g, 36.4 mmol), p-toluenesulfonic acid (245 mg, 1.2 mmol), benzoin (5.20 g, 24.4 mmol), and xylene (30 mL). The mixture was heated to reflux for 10 hours, then cooled to room temperature. The reaction mixture was diluted with chloroform, then washed twice with 10% sulfuric acid, once with water, and once with brine. The organic layer was concentrated to a minimum volume and petroleum ether was added. The mixture was stirred well and then the precipitated solid was filtered off and dried to give Intermediate 3A (7.0 g, 92%). HPLC: RT=2.261 min (H₂O/MeCN with NH₄OAc, PUROSPHER® Star RP-18 3 μM, 4×55 mm, gradient=3 min, wavelength=220 nm); MS(ES, negative ionization): m/z=312 [M−H]⁻.

Intermediate 3B:
N-(6-Benzoylbenzo[d][1,3]dioxol-5-yl)benzamide

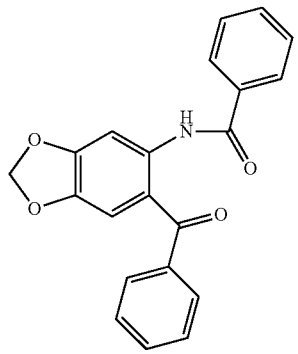

(3B)

To a solution of Intermediate 3A (7.0 g, 22 mmol) in AcOH (140 mL) was added a solution of ammonium molybdate (67 mg, 0.054 mmol) in water (6.7 mL). This mixture was heated to 65° C., then H₂O₂ (30% in H₂O, 8.93 mL, 78.8 mmol) was added dropwise over approximately 15 minutes. After 2 h, the reaction mixture was cooled to room temperature and diluted with water. The solid was filtered off, washed with water, and dried to give Intermediate 3B (6.0 g, 79%): ¹H NMR (400 MHz, CDCl₃) δ ppm 12.56 (s, 1H), 8.59 (s, 1H), 8.10-8.08 (m, 2H), 7.67-7.60 (m, 2H), 7.59-7.50 (m, 6H), 7.06 (s, 1H), 6.07 (s, 2H).

Intermediate 3C:
6-Aminobenzo[d][1,3]dioxol-5-yl)(phenyl)methanone

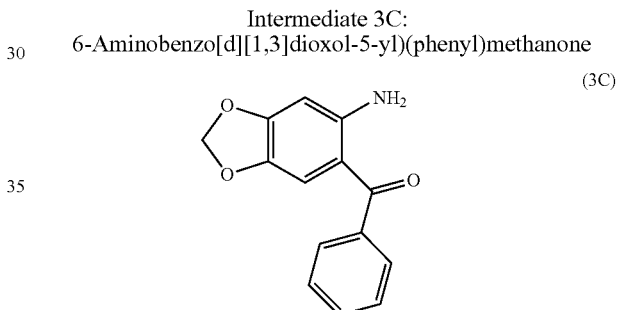

(3C)

Intermediate 3B (73 g, 0.211 mol) was dissolved in EtOH (292 mL). NaOH (50% in water, 182.5 mL, 2.28 mol) was added and then the solution was heated to reflux for 2 hours. The reaction mixture was cooled to room temperature and then diluted with water. The solid was filtered off, washed with water and dried to give Intermediate 3C (42 g, 95%). ¹H NMR (400 MHz, CDCl₃) δ ppm 7.57-7.55 (m, 2H), 7.49-7.42 (m, 3H), 6.85 (s, 1H), 6.39 (br s, 2H), 6.23 (s, 1H), 5.89 (s, 2H).

Intermediate 3D: Benzyl (6-oxo-9-phenyl-6,7-dihydro-5H-[1,3]dioxolo[4',5':4,5]benzo[1,2-e][1,4]diazepin-7-yl)carbamate

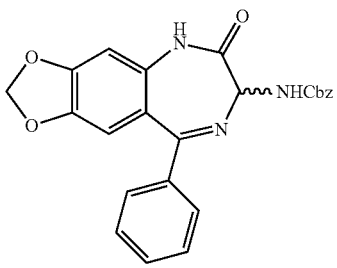

(3D)

To a solution of Intermediate 3C (7.0 g, 30 mmol) and 2-(1H-benzo[d][1,2,3]triazol-1-yl)-2-(benzyloxycarbonylamino)acetic acid (*J. Org. Chem.*, 55:2206-2214 (1990)) (12.06 g, 37 mmol) in DCM (70 mL) at 0° C. was added dicyclohexylcarbodiimide (9.16 g, 66 mmol) in DCM (70 mL). The reaction mixture was stirred at room temperature overnight, and then saturated aqueous $NaHCO_3$ was added. The layers were separated, and the aqueous layer was washed twice with DCM. The combined organic layers were washed successively with water and brine, and then dried over $Na_2SO_4$, filtered and concentrated to dryness. This material was dissolved in MeOH (140 mL) and cooled to 0° C. Ammonium hydroxide (28-30% in water, 140 mL) was added dropwise. The reaction mixture was allowed to gradually warm to room temperature. After 3 hours, the reaction mixture was cooled to 0° C., then acetic acid (140 mL) and $NH_4OAc$ (14.25 g, 184 mmol) were added. The reaction mixture was stirred overnight, then 10% aqueous NaOH was added. The solid was filtered off, washed with water, and dried to give Intermediate 3D (3.5 g, 27%). HPLC: RT=1.856 min ($H_2O$/MeCN with $NH_4OAc$, Ascentis Express C-18 2.7 μM, 2.1×50 mm, gradient=4 min, wavelength=220 nm); MS(ES): m/z=430 $[M+H]^+$.

Intermediate 3E: (S)-7-Amino-9-phenyl-5-(pyridin-2-yl)-5H-[1,3]dioxolo[4',5':4,5]benzo[1,2-e][1,4]diazepin-6(7H)-one

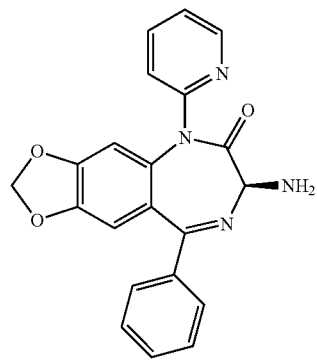

(3E)

Intermediate 3E was prepared from Intermediate 3D and 2-iodopyridine according to the procedure described for Example 1. The racemate was purified by preparative SFC chromatography (Berger SFC MGII, OD-H 250×30 mm ID, 5 μm, 73/17 $CO_2$/MeOH, 85 mL/min) to give Intermediate 4E. RT=1.668 min ($H_2O/CH_3OH$ with TFA, CHROMOLITH® ODS S5 4.6×50 mm, gradient=3 min, wavelength=220 and 254 nm); MS(ES):m/z=373.2 $[M+H^+]$.

Example 3

Example 3 was prepared from Intermediate 3E and Intermediate S-1 according to the general procedure shown for Example 1. HPLC: RT=9.70 min ($H_2O/CH_3CN$ with TFA, SunFire C18 3.5 μm, 4.6×150 mm, gradient=15 min, wavelength=220 and 254 nm); MS(ES):m/z=572.2 $[M+H^+]$; $^1H$ NMR (400 MHz, DMSO-$d_6$) δ 9.57 (d, J=7.3 Hz, 1H), 8.52-8.43 (m, 1H), 7.98 (td, J=7.8, 2.0 Hz, 1H), 7.70-7.63 (m, 3H), 7.61-7.46 (m, 4H), 7.40 (ddd, J=7.4, 4.8, 1.0 Hz, 1H), 7.15 (s, 1H), 6.83 (s, 1H), 6.56 (s, 1H), 6.14 (dd, J=5.5, 0.9 Hz, 2H), 5.63 (d, J=7.3 Hz, 1H), 2.84 (td, J=10.3, 3.9 Hz, 1H), 2.46- 2.37 (m, 1H), 2.35-2.24 (m, 1H), 2.17 (dd, J=19.3, 8.9 Hz, 3H), 1.81-1.69 (m, 2H), 1.66-1.54 (m, 2H).

Example 4

(2R,3S)-N-((3S)-2-Oxo-5-phenyl-1-(3-pyridinyl)-2,3-dihydro-1H-1,4-benzodiazepin-3-yl)-3-(4,4,4-trifluorobutyl)-2-(3,3,3-trifluoropropyl)succinamide

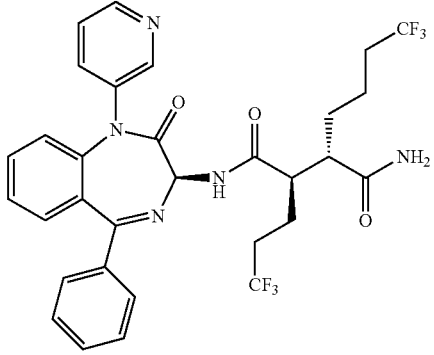

(4)

Intermediate 4A: (S)-3-Amino-5-phenyl-1-(pyridin-3-yl)-1H-benzo[e][1,4]diazepin-2(3H)-one

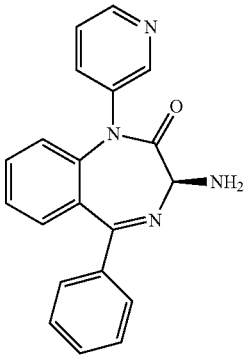

(4A)

Intermediate 4A was prepared according to the procedure outlined for Example 1 using 3-iodopyridine. The racemate was purified by preparative chiral chromatography (OJ 250× 30 mm ID, 5 μm, isocratic, 30% 1:1 EtOH:MeOH/heptane) to give Intermediate 4A. RT=1.338 min ($H_2O/CH_3OH$ with TFA, CHROMOLITH® ODS S5 4.6×50 mm, gradient=3 min, wavelength=220 and 254 nm); MS(ES):m/z=329.2 $[M+H^+]$.

Example 4

Example 4 was prepared from Intermediate 4A and Intermediate S-2 according to the general procedure shown for Example 1. HPLC: RT=8.14 min ($H_2O/CH_3CN$ with TFA, SunFire C18 3.5 μm, 4.6×150 mm, gradient=15 min, wavelength=220 and 254 nm); MS(ES):m/z=634.3. $^1H$ NMR (400 MHz, DMSO-$d_6$) δ ppm 9.55 (1 H, d, J=7.04 Hz), 8.56 (1 H, dd, J=4.73, 1.43 Hz), 8.47 (1 H, d, J=2.20 Hz), 7.69-7.77 (3 H, m), 7.56-7.65 (3 H, m), 7.47-7.56 (3 H, m), 7.35-7.43 (2 H, m), 7.07 (2 H, d, J=8.14 Hz), 5.55 (1 H, d, J=7.26 Hz), 2.74-2.84 (1 H, m), 2.52-2.58 (1 H, m), 2.40-2.48 (1 H, m), 2.08-2.35 (3 H, m), 1.54-1.69 (3 H, m), 1.27-1.52 (3 H, m).

Example 5

(2R,3S)-N-((3S)-2-Oxo-5-phenyl-1-(3-pyridinyl)-2,3-dihydro-1H-1,4-benzodiazepin-3-yl)-2,3-bis(3,3,3-trifluoropropyl)succinamide

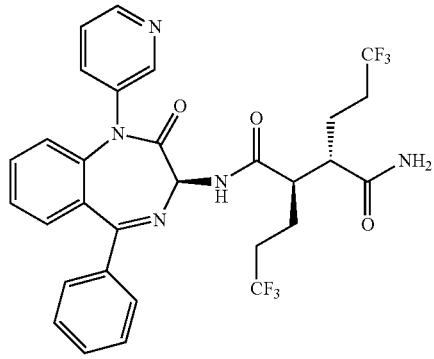

(5)

Example 5 was prepared from Intermediate 4A and Intermediate S-1 according to the general procedure shown for Example 1. HPLC: RT=7.97 min (H₂O/CH₃CN with TFA, SunFire C18 3.5 μm, 4.6×150 mm, gradient=15 min, wavelength=220 and 254 nm); MS(ES):m/z=620.3 [M+H⁺]; ¹H NMR (400 MHz, DMSO-d₆) δ ppm 9.60 (1 H, d, J=7.48 Hz), 8.56 (1 H, dd, J=4.73, 1.43 Hz), 8.49 (1 H, d, J=2.20 Hz), 7.73-7.78 (1 H, m), 7.68-7.72 (1 H, m), 7.66 (1 H, br. s.), 7.53-7.64 (4 H, m), 7.51 (2 H, d, J=8.14 Hz), 7.35-7.44 (2 H, m), 7.15 (1 H, s), 7.05 (1 H, d, J=8.14 Hz), 5.59 (1 H, d, J=7.70 Hz), 2.86 (1 H, td, J=10.29, 4.07 Hz), 2.50-2.55 (1 H, m), 2.32-2.46 (1 H, m), 2.09-2.29 (3 H, m), 1.71-1.82 (1 H, m), 1.55-1.68 (3 H, m).

Example 6

(2R,3S)-N-((3S)-1-(Cyclopropylmethyl)-5-(4-methoxyphenyl)-2-oxo-2,3-dihydro-1H-1,4-benzodiazepin-3-yl)-2,3-bis(3,3,3-trifluoropropyl)succinamide

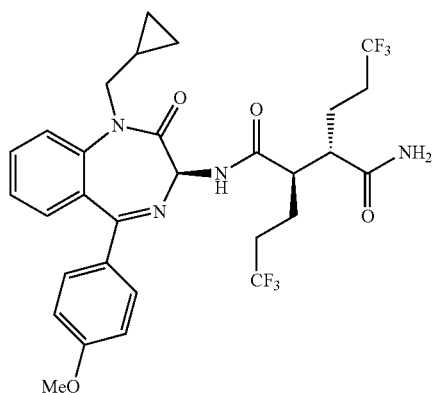

(6)

Intermediate 6A: (2-Aminophenyl)(4-methoxyphenyl)methanone

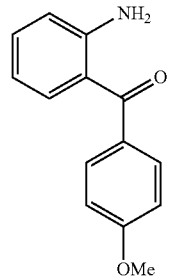

(6A)

To a 250 mL round-bottomed flask charged with magnesium (1.646 g, 67.7 mmol) and ethyl ether (47.0 ml) was added two drops of dibromoethane and the mixture was heated to reflux for 15 minutes. p-Bromoanisole (6.35 ml, 50.8 mmol) in diethyl ether (47.0 ml) was slowly added through an addition funnel while a refluxing temperature was maintained. The resulting mixture was heated for 3 hrs, and then cooled to room temperature. A solution of 2-aminobenzonitrile (2 g, 16.93 mmol) in diethyl ether (47.0 ml) was added dropwise over 15 min. After the addition, the mixture was refluxed for 16 hrs. The volume was then reduced by half under reduced pressure and the resulting mixture was quenched slowly with ice (100 g). Next, 6N HCl (10 mL) was then added and the mixture was stirred at room temperature for 16 hrs. The pH was adjusted to pH 8 with 5N NaOH and diluted with saturated NaHCO₃ (50 ml). The phases were separated and the aqueous layer was back extracted with ethyl acetate (2×200 mL). The combined organic layers were dried (MgSO₄), filtered and concentrated. The crude material was purified by flash chromatography (Teledyne ISCO Combi-Flash Rf, 0% to 70% solvent A/B=heptane/EtOAc, REDISEP® SiO₂ 120 g). Concentration of the appropriate fractions provided Intermediate 6A (3.13 g, 81%). ¹H NMR (400 MHz, DMSO-d₆) δ 7.62-7.55 (m, 2H), 7.34-7.22 (m, 2H), 7.09-7.01 (m, 2H), 6.87-6.78 (m, 3H), 6.53 (ddd, J=8.0, 7.0, 1.1 Hz, 1H), 3.85 (s, 3H).

Intermediate 6B: Benzyl (5-(4-methoxyphenyl)-2-oxo-2,3-dihydro-1H-benzo[e][1,4]diazepin-3-yl)carbamate

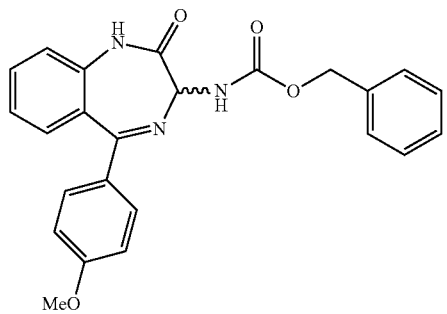

(6B)

In a 100 mL round-bottomed flask was placed Intermediate 6A (3.1 g, 13.64 mmol) and 2-(1H-benzo[d][1,2,3]triazol-1- yl)-2-(benzyloxycarbonylamino)acetic acid (5.34 g, 16.37 mmol) and DCM (50 mL) to give a suspension. The mixture was then cooled to 0° C. and a solution of DCC (3.94 g, 19.10 mmol) in DCM (5 mL) was added. The reaction mixture was warmed to room temperature and stirred for 16 hrs at room temperature. Saturated NaHCO₃ (50 mL) was added and the solid was filtered and discarded. The organic phase was separated, dried with MgSO₄, filtered and concentrated under reduced pressure. The crude reaction mixture was diluted with methanol (100 mL) and ammonia (2N in methanol, 100 mL, 200 mmol) was added and the mixture was stirred at room temperature for 4 hrs. AcOH (50 mL, 873 mmol) was then added and stirring continued at room temperature under nitrogen over night. The crude reaction mixture was concentrate and dried under high vacuum. The crude product was diluted with ethyl acetate (50 mL) and then diluted again slowly with diethyl ether (300 mL). The resulting solid was filtered and air dried. The crude material was purified by flash chromatography (Teledyne ISCO CombiFlash Rf, 0% to 50% solvent A/B=heptane/EtOAc, REDISEP® SiO₂ 120 g). Concentration of the appropriate fractions provided Intermediate 6B (1.32 g, 23%). ¹H NMR (400 MHz, DMSO-d₆) δ 10.80 (s, 1H), 8.35 (d, J=8.6 Hz, 1H), 7.69-7.58 (m, 1H), 7.49-7.21 (m, 10H), 7.00 (d, J=8.8 Hz, 2H), 5.08 (s, 2H), 5.02 (d, J=8.6 Hz, 1H), 3.82 (s, 3H).

Intermediate 6C: 3-Amino-5-(4-methoxyphenyl)-1H-benzo[e][1,4]diazepin-2(3H)-one

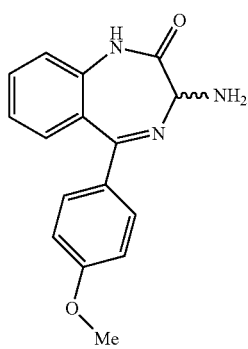

(6C)

Intermediate 6B (1000 mg, 2.407 mmol) was treated with 33% HBr in acetic acid (5 mL) to give a suspension. The reaction mixture was then heated to 70° C. for 3 hrs with stirring. The reaction mixture was then poured into ether (100 mL). The resulting solid was filtered and then partitioned between DCM (100 mL)/saturated NaHCO₃ (100 mL). The aqueous phase was back extracted with DCM (3×100 mL). The combined organic phases were dried with MgSO₄, filtered and concentrated to provided Intermediate 6C (0.608 g, 90%). ¹H NMR (400 MHz, DMSO-d₆) δ 10.61 (br. s., 1H), 7.62-7.53 (m, 1H), 7.44 (d, J=8.8 Hz, 2H), 7.34-7.23 (m, 2H), 7.23-7.17 (m, 1H), 6.99 (d, J=9.0 Hz, 2H), 4.20 (s, 1H), 3.81 (s, 3H).

Intermediate 6D: (2S,3R)-tert-Butyl 6,6,6-trifluoro-3-((5-(4-methoxyphenyl)-2-oxo-2,3-dihydro-1H-benzo[e][1,4]diazepin-3-yl)carbamoyl)-2-(3,3,3-trifluoropropyl) hexanoate

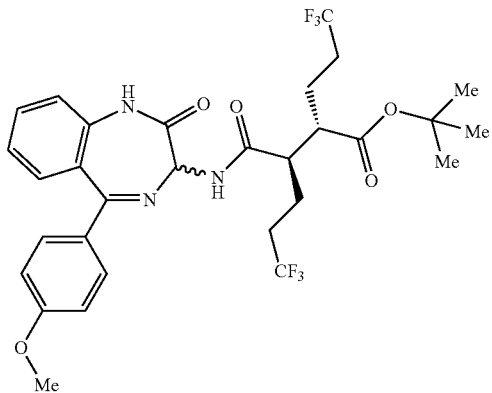

(6D)

A solution of Intermediate 6C (309 mg, 1.100 mmol), Intermediate S-1 (375 mg, 1.024 mmol), and TEA (0.595 mL, 4.27 mmol) in DMF (5 mL) was treated with o-Benzotriazol-1-yl-N,N,N',N'-tetramethyluronium tetrafluoroborate (329 mg, 1.024 mmol) to give a solution. The mixture was stirred at room temperature under nitrogen overnight. The reaction mixture was then diluted with water (50 mL). The resulting solid was collected by filtration and air dried to provide Intermediate 6D (0.500 g, 93%). ¹H NMR (400 MHz, DMSO-d₆) δ 10.81 (d, J=6.6 Hz, 1H), 9.48 (d, J=5.5 Hz, 1H), 7.64 (t, J=6.4 Hz, 1H), 7.46 (dd, J=8.7, 4.1 Hz, 2H), 7.39-7.21 (m, 3H), 7.00 (dd, J=8.8, 3.3 Hz, 2H), 5.22 (dd, J=9.4, 7.6 Hz, 1H), 3.82 (s, 3H), 2.96-2.83 (m, 1H), 2.39-2.11 (m, 4H), 1.91 (s, 1H), 1.86-1.54 (m, 4H), 1.44 (s, 9H), 1.42-1.37 (m, 1H).

Intermediate 6E: (2S,3R)-6,6,6-Trifluoro-3-((5-(4-methoxyphenyl)-2-oxo-2,3-dihydro-1H-benzo[e][1,4]diazepin-3-yl)carbamoyl)-2-(3,3,3-trifluoropropyl) hexanoic acid

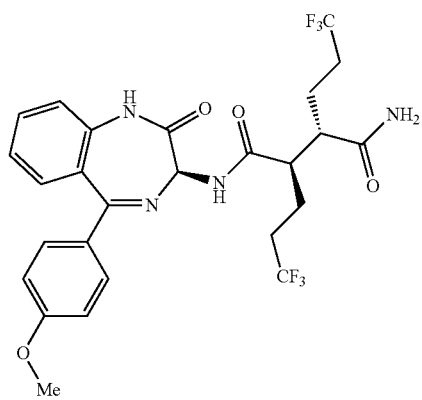

(6E)

A solution of Intermediate 6D (350 mg, 0.556 mmol) in DCM (10 mL) was treated with TFA (2 mL, 26.0 mmol). The reaction mixture was stirred at room temperature 16 hrs. The reaction mixture was then concentrated and dried under high vacuum. The crude reaction mixture was diluted with DMF (6 mL) and treated with EDC (150 mg, 0.785 mmol), HOBT (120 mg, 0.785 mmol), DIPEA (1.096 mL, 6.28 mmol), and ammonium chloride (336 mg, 6.28 mmol). The mixture was stirred at room temperature under nitrogen for 16 hrs. Additional EDC (150 mg, 0.785 mmol), HOBT (120 mg, 0.785 mmol) and DIPEA (1.096 mL, 6.28 mmol) were then added and stirring continued for an additional 16 hrs. The reaction mixture was then diluted with water (75 mL) and the resulting solid was filtered and air dried. The crude diastereomers were separated by Prep Chiral HPLC (CHIRALPAK® AD 5 cm×50 cm 10 µM isocratic 30% i-propanol:heptane 100 ml/min) to afford Intermediate 6E (0.085 g, 56%). $^1$H NMR (400 MHz, DMSO-$d_6$) δ 10.82 (s, 1H), 9.43 (d, J=7.5 Hz, 1H), 7.64 (td, J=7.7, 1.5 Hz, 2H), 7.52-7.41 (m, 2H), 7.38-7.22 (m, 3H), 7.13 (s, 1H), 7.04-6.93 (m, 2H), 5.25 (d, J=7.5 Hz, 1H), 3.82 (s, 3H), 2.80 (td, J=10.0, 4.2 Hz, 1H), 2.47 (br. s., 1H), 2.32-2.08 (m, 4H), 1.84-1.57 (m, 4H).

Example 6

A mixture of Intermediate 6E (48 mg, 0.084 mmol), (bromomethyl)cyclopropane (0.040 mL, 0.419 mmol), and potassium fluoride (40% on aluminum oxide) (170 mg, 1.170 mmol) in DMF (2 mL) was stirred at room temperature for 24 hrs. Additional (bromomethyl)cyclopropane (0.040 mL, 0.419 mmol) was added and stirring continued for 24 hrs. The reaction mixture was diluted with water (50 mL) and the resulting solid was filtered and air dried. The crude material was purified by flash chromatography (Teledyne ISCO CombiFlash Rf, 0% to 60% solvent A/B=DCM/EtOAc, REDISEP® SiO$_2$ 4 g). Concentration of the appropriate fractions provided Example 6 (0.014 g, 26%). HPLC: RT=10.4 min (H$_2$O/CH$_3$CN with TFA, SunFire C18 3.5 µm, 4.6×150 mm, gradient=15 min, wavelength=220 and 254 nm); MS(ES):m/z=627 [M+H$^+$]; $^1$H NMR (400 MHz, DMSO-$d_6$) δ 9.46 (d, J=7.3 Hz, 1H), 7.79-7.63 (m, 3H), 7.56-7.48 (m, 2H), 7.42-7.32 (m, 2H), 7.13 (s, 1H), 7.06-6.98 (m, 2H), 5.27 (d, J=7.3 Hz, 1H), 4.17 (dd, J=14.4, 7.4 Hz, 1H), 3.83 (s, 3H), 3.66 (dd, J=14.3, 7.0 Hz, 1H), 2.85-2.72 (m, 1H), 2.47-2.42 (m, 1H), 2.31-2.06 (m, 3H), 1.76-1.47 (m, 4H), 1.23-1.15 (m, 1H), 0.73 (t, J=7.5 Hz, 1H), 0.29-0.19 (m, 1H), 0.14 (tt, J=8.6, 4.5 Hz, 1H), 0.04 (dq, J=9.2, 4.7 Hz, 1H), −0.02-0.11 (m, 1H).

Example 7

(2R,3S)-N-((3S)-7-Methoxy-2-oxo-5-phenyl-1-(2,2,2-trifluoroethyl)-2,3-dihydro-1H-1,4-benzodiazepin-3-yl)-2,3-bis(3,3,3-trifluoropropyl)succinamide

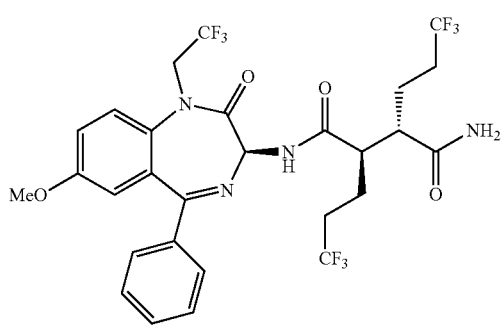

(7)

Intermediate 7A:
(2-Amino-5-methoxyphenyl)(phenyl)methanone

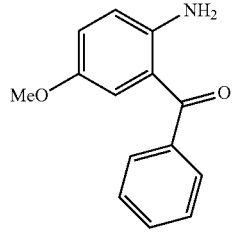

(7A)

To a stirred solution of BCl$_3$ (4.5 mL, 1M in DCM, 4.47 mmol) at 0° C., was added a mixture of 4-methoxyaniline (0.5 g, 4.06 mmol) and benzonitrile (0.837 g, 8.12 mmol) in toluene (5 mL) slowly over a period of twenty five minutes under a nitrogen atmosphere. The mixture was stirred for five minutes at 0° C. and then AlCl$_3$ (0.595 g, 4.47 mmol) was added portion wise over a period of 2 minutes at 0° C. The reaction mixture was allowed to warm to room temperature and then heated at 115° C. for eight hours. The reaction mixture was cooled to room temperature, and was sequentially quenched with ice cold water (1 mL) and 1.5N aqueous HCl (5 mL) over thirty minutes. The reaction mixture was further refluxed at 100° C. for two hours, cooled to 0° C. and 10% aqueous NaHCO$_3$ (20 mL) was added dropwise over fifteen minutes until the pH was ~8.5. The aqueous layer was extracted with EtOAc (3×25 mL). The organic layers were combined and washed with brine (2×10 mL), dried (Na$_2$SO$_4$), filtered and concentrated in vacuo. The crude residue was purified by ISCO chromatography on silica gel using EtOAc/hexane (1:12) as eluent to afford Intermediate 7A. (0.25 g, 27%). HPLC: RT=1.37 min (MeOH/H$_2$O with TFA, CHROMOLITH® speed ROD C18 5 µm, 4.6×30 mm, gradient=3 min, Flow=5 mL/min; Mobile Phase A: 10% MeOH-90% H$_2$O-0.1% TFA; Mobile Phase B: 90% MeOH-10% H$_2$O-0.1% TFA; wavelength=220); MS(ES): m/z=228 [M+H]$^+$.

Intermediate 7B: Benzyl (7-methoxy-2-oxo-5-phenyl-2,3-dihydro-1H-benzo[e][1,4]diazepin-3-yl)carbamate

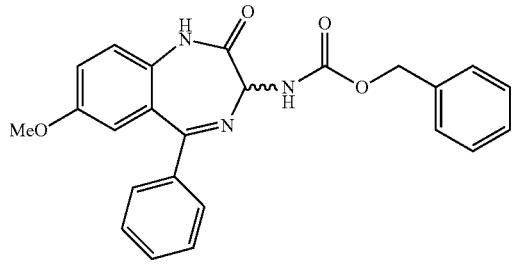

(7B)

A solution of 2-(1H-benzo[d][1,2,3]triazol-1-yl)-2-(benzyloxycarbonylamino)acetic acid (0.446 g, 1.965 mmol) in 5 mL of dry THF was cooled to 0° C. and then treated with oxalyl chloride (0.171 mL, 1.34 mmol). The mixture was stirred for 30 min at 0° C. A mixture of Intermediate 7A (0.235 g, 1.034 mmol) and NMM (0.237 mL, 2.59 mmol) in DCM (3 mL) was added to the above mixture. The resulting mixture was stirred at room temperature for 2 h and then filtered. The filtrate was treated with 2M methanolic ammonia (10 mL) and stirred at room temperature for 12 hrs. The mixture was then evaporated to dryness and the residue was treated with AcOH (5 mL) and stirred for 2 hrs at room temperature. The reaction mixture was then concentrated and purified by flash column chromatography to provide Intermediate 7B as a white solid: 70 mg (16.29%). HPLC: RT=1.908 min (ACN/H$_2$O with TFA, UPLC R BEH C18, 1.7 µm, 2.1×50 mm, gradient=4 min, Flow=1.8 mL/min; Mobile Phase A: 0.1% TFA in water; Mobile Phase B: Acetonitrile; wavelength=220 nm); MS(ES): m/z=416 [M+H]$^+$; $^1$H NMR (CDCl$_3$) δ 8.681 (brs, 1H), 7.565-7.583 (d, J=7.2 Hz, 1H), 7.30-7.50 (m, 7H), 7.097 (brs, 2H), 6.80 (brs, 1H), 6.22 (d, J=8.4 Hz, 1H), 5.34 (d, J=7.2 Hz, 1H), 5.17 (s, 2H), 3.72 (s, 3H).

Intermediate 7C: 3-Amino-7-methoxy-5-phenyl-1H-benzo[e][1,4]diazepin-2(3H)-one

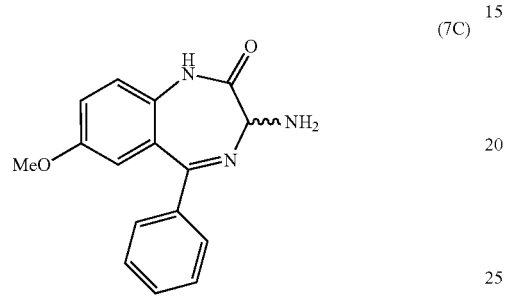

(7C)

Intermediate 7B (0.5 g, 1.2 mmol) was treated with 3.5 mL (7 volumes) of 33% HBr in AcOH and was stirred at room temperature for 2 hrs. Diethyl ether (25 mL) was added to the reaction mixture and the precipitated solid was collected by filtration. The solid was dissolved in water (3 mL), and 10% sodium bicarbonate solution was added until the solution was basic. The product was extracted with 2×25 mL of ethyl acetate and the organic layer was dried over anhydrous sodium sulfate. The solvents were removed under vacuum to afford Intermediate 7C as a white solid: yield 0.32 g (98%). HPLC: RT=1.228 (H$_2$O/ACN with NH$_4$OAc, PUROSPHER® Star RP-18 (4×55) mm, 3 µm, gradient=3 min, wavelength=220 nm); MS(ES):m/z=282 [M+H$^+$]; $^1$H NMR (DMSO-d$_6$: δ 10.46 (brs, 1H), 7.42-7.53 (m, 5H), 7.19-7.25 (m, 2H), 6.72 (d, J=2.4 Hz, 1H), 4.25 (s, 1H), 3.39 (s, 3H).

Intermediate 7D: (2S,3R)-tert-Butyl 6,6,6-trifluoro-3-((7-methoxy-2-oxo-5-phenyl-2,3-dihydro-1H-benzo[e][1,4]diazepin-3-yl)carbamoyl)-2-(3,3,3-trifluoropropyl)hexanoate

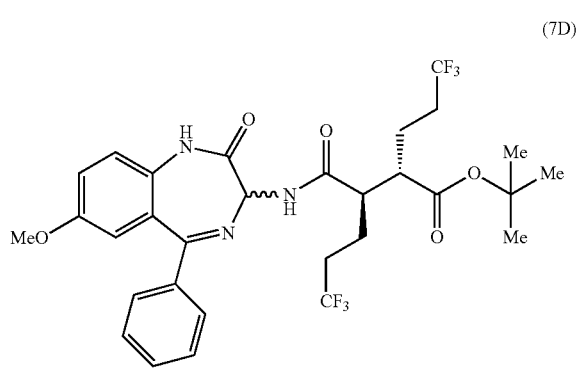 [SMILES: COc1ccc2c(c1)C(c1ccccc1)=NC(NC(=O)[C@H](CCC(F)(F)F)[C@H](CCC(F)(F)F)C(=O)OC(C)(C)C)C(=O)N2]

(7D)

A solution of Intermediate 7C (330 mg, 1.173 mol), and Intermediate S-1 (366 mg, 1.173 mmol) in DMF (5 mL) was cooled to 0° C. under a nitrogen atmosphere, and then treated with TBTU (490 mg, 1.525 mmol) followed by the dropwise addition of triethylamine (0.40 mL, 2.34 mmol) over three minutes. The reaction mixture was stirred for another sixteen hours at room temperature and then cooled to 0° C. Water (10 mL) was added and the resulting solid was collected by filtration, washed with water (5 mL) and dried to afford Intermediate 7D: yield 650 mg (89%); HPLC: RT=2.282 (H$_2$O/ACN with NH$_4$OAc, PUROSPHER® Star RP-18 (4×55) mm, 3 µm, gradient=3 min, wavelength=220 nm); MS(ES): m/z=630 [M+H$^+$]; $^1$H NMR (DMSO-d$_6$: as mixture of diastereomers) δ 10.66 (s, 1H), 9.50-9.52 (dd, J=9.6, 2.0 Hz, 1H), 7.5-7.6 (m, 3H), 7.5 (m, 2H), 7.2-7.3 (m, 2H), 6.76-6.70 (d, J=2.4, 1H), 5.25-5.29 (t, 8.8 Hz, 1H), 3.7 (s, 3H), 2.90-2.91 (m, 1H), 2.50 (m, 1H), 2.10-2.34 (m, 4H), 1.48-1.90 (m, 4H), 1.43 (s, 9H).

Intermediate 7E: (2S,3R)-6,6,6-Trifluoro-3-((7-methoxy-2-oxo-5-phenyl-2,3-dihydro-1H-benzo[e][1,4]diazepin-3-yl)carbamoyl)-2-(3,3,3-trifluoropropyl)hexanoic acid

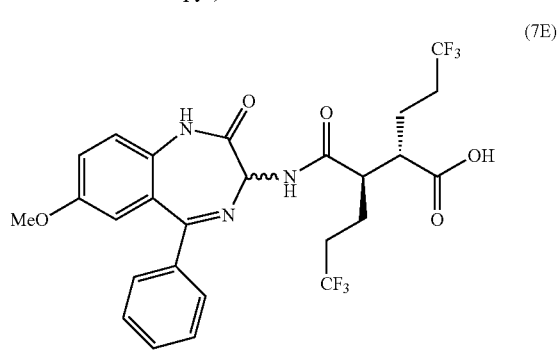

(7E)

To a stirred solution of Intermediate 7D (1.03 mg, 0.836 mmol) in CH$_2$Cl$_2$ (8 mL) at 0° C. under a nitrogen atmosphere, was added trifluoroacetic acid (3 mL) dropwise over two minutes. The reaction mixture was stirred at 0° C. for one hour and then stirred at room temperature for five hours. The reaction mixture was then concentrated and treated with ice cold water (50 grams). After stirring for fifteen minutes, the off-white precipitate was filtered, washed with water (5 mL) and dried to provide Intermediate 7E as a white solid: yield=500 mg (84%); HPLC: RT=2.282 (H$_2$O/AcCN with NH$_4$OAc, PUROSPHER® Star RP-18 (4×55) mm, 3 µm, gradient=3 min, wavelength=220 nm); MS(ES):m/z=572 [M−H$^+$]; $^1$H NMR (DMSO-d$_6$: as mixture of diastereomers) δ 10.67 (s, 1H), 9.51-9.54 (t, J=7.2 Hz, 1H), 7.5-7.6 (m, 3H), 7.5 (m, 2H), 7.1-7.3 (m, 4H), 6.771 (s, 1H), 5.29 (t, J=8.0 Hz, 1H), 3.7 (s, 3H), 2.80-2.91 (m, 1H), 2.70 (m, 1H), 2.50 (m, 1H), 2.10-2.34 (m, 3H), 1.50-1.90 (m, 3H).

Intermediate 7F: (2R,3S)-N1-((S)-7-Methoxy-2-oxo-5-phenyl-2,3-dihydro-1H-benzo[e][1,4]diazepin-3-yl)-2,3-bis(3,3,3-trifluoropropyl)succinamide

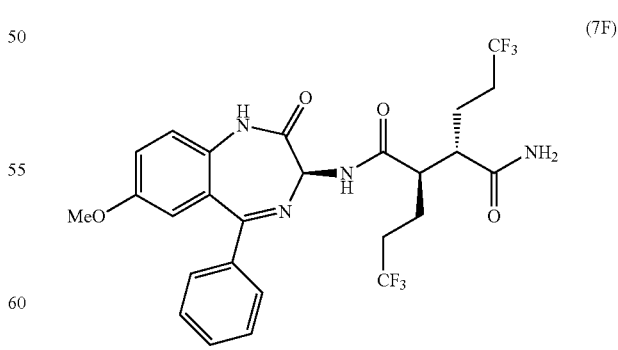

(7F)

To a stirred solution of Intermediate 7E (500 mg, 1.047 mmol), pyBOP (0.65 mg, 1.25 mmol), and ammonium chloride (0.28 mg, 5.23 mmol) in DMSO (6 mL), at 0° C. under a nitrogen atmosphere, was added dropwise a solution of N,N'-diisopropylethylamine (0.36 mL, 2.09 mmol) over two minutes. The ice bath was removed and the reaction mixture was stirred at room temperature for sixteen hours. The mixture was then poured into ice cooled water (20 grams) and stirred for one hour and then filtered. The crude residue was subjected to preparative HPLC purification/separation (Column-CHIRALCEL® ODH (250×4.6) mm 5 micron, Mobile Phase A: 0.2% diethylamine-hexane (80%), Mobile Phase B: ethanol (20%), @ 220 and 250 nm Flow-1 ml/Min, Run-20 min) to provide Intermediate 7F as a white solid: yield 180 mg (10%). $^1$H NMR (400 MHz, DMSO-$d_6$) δ ppm 10.67 (s, 1H), 9.444-9.463 (d, J=7.6 Hz, 1H), 7.60-7.7 (brs, 1H), 7.51-7.54 (m, 3H), 7.44-7.47 (m, 2H), 7.24-7.28 (m, 2H), 7.14-7.19 (brs, 1H), 6.77-6.78 (d, J=4 Hz, 1H), 5.3-5.31 (d, J=4 Hz, 1H), 3.71 (s, 3H), 2.78-2.84 (m, 1H), 2.2.11-2.31 (m, 4H), 1.60-1.74 (m, 4H), MS (M−1)=571. HPLC RT=9.31 min (Xbridge Phenyl (4.6×150 mm), 3.5 micron; 1 mL/min flow rate; gradient 10% B-100% B over 12 min (A: 0.05% TFA in water/$CH_3CN$ (95:5), B: 0.05% TFA in water/$CH_3CN$ (5:95) @ 220 and 250 nm, 15 min run).

Example 7

To a stirred solution of Intermediate 7F (30 mg, 0.052 mol) and cesium carbonate (34 mg, 0.1 mmol) in DMF (2.5 mL) at 0° C. under a nitrogen atmosphere, was added 2,2,2-trifluoroethyltrifluoromethanesulfonate (24.3 mg, 0.10 mm) dropwise over one minute. The reaction mixture was stirred for another sixteen hours at room temperature and then cooled to 0° C. The reaction mixture was then quenched with water (10 mL). The resulting precipitate was filtered, washed with water (5 mL) and dried to afford Example 7. The crude material was purified by Prep-HPLC (Column-SYMMETRY® Shield RP18 (250×4.6) mm 5 micron, Mobile Phase A:0.05% TFA in water, Mobile Phase B: ACN @ 220 and 250 nm Flow rate-1 ml/Min, gradient 40% B-100% B over 25 min) to afford Example 7: yield 17 mg (50%). $^1$H NMR (400 MHz, CDCl$_3$) δ ppm 7.55-7.60 (m, 3H), 7.48-7.52 (m, 4H), 7.329-7.351 (d, J=8.8 Hz, 1H), 7.149-7.179 (dd, J=4 Hz and 12 Hz 1H), 6.805-6.812 (d, J=2.8 Hz, 1H), 5.92 (brs, 1H), 5.63 (brs, 1H) 5.605-5.625 (d, J=8 Hz, 1H), 5.14-5.22 (m, 1H), 4.05-4.13 (m, 1H), 3.76 (s, 3H), 2.56-2.65 (m, 2H), 2.09-2.30 (m, 5H), 1.80-2.0 (m, 3H), MS (M+H$^+$)=655. HPLC RT=11.17 min (SunFire C18 (4.6×150 mm), 3.5 micron; 1 mL/min flow rate; gradient 10% B-100% B over 12 min (A: 0.05% TFA in water/$CH_3CN$ (95:5), B: 0.05% TFA in water/$CH_3CN$ (5:95) @ 220 and 250 nm, 15 min run).

Example 8

(2R,3S)-N-((3S)-1-(Cyclopropylmethyl)-2-oxo-5-phenyl-2,3-dihydro-1H-1,4-benzodiazepin-3-yl)-3-(2,2-difluoropropyl)-2-(3,3,3-trifluoropropyl)succinamide (8)

Intermediate 8A: (3S)-3-Amino-5-phenyl-1,3-dihydro-2H-1,4-benzodiazepin-2-one

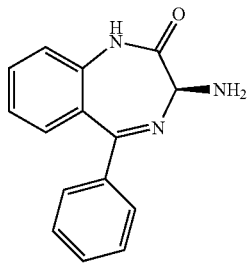

(8A)

Racemic 3-amino-5-phenyl-1,3-dihydro-2H-1,4-benzodiazepin-2-one (J. Med. Chem., 49:2311-2319 (2006), compound #5) was prepared according to the literature procedure. The enantiomers were separated (Berger SFC MGIII Column: Lux 25×3 cm, 5 cm; Mobile Phase: 30% MeOH+0.1% DEA in CO$_2$; Flow rate: 150 mL/min; Temperature: 40° C.; Detector wavelength: 250 nM). Obtained the S-enantiomer Intermediate 8A as a white solid: $^1$H NMR (400 MHz, DMSO-d$_6$) δ ppm 10.67 (1 H, br. s.), 7.58 (1 H, td, J=7.65, 1.76 Hz), 7.37-7.53 (5 H, m), 7.23-7.30 (2 H, m), 7.14-7.22 (1 H, m), 4.23 (1 H, s), 2.60 (2 H, br. s.); HPLC: RT=3.0625 min (30% MeOH+0.1% DEA in CO$_2$ on OD-H Column, 3 mL/min, 35° C., 96 bar, 230 nm, 10 μl inj); [α]$_D$=−208.3° (5.05 mg/mL, MeOH).

Intermediate 8B: (2R)-3-(2,2-Difluoropropyl)-N1-((S)-2-oxo-5-phenyl-2,3-dihydro-1H-benzo[e][1,4]diazepin-3-yl)-2-(3,3,3-trifluoropropyl)succinamide

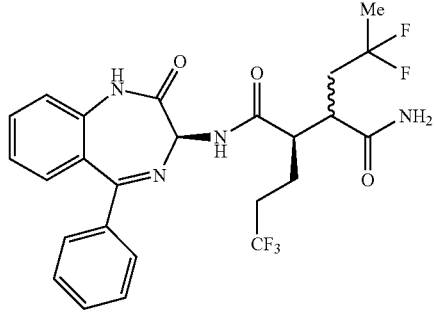

(8B)

Intermediate 8B was prepared from Intermediate 8A and Intermediate S-4 according to the general procedure shown for Example 1 as a 1:1 mixture of diastereomers. MS(ES):

m/z 525.1 (M+H⁺). HPLC RT=0.85 min. (BEH C18 2.1×50 mm, 1.7 μ, 0 to 100 B in 1 min with 0.5 min hold time, Flow rate=1 ml/min, detection at 254 nm, Solvent A: 100% water/ 0.1% TFA; Solvent B: 100% ACN/0.1% TFA). ¹H NMR (400 MHz, MeOD) δ ppm 7.58-7.66 (1 H, m), 7.54 (3 H, d, J=1.54 Hz), 7.41 (4 H, s), 7.19-7.29 (1 H, m), 5.39 (1 H, s), 2.78-2.92 (1 H, m), 2.64-2.78 (1 H, m), 2.34-2.59 (2 H, m), 2.13-2.31 (1 H, m), 1.95-2.14 (1 H, m), 1.73-1.92 (2 H, m), 1.47-1.69 (3 H, m).

Example 8

To a stirred mixture of Intermediate 8B (22 mg, 0.042 mmol) and (bromomethyl)cyclopropane (28.3 mg, 0.210 mmol) in DMF (1 mL) was added potassium fluoride (40% on aluminum oxide) (85 mg, 0.585 mmol). The reaction mixture was stirred at room temperature for 16 h. The solid material was removed by filtration and the filtrate was concentrated in vacuo. The crude product was purified by chiral SFC (Berger SFC MGIII, Column: CHIRALPAK® IC 25×15 mm ID, 0.5 μm; Mobile Phase: 80/20 CO₂/EtOH with 0.1% DEA, Flow rate: 50 mL/min; Detection at 220 nm) to give Example 8 (12 mg, 0.020 mmol, 48.5% yield) as a white solid. MS(ES): m/z 579.2 (M+H+). HPLC RT=0.97 min. (BEH C18 2.1×50 mm, 1.7μ, 0 to 100 B in 1 min with 0.5 min hold time, Flow rate=1 mL/min, detection at 254 nm, Solvent A: 100% water/0.1% TFA; Solvent B: 100% ACN/0.1% TFA). ¹H NMR (400 MHz, chloroform-d) δ ppm 7.53-7.65 (4 H, m), 7.49 (2 H, s), 7.41 (3 H, d, J=7.70 Hz), 5.92-6.10 (1 H, m), 5.51 (2 H, d, J=7.70 Hz), 4.21-4.38 (1 H, m), 3.49-3.65 (1 H, m), 2.79-2.98 (1 H, m), 2.45-2.72 (2 H, m), 2.07-2.33 (3 H, m), 1.89-2.03 (1 H, m), 1.76-1.89 (1 H, m), 1.67 (3 H, t, J=18.60 Hz), 0.82-1.00 (2 H, m), 0.34-0.43 (1 H, m), 0.17-0.33 (1 H, m), 0.11 (2 H, br. s.).

Example 9

(2R,3S)-N-((3S)-1-(Cyclopropylmethyl)-2-oxo-5-phenyl-2,3-dihydro-1H-1,4-benzodiazepin-3-yl)-2-(2,2-difluoropropyl)-3-(3,3,3-trifluoropropyl)succinamide

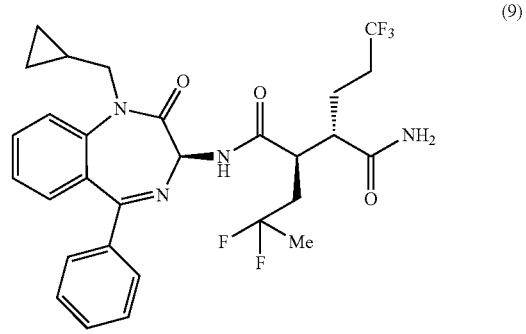 [SMILES: CC(F)(F)C[C@@H](C(=O)N[C@H]1N=C(c2ccccc2)c2ccccc2N(CC2CC2)C1=O)[C@H](CCC(F)(F)F)C(N)=O]

(9)

Intermediate 9A: (3S)-2-(2,2-Difluoropropyl)-N1-((S)-2-oxo-5-phenyl-2,3-dihydro-1H-benzo[e][1,4]diazepin-3-yl)-3-(3,3,3-trifluoropropyl)succinamide

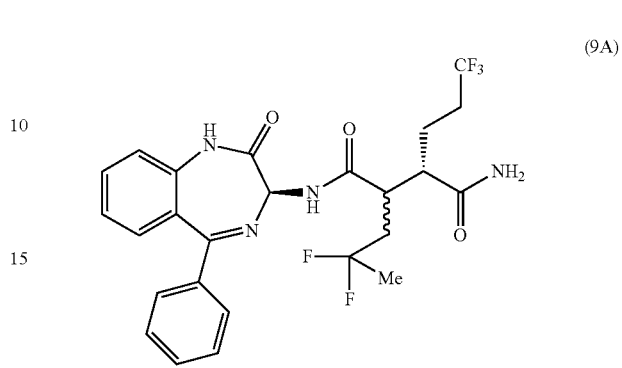

(9A)

Intermediate 9A was prepared from Intermediate 8A and Intermediate S-5 as a 1:1 mixture of diastereomers according to the general procedure shown for Example 1. HPLC RT=0.84 min. (BEH C18 2.1×50 mm, 1.7μ, 0 to 100 B in 1 min with 0.5 min hold time, Flow rate=1 ml/min, detection at 254 nm, Solvent A: 100% water/0.1% TFA; Solvent B: 100% ACN/0.1% TFA). ¹H NMR (400 MHz, MeOD) δ ppm 7.55-7.68 (1 H, m), 7.43-7.57 (3 H, m), 7.33-7.44 (3 H, m), 7.19-7.34 (2 H, m), 5.32-5.49 (1 H, m), 2.96-3.13 (1 H, m), 2.48-2.62 (1 H, m), 2.30-2.48 (1 H, m), 2.11-2.29 (2 H, m), 1.84-2.06 (3 H, m), 1.50-1.71 (3 H, m). MS(ES):m/z=525.2 [M+H⁺].

Example 9

Example 9 was prepared from Intermediate 9A in the same manner as described for Example 8. The diastereomers were separated by preparative SFC (Berger SFC MGIII, Column: CHIRALPAK® IC 25×15 mm ID, 0.5 μm; Mobile Phase: 80/20 CO₂/EtOH with 0.1% DEA, Flow rate: 50 mL/min; Detection at 220 nm) to afford the title compound. MS(ES): m/z 579.2 (M+H+). HPLC RT=0.97 min. (BEH C18 2.1×50 mm, 1.7μ, 0 to 100 B in 1 min with 0.5 min hold time, Flow rate=1 mL/min, detection at 254 nm, Solvent A: 100% water/ 0.1% TFA; Solvent B: 100% ACN/0.1% TFA). ¹H NMR (400 MHz, chloroform-d) δ ppm 7.77-7.86 (1 H, m), 7.50-7.66 (3 H, m), 7.32-7.51 (5 H, m), 6.36-6.50 (1 H, m), 5.48 (2 H, d, J=7.26 Hz), 4.18-4.39 (1 H, m), 3.50-3.66 (1 H, m), 2.82-2.99 (1 H, m), 2.65-2.83 (1 H, m), 2.35-2.59 (1 H, m), 2.20-2.36 (1 H, m), 2.01-2.24 (3 H, m), 1.84-2.02 (1 H, m), 1.59-1.71 (3 H, m), 0.74-0.98 (2 H, m), 0.33-0.44 (1 H, m), 0.21-0.33 (1 H, m), 0.10 (2 H, d, J=4.62 Hz).

Comparative Compounds 10 to 13

Comparative Compounds 10 to 13 can be prepared according to the procedures described in U.S. Pat. No. 7,053,084 for Examples 8, 12a, 38, and 45a, respectively.

TABLE 1
| Comparative Compound | U.S. Pat. No. 7,053,084 | Structure |
|---|---|---|
| 10 | Ex. 8 | 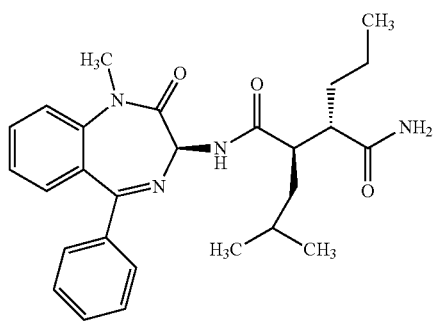 [SMILES: CCC[C@H](C(N)=O)[C@@H](CC(C)C)C(=O)N[C@H]1N=C(c2ccccc2)c2ccccc2N(C)C1=O] |
| 11 | Ex. 12a | 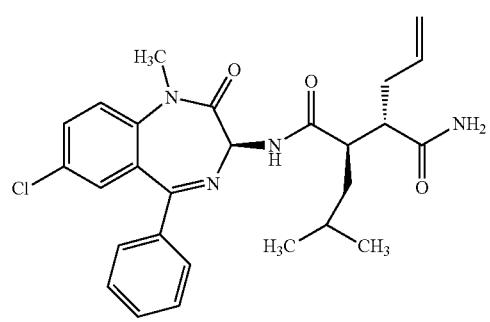 [SMILES: C=CC[C@H](C(N)=O)[C@@H](CC(C)C)C(=O)N[C@H]1N=C(c2ccccc2)c2cc(Cl)ccc2N(C)C1=O] |
| 12 | Ex. 38 | 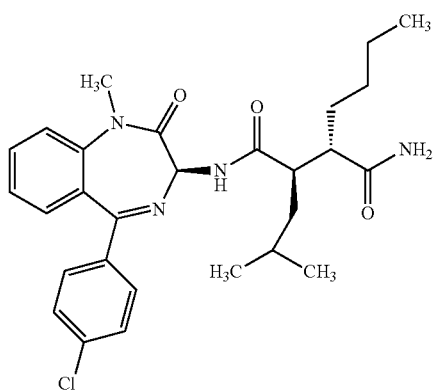 [SMILES: CCCC[C@H](C(N)=O)[C@@H](CC(C)C)C(=O)N[C@H]1N=C(c2ccc(Cl)cc2)c2ccccc2N(C)C1=O] |
| 13 | Ex. 45a | 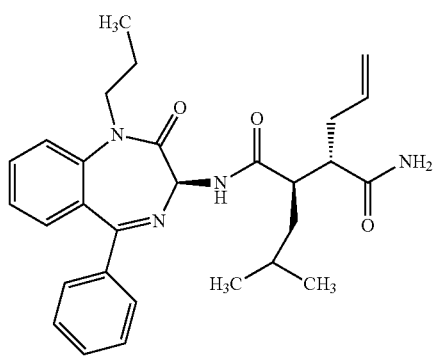 [SMILES: C=CC[C@H](C(N)=O)[C@@H](CC(C)C)C(=O)N[C@H]1N=C(c2ccccc2)c2ccccc2N(CCC)C1=O] |

BIOLOGICAL ASSAYS

The pharmacological properties of the compounds of this invention may be confirmed by a number of biological assays. The exemplified biological assays, which follow, have been carried out with compounds of the invention.

Notch-CBF1 Transactivation Assay

The Notch-CBF1 (C-promoter binding factor I) cell based transactivation assay is based on the ability of the released Notch intracellular domain fragments (NICDs) to function as transcription factors in conjunction with CBF1 and other nuclear factors. Luciferase assays were used to measure the antagonism of Notch-CBF1 transcriptional activity. HeLa cervical cancer cells are transiently co-transfected with pCDNA3.1/Hygro plasmids containing truncated Notch 1, Notch 2, Notch 3, or Notch 4 receptors and a PGL3 luciferase reporter vector containing 4 copies of CBF1 binding site. The cells were then tested for Notch-CBF1 activity in the absence or presence of test compounds. HeLa cells, maintained in DMEM (high glucose with HEPES), 1× glutamine/penicillin/streptomycin and 10% Fetal Bovine serum, were transiently transfected in a T175 Flask ($4.5 \times 10^6$ cells/flask) using the Monster Transfection Kit (Mirus #MIR2906) according to manufacturers specifications. Table 2 denotes respective DNA quantity for the transfections.

TABLE 2

|  | DNA (µg) | CBF1 (µg) | Vector (µg) | Total DNA (µg) |
|---|---|---|---|---|
| human Notch 1 | 6 | 14.4 | 15.6 | 36.0 |
| human Notch 2 | 2 | 14.4 | 19.6 | 36.0 |
| human Notch 3 | 0.3 | 14.4 | 21.3 | 36.0 |
| human Notch 4 | 4 | 14.4 | 17.6 | 36.0 |

Six hours post-transfection, cells were trypsinized and plated into a 384-well black Poly-D-lysine coated tissue culture plate at a density of $5 \times 10^3$ cells/well in 95 µL assay media (DMEM (high glucose with HEPES), 1× glutamine/penicillin/streptomycin, 0.0125% BSA, 1× non-essential amino acids). Assay media (5 µL) containing test compounds in final concentrations ranging from 5 µM to $8.4 \times 10^{-5}$ µM (3 fold serial dilutions) were added to the cells and the cell plates were then incubated for 18 hours at 37° C. and 5% $CO_2$. Control wells contained DMSO vehicle (total counts) or 0.5 µM of an in-house small molecule inhibitor (background counts). Duplicates were used for each sample. Luciferase activity was measured after a 20-minute incubation with 50 µl STEADY-GLO® luciferase reagents according to manufacturer's specifications (Promega, Cat. #E2550) and analyzed by Envision plate reader (PerkinElmer, Boston, Mass.).

The antagonist effect of compounds was expressed as 100× [1−(average sample−average background)/(average total−average background)] where sample is the luciferase activity in the presence of test compound, background is equal to the luciferase activity in the presence of the small molecule inhibitor control and the total is signal induced in DMSO wells. Data was plotted using a four parameter logistic fit equation and the $IC_{50}$ value was defined as the concentration of compound that inhibited 50% of the luciferase activity.

Table 3 below lists the Notch 1 and Notch 3 $IC_{50}$ values for Examples 1-9 of this invention and Comparative Compounds 10-13 measured in the Notch-CBF1 Transactivation Assay hereinabove. In some instances, the value is an average of multiple experiments where N is the number of experiments conducted. The compounds of the present invention, as exemplified by the Examples 1-9 showed Notch 1 values of 26.8 nM or less and Notch 3 $IC_{50}$ values of 22.6 nM or less.

TABLE 3

| Example | Notch ($IC_{50}$, nM) | N | Notch ($IC_{50}$, nM) | N |
|---|---|---|---|---|
| 1 | 15.7 | 2 | 7.8 | 1 |
| 2 | 13.6 | 2 | 16.8 | 2 |
| 3 | 9.6 | 1 | 22.6 | 1 |
| 4 | 6.4 | 1 | 13.3 | 1 |
| 5 | 6.1 | 2 | 14.7 | 2 |
| 6 | 5.8 | 5 | 7.2 | 5 |
| 7 | 7.5 | 2 | 5.1 | 1 |
| 8 | 1.1 | 1 | 2.6 | 1 |
| 9 | 26.8 | 2 | 6.5 | 1 |
| Comparative Compound 10 | 64.1 | 1 | 48.3 | 1 |
| Comparative Compound 11 | 42.4 | 2 | 74.5 | 2 |
| Comparative Compound 12 | 5.1 | 3 | 13.5 | 4 |
| Comparative Compound 13 | 12.3 | 1 | 12.5 | 1 |

High Throughput (HT) Metabolic Stability Panel

Compounds administered parenterally enter the blood stream and undergo one or more passes through the liver. Compounds that are not readily metabolized by the liver can be administered at therapeutically effective plasma levels for therapeutically effective periods of time.

Orally administered compounds typically are absorbed through the intestinal walls into the blood stream and undergo a first pass through the liver. Compounds that are not readily metabolized in this first pass through the liver can be distributed to other areas of the body in therapeutically effective amounts.

The metabolic stability assay evaluated CYP-mediated metabolic stability in vitro using human, rat, mouse, dog, and/or monkey microsomes after a ten-minute incubation. Each compound was tested in duplicate.

The results of these assays were expressed as the fraction of parent compound remaining in the reaction mixture after a ten-minute incubation (Percent Remaining). In general, these results were used to evaluate only the extent of CYP-mediated, or NADPH-dependent, metabolism of the test compound. When the compound was significantly metabolized (<40-50% remaining), this indicated high clearance of the compound in vivo due to CYP-mediated metabolism. However, if the compound demonstrated moderate (50-80%) or low (>85%) metabolism in these in vitro assays, high clearance was still possible in vivo via other metabolism and elimination pathways.

The percent remaining results of these assays was predictive of compound clearance in vivo, assuming that CYP-mediated metabolism was a predominant elimination pathway. In different microsomal species, the ranges of results were approximately as shown in Table 4.

TABLE 4

| Metabolic Stability - Result Interpretation Guidelines | | | | | |
|---|---|---|---|---|---|
| CYP-Mediated | Percent Remaining after 10 minutes | | | | |
| Clearance | Human | Rat | Mouse | Dog | Monkey |
| Low | >90 | >85 | >85 | >90 | >85 |
| Medium | 60-90 | 40-85 | 50-85 | 55-90 | 40-85 |
| High | <60 | <40 | <50 | <55 | <40 |

Methods and Materials
Incubation with Liver Microsomes

Test compound was received as a 3.5 mM stock solution in 100 percent DMSO. The test compound was diluted to create a 50 µM acetonitrile (ACN) solution containing 1.4% DMSO, which was then used as a 100× stock for incubation with microsomes. Each compound was tested in duplicate separately in each of three species in the Metabolic Stability-Human, Rat, and Mouse assay suite or as individual species in the Metabolic Stability-Dog or Metabolic Stability-Monkey suites. Compound, NADPH, and liver microsome solutions were combined for incubation in three steps:

1. 152 µl of liver microsome suspension, protein concentration of 1.1 mg/ml in 100 mM NaP$_i$, pH 7.4, 5 mM MgCl$_2$ buffer, was pre-warmed at 37° C.

2. 1.7 µl of 50 µM compound (98.6% ACN, 1.4% DMSO) was added to the same tube and pre-incubated at 37° C. for 5 minutes.

3. The reaction was initiated by the addition of 17 µl of pre-warmed 10 mM NADPH solution in 100 mM NaP$_i$, pH 7.4.

The reaction components were mixed well, and 75 µl of the reaction mixture was immediately transferred into 150 µl quench/stop solution (zero-time point, T$_0$). Reactions were incubated at 37° C. for 10 minutes and then an additional 75 µl aliquot was transferred into 150 µl quench solution. Acetonitrile containing 100 µM DMN (a UV standard for injection quality control), was used as the quench solution to terminate metabolic reactions.

Quenched mixtures were centrifuged at 1500 rpm (~500× g) in an ALLEGRA® X-12 centrifuge, SX4750 rotor (Beckman Coulter Inc., Fullerton, Calif.) for fifteen minutes to pellet denatured microsomes. A volume of 90 µl of supernatant extract, containing the mixture of parent compound and its metabolites, was then transferred to a separate 96-well plate for UV-LC/MS-MS analysis to determine the percent of parent compound that remained in the mixture.

TABLE 5

Metabolic Stability Assay - Reaction Components

| Reaction Components | Final Concentration in the Metabolic Stability Assay |
| --- | --- |
| Compound (Substrate) | 0.5 µM |
| NaPi Buffer, pH 7.4 | 100 mM |
| DMSO | 0.014% |
| Acetonitrile | 0.986% |
| Microsomes (human, rat, mouse) (BD/Gentest) | 1 mg/ml protein |
| NADPH | 1.0 mM |
| MgCl$_2$ | 5.0 mM |
| 37° C. Incubation time | 0 minutes and 10 minutes |
| Quench/Stop Solution (ACN + 100 µM DMN) | 150 µl |
| Sample of Reaction | 75 µl |
| Sedimentation of Denatured Microsomes | 15 minutes |
| UV-LC/MS analysis of supernatant | 0.17 µM |

Sample Analysis—Instrumentation

HPLC: Pump—Thermo Surveyor; Autosampler—CTC/LEAP HTS; UV detector—Thermo Surveyor PDA plus; Column—VARIAN® C18, 3 µm, 2×20 mm with a 0.5 µm in-line filter; Mobile Phase for structural integrity pre-analysis: (A) 98% water, 2% acetonitrile with 10 mM ammonium acetate; (B) 10% water, 90% acetonitrile with 10 mM ammonium acetate; Mobile Phase for reaction sample analysis: (A) 98% water, 2% acetonitrile with 0.1% formic acid; (B) 2% water, 98% acetonitrile with 0.1% formic acid; (C) 0.1% ammonium hydroxide in water; (D) 0.1% ammonium hydroxide in acetonitrile.

Mass Spectrometer: Thermo TSQ QUANTUM® Ultra triple-quadrupole mass spectrometer.

Sample Analysis—Structural Integrity Pre-Analysis

The Metabolic Stability structural integrity pre-analysis was used to assess the purity of compounds being assayed. Compounds were received in 96-well plates as 57 µl of a 3.5 mM DMSO solution. The 3.5 mM compound DMSO stock solutions were diluted 18-fold with a solution containing equal volumes of acetonitrile, isopropanol, and MilliQ-H$_2$O. The resulting solutions (200 µM) were analyzed for structural integrity by LC-UV/MS on a Thermo LCQ Deca XP Plus ion trap mass spectrometer, using a Waters XBridge C18, 5 µm, 2×50 mm column with a Waters Sentry 2.1 mm guard column, and the LC conditions described in the table below, with a 5 µl injection and a flow rate of 1 ml/min. The acquired data reflected purity by UV absorbance at 220 nm. Only results for those compounds with purity greater than 50% were reported.

TABLE 6

Metabolic Stability - Structural Integrity Gradient

| Gradient Time (min) | A % | B % |
| --- | --- | --- |
| 0.00 | 100 | 0 |
| 4.00 | 0 | 100 |
| 5.00 | 0 | 100 |
| 5.10 | 100 | 0 |
| 6.00 | 100 | 0 |

Sample Analysis—Incubated Samples

MS/MS condition optimization was conducted on a Thermo TSQ QUANTUM® triple-quadrupole mass spectrometer equipped with a heated-electrospray (H-ESI) source by automated infusion to obtain the SRM transitions and their corresponding collision energy values. Compound solutions at a concentration of 20 µM in 1:1 methanol:water were infused at a flow rate of 90 µL/min, then combined with the mobile phase at a flow rate of 50 µL/min before being introduced into the source. All compounds were optimized first using mobile phase A and B (50% A and 50% B), and if necessary, using mobile phase C and D (also with a 50:50 composition). The optimized parameters, including polarity, SRM transition and collision energy, were stored in a MICROSOFT ACCESS® database.

The mass spectrometric conditions obtained from automated infusion were used to analyze incubation samples from the Metabolic Stability assay. The injection volume was 5 µl and the flow rate was 0.8 ml/min. The gradient used was shown in the table below. All samples were injected with the gradient using mobile phase A and B first. If necessary (for instance, for chromatographic reasons), samples were re-injected with the same gradient, but using mobile phase C and D. All LC-MS/MS analysis parameters were captured electronically in the raw data files.

TABLE 7

Metabolic Stability - Sample Analysis Gradient

| Gradient Time (min) | A % (or C %) | B % (or D %) |
| --- | --- | --- |
| 0.00 | 95 | 5 |
| 0.20 | 95 | 5 |
| 0.30 | 0 | 100 |
| 1.05 | 0 | 100 |
| 1.10 | 95 | 5 |
| 1.50 | 95 | 5 |

Data Analysis

Peak integration was performed with the XCALIBUR® software. The percent remaining calculation was performed by comparing the LC-MS/MS peak areas from the T$_{10 minute}$ samples to those from the T$_{0 minute}$ samples for each compound.

Quality Control

A set of three compounds was tested along with the test compound in each assay plate. Data was accepted and uploaded only if the results for these control compounds fall into the expected ranges shown below.

TABLE 8

Metabolic Stability Assay - Control Compound Values by Microsome Species

| Compound | Average Percent Remaining ± SD | | | | |
|---|---|---|---|---|---|
|  | Human | Rat | Mouse | Dog | Monkey |
| Nefazodone | 0.4 ± 0.4 | 0.7 ± 0.6 | 0.4 ± 0.3 | 0.4 ± 0.4 | 0.6 ± 0.5 |
| Verapamil | 13.3 ± 3.5 | 4.4 ± 2.1 | 13.0 ± 4.2 | 5.6 ± 1.8 | 0.5 ± 0.5 |
| Carbamezepine | 96 ± 6 | 84 ± 9 | 90 ± 10 | 81 ± 7 | 89 ± 13 |

SD = Standard Deviation

Metabolic Stability Half-Life Panel

The rate of metabolism and half-life determined in vitro in human or animal liver microsomes was used to determine intrinsic clearance ($CL_{int}$) and hepatic clearance (CLh,b) of a compound. These parameters were useful for predicting in vivo human clearance, which defines the level of drug exposure in vivo (Obach et al, 1997, 1999).

The metabolic stability half-life assay panel evaluates the time-course and the rate of CYP-mediated (NADPH-dependent) metabolism in vitro in human, rat, mouse, dog and monkey microsomes. The time course spans a 45-minute incubation, and includes 0, 5, 10, 15, 30, and 45 minute time-points, at each of which the amount of test compound remaining in the mixture was measured.

Result Interpretation Guideline

The results of the metabolic stability half-life assay are expressed as a half-life ($T_{1/2}$, min). In general, these results should be used to evaluate only the extent of CYP-mediated, or NADPH-dependent, metabolism of the test compound. When the compound was significantly metabolized ($T_{1/2}$<14 minutes), this indicated high clearance in vivo due to CYP-mediated metabolism. However, if the compound demonstrated moderate (14-70 minutes) or low (>70 minutes) metabolism in these in vitro assays, high clearance was still possible in vivo via other metabolism and elimination pathways.

The results of these assays were predictive of compound clearance in vivo, assuming that CYP-mediated metabolism was a predominant elimination pathway. In human microsomes, the ranges of results were approximately as shown in the following table:

TABLE 9

Metabolic Stability Half-Life-Result Interpretation Guidelines

| CYP-Mediated Clearance | $T_{1/2}$, minutes Human |
|---|---|
| Low | >70 |
| Medium | 14-70 |
| High | <14 |

Methods and Materials

Liver microsomes were purchased from BD Biosciences (Woburn, Mass.) and NADPH from AppliChem Inc; all other reagents were obtained from Sigma.

Incubation with Liver Microsomes

Test compound was received as a 3.5 mM stock solution in 100 percent DMSO. The test compound was diluted to create a 50 µM acetonitrile (ACN) solution containing 1.4% DMSO, which was then used as a 100-fold stock for incubation with microsomes. Each compound was tested in human, rat, mouse, dog and monkey liver microsomes. Compound, NADPH and liver microsome solutions were combined for incubation in three steps:

1. 450 µl of liver microsome suspension, protein concentration of 1.1 mg/ml in 100 mM $NaP_i$, pH 7.4, 5 mM $MgCl_2$ buffer, was pre-warmed at 37° C.

2. 5 µl of 50 µM compound (98.6% ACN, 1.4% DMSO) was added to the same tube and pre-incubated at 37° C. for 5 minutes.

3. The reaction was initiated by the addition of 50 µl of pre-warmed 10 mM NADPH solution in 100 mM $NaP_i$, pH 7.4.

Reaction components were mixed well, and 65 µl were immediately transferred into 130 µl quench/stop solution (zero-time point, $T_0$). Reactions were incubated at 37° C. for 5, 10, 15, 30 and 45 minutes and at each time-point a 65 µl aliquot was transferred into 130 µl of quench solution. Acetonitrile containing Internal Standard (100 ng/ml), was used as the quench solution to terminate metabolic reactions.

Quenched mixtures were centrifuged at 1500 rpm (~500× g) in an ALLEGRA® X-12 centrifuge, SX4750 rotor (Beckman Coulter Inc., Fullerton, Calif.) for fifteen minutes to pellet denatured microsomes. A volume of 90 µl of supernatant extract, containing the mixture of parent compound and its metabolites, was then transferred to a separate 96-well plate for LC/MS-MS analysis to determine the percent of parent compound that was remaining in the mixture.

TABLE 10

Metabolic Stability Half-Life Assays - Reaction Components

| Reaction Components | Final Concentration in the Metabolic Stability Assay |
|---|---|
| Compound (Substrate) | 0.5 µM |
| NaPi Buffer, pH 7.4 | 100 mM |
| DMSO | 0.014% |
| Acetonitrile | 0.986% |
| Microsomes (human, rat, mouse) (BD/Gentest) | 1 mg/ml protein |
| NADPH | 1.0 mM |
| $MgCl_2$ | 5.0 mM |
| 37° C. Incubation time | 0, 5, 10, 15, 30, and 45 minutes |
| Quench/Stop Solution (ACN + 100 µM DMN) | 130 µl |
| Sample of Reaction | 65 µl |
| Sedimentation of Denatured Microsomes | 15 minutes |

Sample Analysis—Instrumentation

HPLC: Pump—Shimadzu LC-20 AD series binary pumps; Autosampler—CTC/LEAP HTS.

Table 11 below lists metabolic half life value for Examples 1-9 of this invention and Comparative Compounds 10-13 measured in the human metabolic stability half-life assay. In some instances, the value is an average of multiple experiments where N is the number of experiments conducted. The compounds of the present invention, as exemplified by Examples 1-9 had metabolic stability half life values of 67 minutes or longer. In contrast, Comparative Compounds 10-13 had metabolic stability half life values of 8 minutes or less.

TABLE 11

| Example | HLM ($t_{1/2}$, min.) | N |
|---|---|---|
| 1 | >120 | 1 |
| 2 | >120 | 1 |
| 3 | 77 | 2 |
| 4 | 103 | 1 |
| 5 | >120 | 1 |
| 6 | 67 | 1 |
| 7 | >120 | 1 |
| 8 | >120 | 1 |
| 9 | >120 | 1 |
| Comparative Compound 10 | 8 | 1 |
| Comparative Compound 11 | 6 | 1 |
| Comparative Compound 12 | 6 | 1 |
| Comparative Compound 13 | 3 | 1 |

The exemplified compounds of the invention showed the surprising advantage of low clearance due to CYP-mediated metabolism in the human metabolic stability half life assay. The compounds of the present invention, as exemplified by Examples 1-9, had metabolic half life values of 67 minutes or longer in the human metabolic stability half life assay. In contrast, Comparative Compounds 10-13 had metabolic half life values of 8 minutes or less in the human metabolic stability assay. Comparative Compounds 10-13 showed high clearance in the human metabolic stability assay, indicating that the compounds were removed by liver microsomes.

The compounds of the present invention (Examples 1-9) have been compared to the Comparative Compounds 10-13 disclosed in U.S. Pat. No. 7,456,172, and have been found to be especially advantageous. The compounds of the present invention had the surprising advantage of the combination of activity as inhibitors of Notch 1 and Notch 3 and superior metabolic stability to liver microsomes. As shown in Tables 3 and 11, in the reported tests, Examples 1-9 of this invention had Notch 1 $IC_{50}$ values of 26.8 nM or less and Notch 3 $IC_{50}$ values of 22.6 nM or less; and human metabolic stability half lives of 67 minutes or longer in the human metabolic stability half life assay. In contrast, in similar tests, Comparative Compounds 10-13 had Notch 1 $IC_{50}$ values of in the range of from 5.1 nM to 64.1 nM and Notch 3 $IC_{50}$ values in the range of 12.5 nM to 74.5 nM; and human metabolic stability half lives of 8 minutes or less.

What is claimed is:

1. A compound of Formula (I):

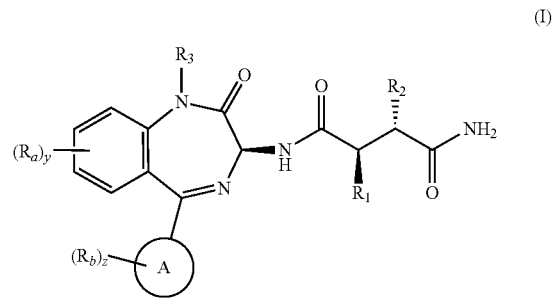

wherein:
R$_1$ is —CH$_2$CF$_2$CH$_3$ or —CH$_2$CH$_2$CF$_3$;
R$_2$ is —CH$_2$CH$_2$CF$_3$, —CH$_2$CH$_2$CH$_2$CF$_3$, or —CH$_2$CF$_2$CH$_3$;
R$_3$ is —CH$_2$CF$_3$, —CH$_2$CN, —CH$_2$(cyclopropyl), pyridinyl, chloropyridinyl, or tetrahydropyranyl;
Ring A is phenyl or pyridinyl;
each R$_a$ is independently F, Cl, Br, —CN, —OH, —CH$_3$, cyclopropyl, —CF$_3$, —CH$_2$CF$_3$, —OCH$_3$, —OCF$_3$, and/or —O(cyclopropyl);
or two adjacent R$_a$ along with the carbon atoms to which they are attached form a dioxole ring;
each R$_b$ is independently F, Cl, —CH$_3$, —CF$_3$, —CN, and/or —OCH$_3$;
y is zero, 1, or 2; and
z is zero, 1, or 2.

2. The compound according to claim 1 wherein:
Ring A is phenyl.

3. The compound according to claim 1 wherein:
R$_2$ is —CH$_2$CH$_2$CF$_3$.

4. The compound according to claim 1 wherein:
R$_3$ is pyridinyl, chloropyridinyl, or tetrahydropyran.

5. The compound according to claim 1 wherein:
R$_3$ is —CH$_2$CF$_3$, —CH$_2$CN, or —CH$_2$(cyclopropyl).

6. The compound according to claim 2 wherein:
R$_a$ is —OCH$_3$;
or two adjacent R$_a$ along with the carbon atoms to which they are attached form a dioxole ring;
R$_b$ is —OCH$_3$;
y is zero, 1, or 2; and
z is zero or 1.

7. A compound according to claim 1 selected from: (2R,3S)-N-((3S)-2-oxo-5-phenyl-1-(2-pyridinyl)-2,3-dihydro-1H-1,4-benzodiazepin-3-yl)-3-(4,4,4-trifluorobutyl)-2-(3,3,3-trifluoropropyl)succinamide (1); (2R,3S)-N-((3S)-1-(5-chloro-2-pyridinyl)-2-oxo-5-phenyl-2,3-dihydro-1H-1,4-benzodiazepin-3-yl)-2,3-bis(3,3,3-trifluoropropyl)succinamide (2); (2R,3S)-N-((7S)-6-oxo-9-phenyl-5-(2-pyridinyl)-6,7-dihydro-5H-[1,3]dioxolo[4,5-h][1,4]benzodiazepin-7-yl)-2,3-bis(3,3,3-trifluoropropyl)succinamide (3); (2R,3S)-N-((3S)-2-oxo-5-phenyl-1-(3-pyridinyl)-2,3-dihydro-1H-1,4-benzodiazepin-3-yl)-3-(4,4,4-trifluorobutyl)-2-(3,3,3-trifluoropropyl)succinamide (4); (2R,3S)-N-((3S)-2-oxo-5-phenyl-1-(3-pyridinyl)-2,3-dihydro-1H-1,4-benzodiazepin-3-yl)-2,3-bis(3,3,3-trifluoropropyl)succinamide (5); (2R,3S)-N-(3S)-1-(cyclopropylmethyl)-5-(4-methoxyphenyl)-2-oxo-2,3-dihydro-1H-1,4-benzodiazepin-3-yl)-2,3-bis(3,3,3-trifluoropropyl)succinamide (6); (2R,3S)-N-((3S)-7-methoxy-2-oxo-5-phenyl-1-(2,2,2-trifluoroethyl)-2,3-dihydro-1H-1,4-benzodiazepin-3-yl)-2,3-bis(3,3,3-trifluoropropyl)succinamide (7); (2R,3S)-N-((3S)-1-(cyclopropylmethyl)-2-oxo-5-phenyl-2,3-dihydro-1H-1,4-benzodiazepin-3-yl)-3-(2,2-difluoropropyl)-2-(3,3,3-trifluoropropyl)succinamide (8); and (2R,3S)-N-((3S)-1-(cyclopropylmethyl)-2-oxo-5-phenyl-2,3-dihydro-1H-1,4-benzodiazepin-3-yl)-2-(2,2-difluoropropyl)-3-(3,3,3-trifluoropropyl)succinamide (9).

8. A pharmaceutical composition comprising a compound according to claim 1; and a pharmaceutically acceptable carrier.

* * * * *